(12) United States Patent
Nagaoka et al.

(10) Patent No.: US 9,985,216 B2
(45) Date of Patent: May 29, 2018

(54) INDENOINDOLE DERIVATIVE AND ORGANIC ELECTROLUMINESCENT ELEMENT

(71) Applicant: HODOGAYA CHEMICAL CO., LTD., Tokyo (JP)

(72) Inventors: Makoto Nagaoka, Tokyo (JP); Shigetaka Numazawa, Tokyo (JP); Norimasa Yokoyama, Tokyo (JP); Si In Kim, Tokyo (JP); Shigeru Kusano, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 150 days.

(21) Appl. No.: 14/894,748

(22) PCT Filed: Jun. 4, 2014

(86) PCT No.: PCT/JP2014/064814
§ 371 (c)(1),
(2) Date: Nov. 30, 2015

(87) PCT Pub. No.: WO2014/196556
PCT Pub. Date: Dec. 11, 2014

(65) Prior Publication Data
US 2016/0126468 A1    May 5, 2016

(30) Foreign Application Priority Data
Jun. 6, 2013  (JP) .................................. 2013-119761

(51) Int. Cl.
| H01L 51/54 | (2006.01) |
| C09K 11/06 | (2006.01) |
| H01L 51/00 | (2006.01) |
| C07D 405/14 | (2006.01) |
| C07D 401/04 | (2006.01) |

(Continued)

(52) U.S. Cl.
CPC ........ *H01L 51/0061* (2013.01); *C07D 209/56* (2013.01); *C07D 209/80* (2013.01); *C07D 209/86* (2013.01); *C07D 401/04* (2013.01); *C07D 401/10* (2013.01); *C07D 403/04* (2013.01); *C07D 403/10* (2013.01); *C07D 403/14* (2013.01); *C07D 405/04* (2013.01); *C07D 405/12* (2013.01); *C07D 405/14* (2013.01); *C07D 409/04* (2013.01); *C07D 409/12* (2013.01); *C07D 413/04* (2013.01); *C07D 413/10* (2013.01); *C07D 417/04* (2013.01); *C07D 417/10* (2013.01); *H01L 51/006* (2013.01); *H01L 51/0052* (2013.01); *H01L 51/0059* (2013.01); *H01L 51/0072* (2013.01); *H01L 51/0073* (2013.01); *H01L 51/0058* (2013.01); *H01L 51/0081* (2013.01);

*H01L 51/5012* (2013.01); *H01L 51/5056* (2013.01); *H01L 51/5092* (2013.01); *H01L 51/5096* (2013.01)

(58) Field of Classification Search
None
See application file for complete search history.

(56) References Cited

U.S. PATENT DOCUMENTS

| 5,639,914 A | 6/1997 | Tomiyama et al. |
| 5,707,747 A | 1/1998 | Tomiyama et al. |

(Continued)

FOREIGN PATENT DOCUMENTS

| CN | 102056899 | 5/2011 |
| CN | 102056911 | 5/2011 |

(Continued)

OTHER PUBLICATIONS

Machine translation of JP2010-040829. Date of publication: Feb. 18, 2010.*

(Continued)

*Primary Examiner* — Andrew K Bohaty
(74) *Attorney, Agent, or Firm* — Greenblum & Bernstein, P.L.C.

(57) ABSTRACT

According to the present invention, there are provided an indenoindole derivative represented by the following general formula (1); and an organic electroluminescent element including a pair of electrodes and at least one organic layer sandwiched therebetween, wherein the above compound is used as a constituent material for the at least one organic layer. The indenoindole derivative of the present invention provides an organic compound, which is excellent in hole injection/transport performance, has electron blocking capability, is highly stable in a thin film state, and excels in heat resistance, as a material for a high efficiency, high durability organic electroluminescent element. An organic electroluminescent element formed using this compound is highly efficient and highly durable.

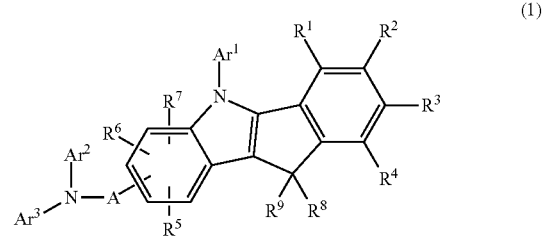

(1)

6 Claims, 8 Drawing Sheets

(51) Int. Cl.

| | |
|---|---|
| *C07D 401/10* | (2006.01) |
| *C07D 403/04* | (2006.01) |
| *C07D 403/10* | (2006.01) |
| *C07D 403/14* | (2006.01) |
| *C07D 405/04* | (2006.01) |
| *C07D 405/12* | (2006.01) |
| *C07D 409/04* | (2006.01) |
| *C07D 409/12* | (2006.01) |
| *C07D 413/04* | (2006.01) |
| *C07D 413/10* | (2006.01) |
| *C07D 417/04* | (2006.01) |
| *C07D 417/10* | (2006.01) |
| *C07D 209/80* | (2006.01) |
| *C07D 209/56* | (2006.01) |
| *C07D 209/86* | (2006.01) |
| *H01L 51/50* | (2006.01) |

(56) References Cited

U.S. PATENT DOCUMENTS

| | | |
|---|---|---|
| 5,792,557 A | 8/1998 | Nakaya et al. |
| 2013/0126856 A1 | 5/2013 | Yokoyama et al. |
| 2014/0167026 A1 | 6/2014 | Kato et al. |

FOREIGN PATENT DOCUMENTS

| | | |
|---|---|---|
| CN | 102056929 | 5/2011 |
| CN | 103038215 | 4/2013 |
| EP | 2 298 774 | 3/2011 |
| EP | 2 301 921 | 3/2011 |
| EP | 2 301 926 | 3/2011 |
| JP | 8-48656 | 2/1996 |
| JP | 3194657 | 6/2001 |
| JP | 2006-219393 | 8/2006 |
| JP | 2010-40829 | 2/2010 |
| WO | WO 2012011756 A1 * | 1/2012 ........... C07D 209/86 |
| WO | 2012/014500 | 2/2012 |
| WO | 2013/011891 | 1/2013 |
| WO | 2014/061960 | 4/2014 |

OTHER PUBLICATIONS

Search Report in International Patent Application No. PCT/JP2014/064814, dated Jul. 15, 2014.

Chinese Office Action issued in Counterpart Patent Appl. No. 201480043575.X, dated Feb. 13, 2017, along with an english translation thereof.

* cited by examiner

8: CATHODE
7: ELECTRON INJECTION LAYER
6: ELECTRON TRANSPORT LAYER
5: LIGHT EMISSION LAYER
4: HOLE TRANSPORT LAYER
3: HOLE INJECTION LAYER
2: TRANSPARENT ANODE
1: GLASS SUBSTRATE

INDENOINDOLE DERIVATIVE AND ORGANIC ELECTROLUMINESCENT ELEMENT

TECHNICAL FIELD

This invention relates to a compound suitable for an organic electroluminescent element, and an organic electroluminescent element. More specifically, the invention relates to an indenoindole derivative, and an organic electroluminescent element using the indenoindole derivative.

BACKGROUND ART

An organic electroluminescent element (may hereinafter be referred to as an organic EL element) is a self light-emitting element, and is thus brighter, better in visibility, and capable of clearer display than a liquid crystal element. Hence, active researches have been conducted on organic EL elements.

In 1987, C. W. Tang et al. of Eastman Kodak developed a laminated structure element sharing various roles among different materials, thereby imparting practical applicability to organic EL elements using organic materials. They laminated a layer of a fluorescent substance capable of transporting electrons, namely, tris(8-hydroxyquinoline)aluminum (will hereinafter be abbreviated as $Alq_3$), and a layer of an aromatic amine compound capable of transporting holes, and injecting the charges of electrons and holes into the layer of the fluorescent substance to perform light emission, thereby obtaining a high luminance of 1,000 $cd/m^2$ or more at a voltage of 10V or less (see Patent Document 1 and Patent Document 2).

Many improvements have been made to date for commercialization of organic EL elements. For example, there is known an electroluminescent element sharing the various roles among more types of materials, and having a positive electrode, a hole injection layer, a hole transport layer, a light emission layer, an electron transport layer, an electron injection layer, and a negative electrode provided in sequence on a substrate. High efficiency and durability are achieved by such an element.

For a further increase in the luminous efficiency, it has been attempted to utilize triplet excitons, and the utilization of phosphorescent light emitting substances has been considered.

Furthermore, elements utilizing light emission by thermally activated delayed fluorescence (TADF) have been developed, and an external quantum efficiency of 5.3% has been realized by an element using a thermally activated delayed fluorescence material.

The light emission layer can also be prepared by doping a charge transporting compound, generally called a host material, with a fluorescent substance or a phosphorescent light emitting substance. The selection of an organic material in the organic EL element greatly affects the characteristics of the element, such as efficiency and durability.

With the organic EL element, charges injected from both electrodes recombine in the light emission layer to obtain light emission, and how efficiently the charges of the holes and electrons are passed on to the light emission layer is of importance. For example, hole injecting properties are enhanced, and the properties of blocking electrons injected from the negative electrode are enhanced to increase the probability of holes and electrons recombining, and excitons generated within the light emission layer are confined, whereby a high luminous efficiency can be obtained. Thus, the role of the hole transport material is so important that there has been a desire for a hole transport material having high hole injection properties, allowing marked hole mobility, possessing high electron blocking properties, and having high durability to electrons.

In connection with the life of the element, heat resistance and amorphism of the material are also important. A material with low thermal resistance is thermally decomposed even at a low temperature by heat produced during element driving, and the material deteriorates. In a material with low amorphism, crystallization of a thin film occurs even in a short time, and the element deteriorates. Thus, high resistance to heat and satisfactory amorphism are required of the material to be used.

As the hole transport materials hitherto used for organic EL elements, N,N'-diphenyl-N,N'-di(α-naphthyl)benzidine (hereinafter NPD, for short) and various aromatic amine derivatives are known (see Patent Document 1 and Patent Document 2). NPD has a satisfactory ability to transport holes, but its glass transition point (Tg) as an index to heat resistance is as low as 96° C., and deterioration of the element characteristics due to crystallization occurs under high temperature conditions. Among the aromatic amine derivatives described in Patent Document 1 and Patent Document 2 are compounds having an excellent hole mobility as high as $10^{-3}$ $cm^2/Vs$ or more. However, their electron blocking properties are insufficient, thus posing the problem that some of the electrons pass through the light emission layer, and an improvement in the luminous efficiency cannot be expected. Thus, a material having high electron blocking properties, providing a more stable thin film, and higher resistance to heat has been desired for an even higher efficiency.

As compounds increased in efficiency and improved in characteristics such as hole transport properties, proposals have been made for arylamine compounds having a substituted indenoindole structure (Compounds A to B) expressed by the following formulas (see Patent Documents 3 to 4):

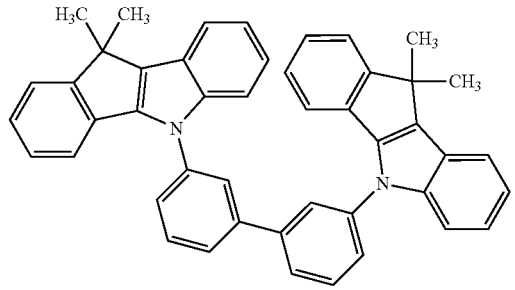

(Compound A)

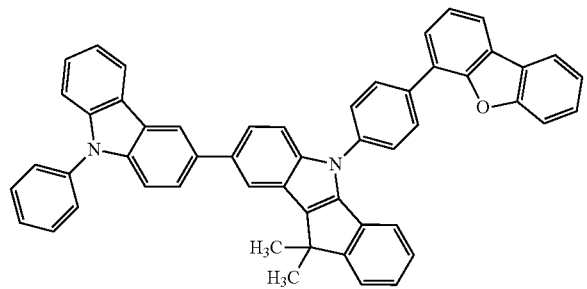

(Compound B)

However, Compound A has only been used as a host material, and an element using Compound B for a hole transport layer has been improved in luminous efficiency, but the improvement has been still insufficient. Thus, there has been a desire for the development of a material which achieves an even lower driving voltage and an even higher luminous efficiency while enhancing heat resistance.

PRIOR ART DOCUMENTS

Patent Documents

Patent Document 1: JP-A-Hei 8-48656
Patent Document 2: Japanese Patent No. 3194657
Patent Document 3: JP-A-2010-40829
Patent Document 4: WO2013-011891

SUMMARY OF THE INVENTION

Problems to be Solved by the Invention

It is an object of the present invention to provide an organic compound, which is excellent in hole injection/transport performance, has electron blocking capability, is highly stable in a thin film state, and excels in heat resistance, as a material for a high efficiency, high durability organic EL element.

It is another object of the present invention to provide an organic EL element having high efficiency and high durability with the use of the organic compound.

Means for Solving the Problems

To attain the above objects, the present inventors paid attention to the facts that an aromatic tertiary amine structure had high ability to inject and transport holes, that an indenoindole ring structure had hole transport ability, and that the indenoindole ring structure was effective for heat resistance and thin film stability. Based on these facts, they designed and chemically synthesized a compound having an indenoindole ring structure. Using the compound, moreover, they experimentally produced various organic EL elements, and extensively evaluated the characteristics of the elements. As a result, they have accomplished the present invention.

According to the present invention, there is provided an indenoindole derivative represented by the following general formula (1)

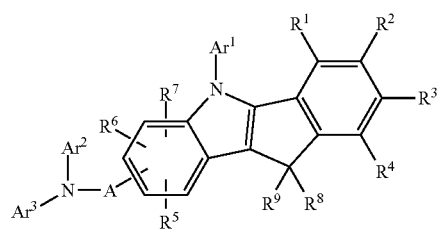

(1)

where
A represents a single bond, a divalent aromatic hydrocarbon group, or a divalent aromatic heterocyclic group,
$Ar^1$, $Ar^2$ and $Ar^3$ may be the same or different, and each represent a monovalent aromatic hydrocarbon group or a monovalent aromatic heterocyclic group, and $Ar^2$ and $Ar^3$ may bind to each other via a single bond, a methylene group, an oxygen atom, or a sulfur atom to form a ring, $R^1$ to $R^7$ may be the same or different, and each represent a hydrogen atom, a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and may bind to each other via a single bond, a methylene group, an oxygen atom, or a sulfur atom to form a ring, $R^8$ and $R^9$ may be the same or different, and each represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and $R^8$ and $R^9$ may bind to each other via a single bond, a methylene group, an oxygen atom, or a sulfur atom to form a ring, and when A is a divalent aromatic hydrocarbon group or a divalent aromatic heterocyclic group, A and $Ar^2$ may bind to each other via a methylene group, an oxygen atom, or a sulfur atom to form a ring.

For the indenoindole derivative of the present invention, the following embodiments are preferred:

(A) At the position indicated in the following general formula (1-1), -A-N—$Ar^2Ar^3$ is bound to the indenoindole ring:

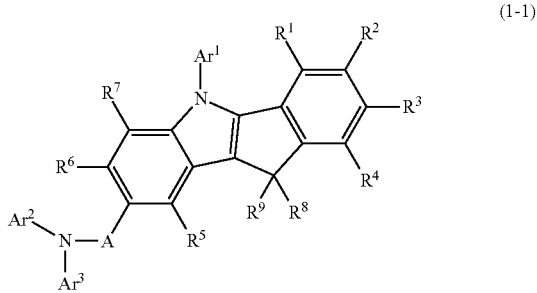

(1-1)

where
A, $Ar^1$ to $Ar^3$, and $R^1$ to $R^9$ have the same meanings as defined above.

(B) In the general formula (1), A is a divalent aromatic hydrocarbon group.

(C) The indenoindole derivative is an indenoindole derivative represented by the following general formula (1-2):

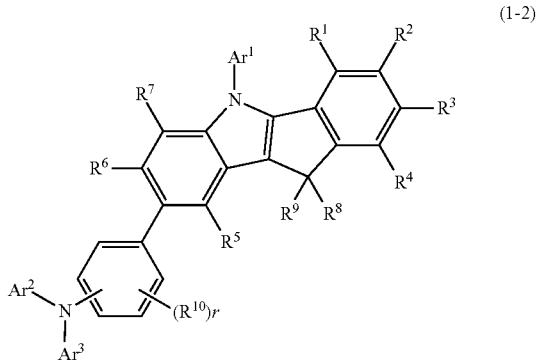

(1-2)

where
Ar$^1$ to Ar$^3$, and R$^1$ to R$^9$ have the same meanings as defined above, r denotes an integer of 0 to 4, and r=0 means that the benzene ring which —N—Ar$^2$Ar$^3$ is bound to is not substituted by R$^{10}$, R$^{10}$ represents a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aryloxy group, or a linking group, and when r is 2 or more, a plurality of R$^{10}$s present may bind to each other to form a ring, and when R$^{10}$ is a linking group, r is 1, and the benzene ring to which R$^{10}$ is bound and Ar$^2$ bind to each other via a methylene group, an oxygen atom, or a sulfur atom to form a ring.

(D) At the position indicated in the following general formula (1-3), —N—Ar$^2$Ar$^3$ is bound to the benzene ring:

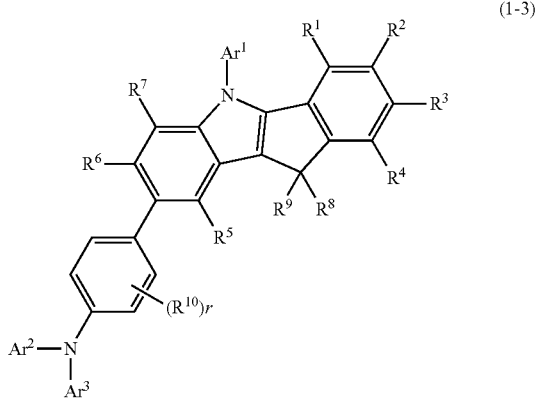

(1-3)

where
Ar$^1$ to Ar$^3$, R$^1$ to R$^{10}$, and r have the same meanings as defined above.

(E) In the general formula (1), A represents a single bond.

(F) At the position indicated in the following general formula (1-4), —N—Ar$^2$Ar$^3$ is bound to the indenoindole ring:

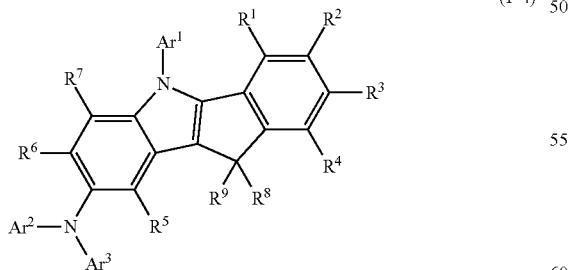

(1-4)

where
Ar$^1$ to Ar$^3$, and R$^1$ to R$^9$ have the same meanings as defined above.

According to the present invention, there is also provided an indenoindole derivative represented by the following general formula (1a)

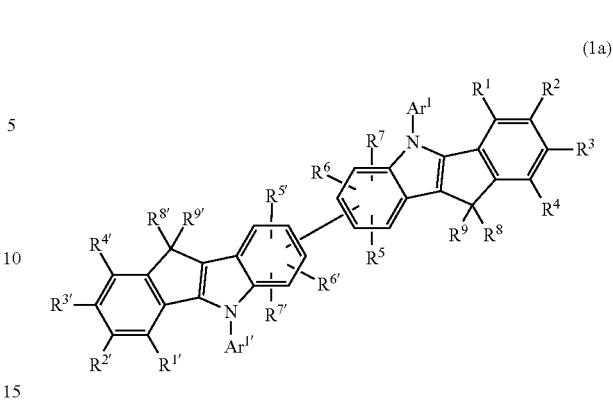

(1a)

where
Ar$^1$ and R$^1$ to R$^9$ have the same meanings as defined above,

Ar$^{1'}$ represents a monovalent aromatic hydrocarbon group or a monovalent aromatic heterocyclic group, R$^{1'}$ to R$^{7'}$ may be the same or different, and each represent a hydrogen atom, a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and may bind to each other via a single bond, a methylene group, an oxygen atom, or a sulfur atom to form a ring, and R$^{8'}$ and R$^{9'}$ may be the same or different, and each represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group, and R$^{8'}$ and R$^{9'}$ may bind to each other via a single bond, a methylene group, an oxygen atom, or a sulfur atom to form a ring.

The indenoindole derivative represented by the above general formula (1a) is (G) preferably an indenoindole derivative represented by the following general formula (1a-1):

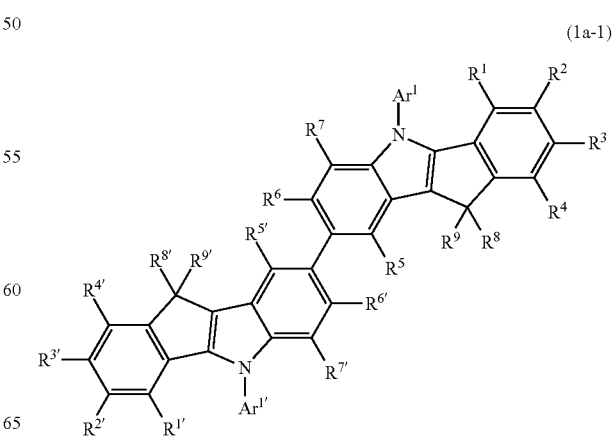

(1a-1)

where

Ar$^1$, Ar$^{1'}$, R$^1$ to R$^9$, and R$^{1'}$ to R$^{9'}$ have the same meanings as defined above.

According to the present invention, moreover, there is provided an organic electroluminescent element including a pair of electrodes and at least one organic layer sandwiched therebetween, wherein the above-mentioned indenoindole derivative is used as a constituent material for the at least one organic layer.

In the organic electroluminescent element of the present invention, it is preferred that (I) the organic layer be a hole transport layer,
(J) the organic layer be an electron blocking layer,
(K) the organic layer be a hole injection layer, and
(L) the organic layer be a light emission layer.

Effects of the Invention

The indenoindole derivative of the present invention is a novel compound having an indenoindole ring and a tertiary amine structure, and has the following properties:

(α) Hole injection characteristics are satisfactory.
(β) Hole mobility is high.
(γ) Electron blocking capability is excellent.
(δ) Thin film state is stable.
(ε) Heat resistance is excellent.

Hence, the organic EL element including the organic layer containing the above indenoindole derivative as a constituent material has the following properties:

(α) Luminous efficiency and power efficiency are high.
(β) Light emission starting voltage is low.
(γ) Practical driving voltage is low.

The indenoindole derivative of the present invention can be used, for example, as a constituent material for the hole injection layer and/or the hole transport layer of the organic EL element. The indenoindole derivative of the present invention (a) has high properties of injecting holes,
(b) ensures high hole mobility,
(c) shows high properties of blocking electrons, and
(d) is highly stable to electrons, as compared with conventional materials. Thus, the hole injection layer and the hole transport layer, which are obtained using the indenoindole derivative of the present invention as their constituent material, can confine excitons generated within the light emission layer, and are improved in the probability of recombination of holes and electrons. Consequently, they can obtain a high luminous efficiency, lower the driving voltage, and improve the durability of the organic EL element.

The indenoindole derivative of the present invention can also be used as a constituent material for the electron blocking layer of the organic EL element. The indenoindole derivative of the present invention (e) has excellent ability to block electrons,
(f) is better in hole transporting properties than conventional materials, and
(g) is highly stable in a thin film state.

With the electron blocking layer obtained using the indenoindole derivative of the present invention as the constituent material, therefore, a high luminous efficiency is exhibited, driving voltage is lowered, and current resistance is improved. As a result, the maximum light emission luminance of the organic EL element is increased.

Furthermore, the indenoindole derivative of the present invention is also usable as a constituent material for the light emission layer of the organic EL element. The indenoindole derivative of the present invention (h) has excellent hole transport properties, and
(i) has a wide bandgap, as compared with conventional materials. Thus, the indenoindole derivative of the present invention is used as a host material of the light emission layer, and a fluorescence emitting substance or a phosphorescence emitting substance, called a dopant, is supported in the host material to obtain the light emission layer. By so doing, an organic EL element decreased in driving voltage and increased in luminous efficiency can be realized.

The organic EL element of the present invention uses an indenoindole derivative which is higher in hole transport ability than conventional hole transport materials, is better in electron blocking capability, and is more stable in a thin film state. Thus, this organic EL element realizes high efficiency and high durability.

As described above, the indenoindole derivative of the present invention is useful as a constituent material for the hole injection layer, the hole transport layer, the electron blocking layer, or the light emission layer of an organic EL element, has excellent ability to block electrons, is stable in a thin film state, and excels in heat resistance. The organic EL element of the present invention is so high in luminous efficiency and power efficiency that it can lower the practical driving voltage of the element. Since the light emission starting voltage can be lowered, its durability can be improved.

MODE FOR CARRYING OUT THE INVENTION

Figure 1:
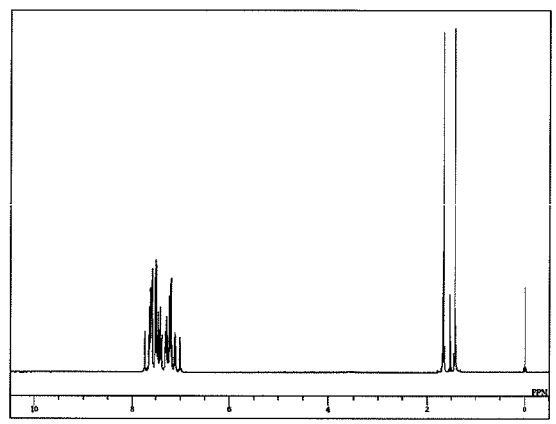
FIG. 1 is a $^1$H-NMR chart diagram of compound of Example 1 (Compound 10).

The novel indenoindole derivative of the present invention is represented by the following general formula (1), and its basic skeleton has an indenoindole ring structure and an aromatic tertiary amine structure:

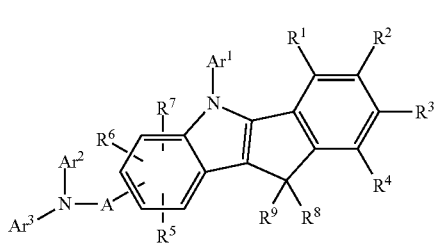

(1)

<A>

In the above general formula (1), A represents a single bond, a divalent aromatic hydrocarbon group, or a divalent aromatic heterocyclic group. The divalent aromatic hydrocarbon group and the divalent aromatic heterocyclic group may each have a condensed polycyclic structure.

Examples of the aromatic hydrocarbon and aromatic heterocycle that these groups have are benzene, biphenyl, terphenyl, tetrakisphenyl, styrene, naphthalene, anthracene, acenaphthalene, fluorene, phenanthrene, indane, pyrene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridan. As the aromatic heterocycles, sulfur-containing aromatic heterocycles such as thiophene, benzothiophene, benzothiazole, and dibenzothiophene, or oxygen-containing aromatic heterocycles such as furan, benzofuran, benzoxazole, and dibenzofuan are preferred.

The divalent aromatic hydrocarbon group or divalent aromatic heterocyclic group represented by A represents a divalent group formed by removing two hydrogen atoms from the above-mentioned aromatic hydrocarbon or aromatic heterocycle.

The above aromatic hydrocarbon or aromatic heterocycle may have a substituent. Examples of the substituent are:

a heavy hydrogen atom;
a cyano group;
a nitro group;
a halogen atom, for example, a fluorine atom, a chlorine atom, a bromine atom, or an iodine atom;
an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;
an alkyloxy group having 1 to 6 carbon atoms, for example, a methyloxy group, an ethyloxyl group, or a propyloxy group;
an alkenyl group, for example, an allyl group;
an aryloxy group, for example, a phenyloxy group or a tolyloxy group;
an arylalkyloxy group, for example, a benzyloxy group or a phenethyloxy group;
an aromatic hydrocarbon group or a condensed polycyclic aromatic group, for example, a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group, or a triphenylenyl group;
an aromatic heterocyclic group, for example, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, or a carbolinyl group;
an arylvinyl group, for example, a styryl group or a naphthylvinyl group; and
an acyl group, for example, an acetyl group or a benzoyl group.

Of the above substituents, the alkyl group having 1 to 6 carbon atoms or the alkyloxy group having 1 to 6 carbon atoms may be straight-chain or branched.

The above substituents may be further substituted by the above exemplary substituent, on condition that the limitation on the number of carbon atoms is not impaired. Moreover, the substituents may bind to each other via a single bond, a substituted or unsubstituted methylene group, an oxygen atom, or a sulfur atom to form a ring, although this is not greatly preferred.

If A is the divalent aromatic hydrocarbon group or the divalent aromatic heterocyclic group, A may bind to the group $Ar^2$ to be described later, thereby forming a ring. From the viewpoint of imparting better hole injection/transport capability, however, it is preferred that A and $Ar^2$ be present independently of each other so as not to form a ring. In forming a ring, A and $Ar^2$ bind to each other via a substituted or unsubstituted methylene group, an oxygen atom, or a sulfur atom to form a ring. This is because hole injection/transport capability can be enhanced more greatly than when a ring is formed by binding via a single bond.

<$Ar^1$ to $Ar^3$>

$Ar^1$, $Ar^2$ and $Ar^3$ may be the same or different, and each represent a monovalent aromatic hydrocarbon group or a monovalent aromatic heterocyclic group. The monovalent aromatic hydrocarbon group and the monovalent aromatic heterocyclic group may each have a condensed polycyclic structure.

The monovalent aromatic hydrocarbon group and the monovalent aromatic heterocyclic group can be exemplified by a phenyl group, a biphenylyl group, a terphenylyl group, a naphthyl group, an anthryl group, a phenanthryl group, a fluorenyl group, an indenyl group, a pyrenyl group, a perylenyl group, fluoranthenyl group, a triphenylenyl group, a pyridyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, and a carbolinyl group. Of these groups, a sulfur-containing aromatic heterocyclic group, such as a thienyl group, a benzothienyl group, a benzothiazolyl group, or a dibenzothienyl group, or an oxygen-containing aromatic heterocyclic group, such as a furyl group, a benzofuranyl group, a benzoxazolyl group, or a dibenzofuranyl group, is preferred as the aromatic heterocyclic group.

$Ar^2$ and $Ar^3$ may either bind to each other via a single bond, a substituted or unsubstituted methylene group, an oxygen atom, or a sulfur atom to form a ring, or may exist independently of each other without forming a ring.

The above-mentioned monovalent aromatic hydrocarbon group and monovalent aromatic heterocyclic group may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group.

<$R^1$ to $R^7$>

In the general formula (1), $R^1$ to $R^7$ may be the same or different, and each represent a hydrogen atom, a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The alkyl group having 1 to 6 carbon atoms, the cycloalkyl group having 5 to 10 carbon atoms, and the alkenyl group having 2 to 6 carbon atoms, represented by R' to $R^7$, can be exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group. The alkyl group having 1 to 6 carbon atoms or the alkenyl group having 2 to 6 carbon atoms may be straight-chain or branched.

The alkyloxy group having 1 to 6 carbon atoms and the cycloalkyloxy group having 5 to 10 carbon atoms, represented by $R^1$ to $R^7$, can be exemplified by a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group. The alkyloxy group having 1 to 6 carbon atoms may be straight-chain or branched.

The monovalent aromatic hydrocarbon group and monovalent aromatic heterocyclic group, represented by $R^1$ to $R^7$, can be exemplified by the same groups illustrated as the monovalent aromatic hydrocarbon group and monovalent aromatic heterocyclic group in connection with $Ar^1$ to $Ar^3$. The monovalent aromatic hydrocarbon group and the monovalent aromatic heterocyclic group may each have a condensed polycyclic structure, like those for $Ar^1$ to $Ar^3$.

The aryloxy group, represented by $R^1$ to $R^7$, can be exemplified by a phenyloxy group, a biphenylyloxy group, a terphenylyloxy group, a naphthyloxy group, an anthryloxy group, a phenanthryloxy group, a fluorenyloxy group, an indenyloxy group, a pyrenyloxy group, and a perylenyloxy group.

The above groups, represented by $R^1$ to $R^7$, may bind to each other via a single bond, a substituted or unsubstituted methylene group, an oxygen atom, or a sulfur atom to form a ring, or may be present independently of each other without forming a ring.

The above-mentioned groups represented by $R^1$ to $R^7$ may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group.

<$R^8$, $R^9$>

$R^8$ and $R^9$ may be the same or different, and each represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The alkyl group having 1 to 6 carbon atoms, the cycloalkyl group having 5 to 10 carbon atoms, and the alkenyl group having 2 to 6 carbon atoms, represented by $R^8$ and $R^9$, can be exemplified by the same groups as those illustrated as the alkyl group having 1 to 6 carbon atoms, the cycloalkyl group having 5 to 10 carbon atoms, and the alkenyl group having 2 to 6 carbon atoms represented by $R^1$ to $R^7$. The alkyl group having 1 to 6 carbon atoms and the alkenyl group having 2 to 6 carbon atoms may each be straight-chain or branched, as may those for $R^1$ to $R^7$.

The alkyloxy group having 1 to 6 carbon atoms and the cycloalkyloxy group having 5 to 10 carbon atoms, represented by $R^8$ and $R^9$, can be exemplified by the same groups as those illustrated as the alkyloxy group having 1 to 6 carbon atoms or the cycloalkyloxy group having 5 to 10 carbon atoms represented by $R^1$ to $R^7$. The alkyloxy group having 1 to 6 carbon atoms may be straight-chain or branched, as may that for $R^1$ to $R^7$.

The monovalent aromatic hydrocarbon group and monovalent aromatic heterocyclic group, represented by $R^8$ and $R^9$, can be exemplified by the same groups illustrated as the monovalent aromatic hydrocarbon group and monovalent aromatic heterocyclic group represented by $Ar^1$ to $Ar^3$. The monovalent aromatic hydrocarbon group and the monovalent aromatic heterocyclic group may each have a condensed polycyclic structure, like those for $Ar^1$ to $Ar^3$.

The aryloxy group, represented by $R^8$ and $R^9$, can be exemplified by the same groups as those illustrated as the aryloxy group represented by $R^1$ to $R^7$.

The above groups $R^8$ and $R^9$ may bind to each other via a single bond, a substituted or unsubstituted methylene group, an oxygen atom, or a sulfur atom to form a ring, or may be present independently of each other without forming a ring.

The above-mentioned groups represented by $R^8$ and $R^9$ may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group represented by A.

<Preferred Structure>

In the indenoindole derivative of the present invention represented by the general formula (1), it is preferred that -A-N—$Ar^2Ar^3$ be bound to the benzene ring in the indole ring at the para-position relative to the nitrogen atom. Such an embodiment is represented by the following general formula (1-1):

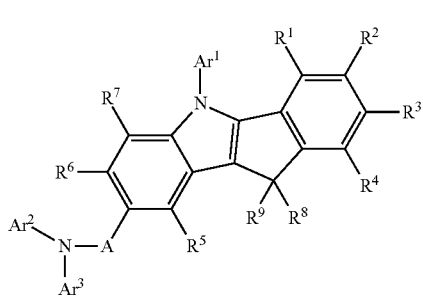

(1-1)

where

A, $Ar^1$ to $Ar^3$, and $R^1$ to $R^9$ have the meanings defined in the aforementioned general formula (1).

The indenoindole derivative of the present invention, represented by the general formula (1) or (1-1), can be classified into two types, i.e., a type in which A is a divalent aromatic hydrocarbon group or a divalent aromatic heterocyclic group, and a type in which A is a single bond. In the type in which A is a divalent aromatic hydrocarbon group or a divalent aromatic heterocyclic group, A is preferably a divalent aromatic hydrocarbon group. Particularly, the indenoindole derivative is preferably an indenoindole derivative as represented by the following formula (1-2):

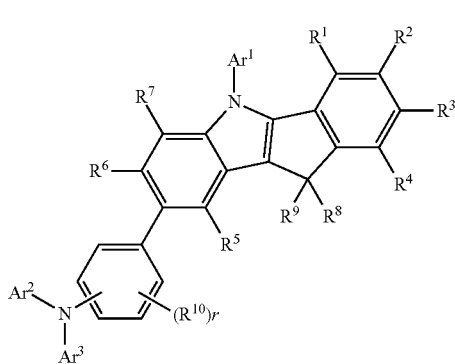

(1-2)

where $Ar^1$ to $Ar^3$ and $R^1$ to $R^9$ have the meanings defined in the aforementioned general formula (1).

r denotes the number of the groups $R^{10}$s, which is an integer of 0 to 4. When r is 0, the benzene ring which —N—$Ar^2Ar^3$ is bound to {the benzene ring corresponding to the group A in the general formula (1)} is not substituted by $R^{10}$, that is, the substituent $R^{10}$ is not present in the benzene ring. When $R^{10}$ is a linking group, r is 1, and the benzene ring having $R^{10}$ bound thereto and $Ar^2$ bind to each other via a substituted or unsubstituted methylene group, an oxygen atom or a sulfur atom to form a ring. That is, $R^{10}$ is a substituted or unsubstituted methylene group, an oxygen atom, or a sulfur atom to connect the benzene ring having $R^{10}$ bound thereto with —N—$Ar^2Ar^3$. When r is 2 or more, a plurality of $R^{10}$s present in the benzene ring may be the same or different, and may bind to each other to form a ring, or may be present independently of each other without forming a ring.

<$R^{10}$>

$R^{10}$ represents a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aryloxy group, or a linking group.

The alkyl group having 1 to 6 carbon atoms, the cycloalkyl group having 5 to 10 carbon atoms, and the alkenyl group having 2 to 6 carbon atoms, represented by $R^{10}$, can be exemplified by the same groups as those illustrated as the alkyl group having 1 to 6 carbon atoms, the cycloalkyl group having 5 to 10 carbon atoms, and the alkenyl group having 2 to 6 carbon atoms represented by $R^1$ to $R^7$. The alkyl group having 1 to 6 carbon atoms and the alkenyl group having 2 to 6 carbon atoms may each be straight-chain or branched, as may those for $R^1$ to $R^7$.

The alkyloxy group having 1 to 6 carbon atoms and the cycloalkyloxy group having 5 to 10 carbon atoms, represented by $R^{10}$, can be exemplified by the same groups as those illustrated as the alkyloxy group having 1 to 6 carbon atoms or the cycloalkyloxy group having 5 to 10 carbon atoms represented by $R^1$ to $R^7$. The alkyloxy group having 1 to 6 carbon atoms may be straight-chain or branched, as may that for $R^1$ to $R^7$.

The monovalent aromatic hydrocarbon group and monovalent aromatic heterocyclic group, represented by $R^{10}$, can be exemplified by the same groups as those illustrated as the monovalent aromatic hydrocarbon group and monovalent aromatic heterocyclic group represented by $Ar^1$ to $Ar^3$. The monovalent aromatic hydrocarbon group and the monovalent aromatic heterocyclic group may each have a condensed polycyclic structure, like those for $Ar^1$ to $Ar^3$.

The aryloxy group, represented by $R^{10}$, can be exemplified by the same groups as those illustrated as the aryloxy group represented by $R^1$ to $R^7$.

The above-mentioned groups represented by $R^{10}$ may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group represented by A.

Furthermore, the indenoindole derivative of the present invention represented by the above general formula (1-2) is preferably one in which —N—$Ar^2Ar^3$ is bound to the benzene ring, which can be substituted by the group $R^{10}$, at the position indicated in the following general formula (1-3):

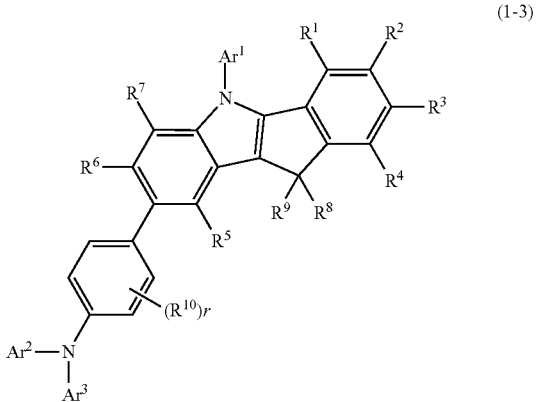

(1-3)

where

Ar¹ to Ar³, R¹ to R¹⁰, and r have the meanings defined in the general formula (1-2).

On the other hand, the indenoindole derivative of the present invention of the type in which A is a single bond is preferably one in which —N—Ar²Ar³ is bound to the indenoindole ring at the position indicated in the following general formula (1-4):

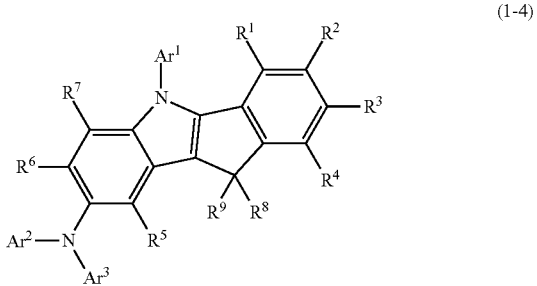

(1-4)

where

Ar¹ to Ar³ and R¹ to R⁹ have the meanings defined in the general formula (1).

Besides, the indenoindole derivative of the present invention involves an embodiment in which an indenoindole ring is present in the portion corresponding to the aromatic tertiary amine (-A-N—Ar²Ar³). Such an indenoindole derivative is represented by the following general formula (1a):

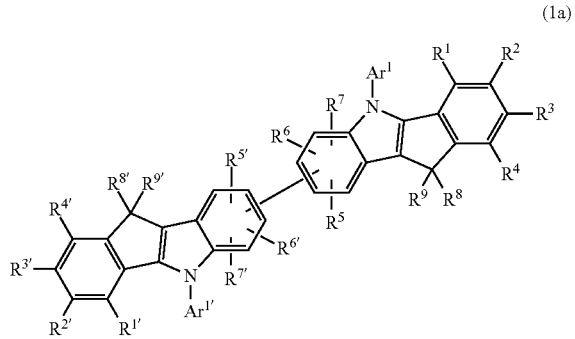

(1a)

where

Ar¹ and R¹ to R⁹ have the same meanings as defined in the general formula (1).

<Ar¹'>

Ar¹' represents a monovalent aromatic hydrocarbon group or a monovalent aromatic heterocyclic group. The monovalent aromatic hydrocarbon group and monovalent aromatic heterocyclic group, represented by Ar¹', can be exemplified by the same groups as those illustrated as the monovalent aromatic hydrocarbon group and monovalent aromatic heterocyclic group represented by Ar¹ to Ar³. The monovalent aromatic hydrocarbon group and the monovalent aromatic heterocyclic group may each have a condensed polycyclic structure, like those for Ar¹ to Ar³.

The above-mentioned monovalent aromatic hydrocarbon group and monovalent aromatic heterocyclic group may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group represented by A.

<R¹' to R⁷'>

R¹' to R⁷' may be the same or different, and each represent a hydrogen atom, a heavy hydrogen atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The alkyl group having 1 to 6 carbon atoms, the cycloalkyl group having 5 to 10 carbon atoms, the alkenyl group having 2 to 6 carbon atoms, the alkyloxy group having 1 to 6 carbon atoms, the cycloalkyloxy group having 5 to 10 carbon atoms, the monovalent aromatic hydrocarbon group, the monovalent aromatic heterocyclic group, and the aryloxy group, represented by R¹' to R⁷', can be exemplified by the same groups as those illustrated as the alkyl group having 1 to 6 carbon atoms, the cycloalkyl group having 5 to 10 carbon atoms, the alkenyl group having 2 to 6 carbon atoms, the alkyloxy group having 1 to 6 carbon atoms, the cycloalkyloxy group having 5 to 10 carbon atoms, the monovalent aromatic hydrocarbon group, the monovalent aromatic heterocyclic group, and the aryloxy group represented by R¹ to R⁷. The alkyl group having 1 to 6 carbon atoms, the alkenyl group having 2 to 6 carbon atoms, and the alkyloxy group having 1 to 6 carbon atoms may each be straight-chain or branched, as may those for R¹ to R⁷.

The above groups, represented by R¹' to R, may bind to each other via a single bond, a substituted or unsubstituted methylene group, an oxygen atom, or a sulfur atom to form a ring, or may be present independently of each other without forming a ring.

The above-mentioned groups represented by R¹' to R⁷' may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group.

<$R^{8'}$, $R^{9'}$>

$R^{8'}$ and $R^{9'}$ may be the same or different, and each represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The alkyl group having 1 to 6 carbon atoms, the cycloalkyl group having 5 to 10 carbon atoms, the alkenyl group having 2 to 6 carbon atoms, the alkyloxy group having 1 to 6 carbon atoms, the cycloalkyloxy group having 5 to 10 carbon atoms, the monovalent aromatic hydrocarbon group, the monovalent aromatic heterocyclic group, and the aryloxy group, represented by $R^{8'}$ and $R^{9'}$, can be exemplified by the same groups as those illustrated as the alkyl group having 1 to 6 carbon atoms, the cycloalkyl group having 5 to 10 carbon atoms, the alkenyl group having 2 to 6 carbon atoms, the alkyloxy group having 1 to 6 carbon atoms, the cycloalkyloxy group having 5 to 10 carbon atoms, the monovalent aromatic hydrocarbon group, the monovalent aromatic heterocyclic group, and the aryloxy group represented by $R^8$ and $R^9$. The alkyl group having 1 to 6 carbon atoms, the alkenyl group having 2 to 6 carbon atoms, and the alkyloxy group having 1 to 6 carbon atoms may each be straight-chain or branched, as may those for $R^8$ and $R^9$.

The above groups $R^{8'}$ and $R^{9'}$ may bind to each other via a single bond, a substituted or unsubstituted methylene group, an oxygen atom, or a sulfur atom to form a ring, or may be present independently of each other without forming a ring.

The above-mentioned groups represented by $R^{8'}$ and $R^{9'}$ may also have a substituent. The substituent can be exemplified by the same ones as those illustrated in connection with the divalent aromatic hydrocarbon group and divalent aromatic heterocyclic group represented by A. Such a substituent may be straight-chain or branched, and may further have a substituent. Furthermore, the above substituents may bind to each other to form a ring, although this is not greatly preferred. These options are the same as those for the aforementioned divalent aromatic hydrocarbon group and divalent aromatic heterocyclic group represented by A.

Particularly preferred as the above-mentioned indenoindole derivative represented by the general formula (1a) is one in which two indenoindole rings are bound together at the position indicated in the following general formula (1a-1):

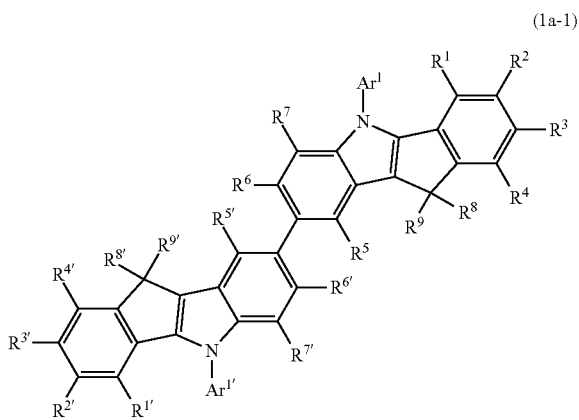

(1a-1)

where $Ar^1$, $Ar^3$, $R^1$ to $R^9$, and $R^{1'}$ to $R^{9'}$ have the meanings defined in the general formula (1a).

As A, a divalent aromatic hydrocarbon group or a single bond is preferred from the viewpoint of imparting better hole injection/transport capability. Particularly, "a divalent group derived from benzene" or a single bond is preferred.

As $Ar^1$, a monovalent aromatic hydrocarbon group is preferred, a phenyl group, a biphenylyl group, a terphenylyl group, a naphthyl group, an anthryl group, a phenanthryl group, a triphenylenyl group, a fluorenyl group, and an indenyl group are more preferred, and a phenyl group, a biphenylyl group, a naphthyl group, and a fluorenyl group are particularly preferred.

As $Ar^2$, a monovalent aromatic hydrocarbon group is preferred, a phenyl group, a biphenylyl group, a terphenylyl group, a naphthyl group, an anthryl group, a phenanthryl group, a triphenylenyl group, a fluorenyl group, and an indenyl group are more preferred, and a phenyl group, a biphenylyl group, a naphthyl group, a fluorenyl group, and an indenyl group are particularly preferred.

As $Ar^3$, a monovalent aromatic hydrocarbon group is preferred, a phenyl group, a biphenylyl group, a terphenylyl group, a naphthyl group, an anthryl group, a phenanthryl group, a triphenylenyl group, a fluorenyl group, and an indenyl group are more preferred, and a phenyl group, a biphenylyl group, a naphthyl group, a fluorenyl group, and an indenyl group are particularly preferred.

As $Ar^{1'}$, a monovalent aromatic hydrocarbon group is preferred, a phenyl group, a biphenylyl group, a terphenylyl group, a naphthyl group, an anthryl group, a phenanthryl group, a triphenylenyl group, a fluorenyl group, and an indenyl group are more preferred, and a phenyl group, a biphenylyl group, a naphthyl group, and a fluorenyl group are particularly preferred.

<Manufacturing Method>

The indenoindole derivative of the present invention can be synthesized, for example, by the following manufacturing method: A 10,10-dimethyl-5,10-dihydroindeno[1,2-b]indole derivative is provided, and the 5-position of such an indenoindole derivative is substituted by an aryl group. Then, its 3-position is brominated, and the resulting bromine-substituted product and an amine having a structure corresponding to -A-N—$Ar^2Ar^3$, which the desired indenoindole derivative has, are subjected to a condensation reaction, whereby the target product can be synthesized. The sequence of the aryl-substitution reaction at the 5-position, the bromination at the 3-position, and the condensation reaction for amine introduction may be changed, as appropriate, according to the status, for example, of the structure of the desired indenoindole derivative.

The 10,10-dimethyl-5,10-dihydroindeno[1,2-b]indole derivative can be synthesized, for example, by a reaction between the corresponding phenylhydrazine hydrochloride and 3,3-dimethyl-1-indanone.

The aryl-substitution reaction at the 5-position can be performed, for example, by a condensation reaction between the resulting 10,10-dimethyl-5,10-dihydroindeno[1,2-b]indole derivative and iodinated aryl, by way of, say, Ullmann reaction or Buchwald Hartwig reaction.

The bromination at the 3-position can be performed, for example, by brominating the 10,10-dimethyl-5,10-dihydroindeno[1,2-b]indole derivative, which has been substituted at the 5-position by an aryl group, with N-bromosuccinimide or the like. By changing a reagent and conditions for bromination on this occasion, a bromo-substituted product different in the position of substitution can be obtained.

The introduction of amine by the condensation reaction can be performed concretely by a cross-coupling reaction, such as Suzuki coupling, between the 5-aryl-10,10-dimethyl-5,10-dihydroindeno[1,2-b]indole derivative, which has been brominated at the 3-position, and boronic acid or boronic ester having a structure corresponding to -A-N—Ar²Ar³ in the desired indenoindole derivative. Alternatively, the amine introduction can be carried out by relying on a condensation reaction such as Buchwald Hartwig reaction or Ullmann reaction with an amine having a structure corresponding to -A-N—Ar²Ar³ in the desired indenoindole derivative. The amine used may, if necessary, contain boron in its structure (e.g., borolane).

Where necessary, a cross-coupling reaction, such as Suzuki coupling, between the resulting bromo-substituted product and various boronic acids or boronic esters may be performed before the condensation reaction for introduction of the amine structure. After the cross-coupling reaction, such as Suzuki coupling, a condensation reaction using iodinated aryl, such as Ullmann reaction, may be conducted further. The condensation reaction for introduction of the amine structure, such as Buchwald Hartwig reaction, may be performed a plurality of times, if necessary, with the reactants being changed.

The purification of the resulting compound can be performed, for example, by purification using a column chromatograph, adsorption purification using silica gel, activated carbon, activated clay or the like, recrystallization using a solvent, or crystallization. Identification of the compound can be performed by NMR analysis. As physical property values, a glass transition point (Tg) and a work function can be measured.

The glass transition point (Tg) serves as an index to stability in a thin film state. The glass transition point (Tg) can be obtained by a high sensitivity differential scanning calorimeter (DSC3100S, produced by Bruker AXS) using a powder.

The work function serves as an index to hole transport properties. The work function can be measured by preparing a 100 nm thin film on an ITO substrate and using an ionization potential measuring device (PYS-202, produced by Sumitomo Heavy Industries, Ltd.) on the sample.

Of the indenoindole derivatives represented by the general formula (1), concrete examples of preferred compounds will be shown below, but the present invention is in no way limited to these compounds. Compound Nos. 1 to 4 are missing.

Formulas (1-1), (1-2), (1-3)

(Compound 5)

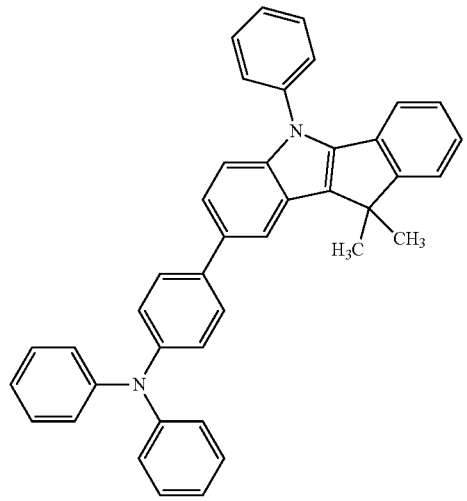

A = benzene

Formulas (1-1), (1-2), (1-3)

(Compound 6)

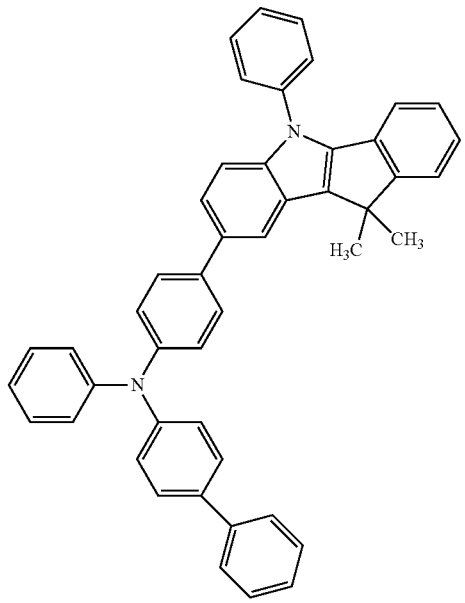

A = benzene

Formulas (1-1), (1-2), (1-3)

(Compound 7)

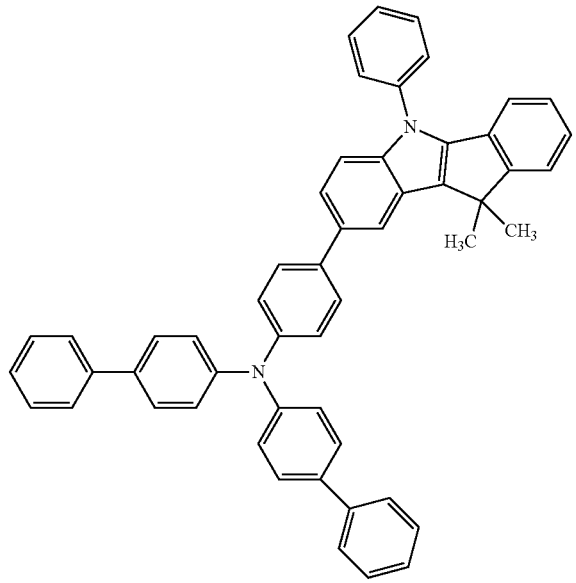

A = benzene

Formulas (1-1), (1-2), (1-3)
(Compound 8)
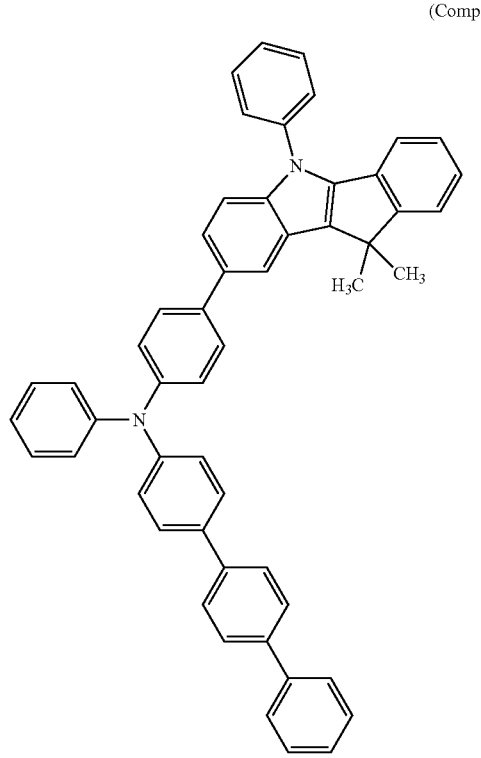
A = benzene
Formulas (1-1), (1-2), (1-3)
(Compound 9)
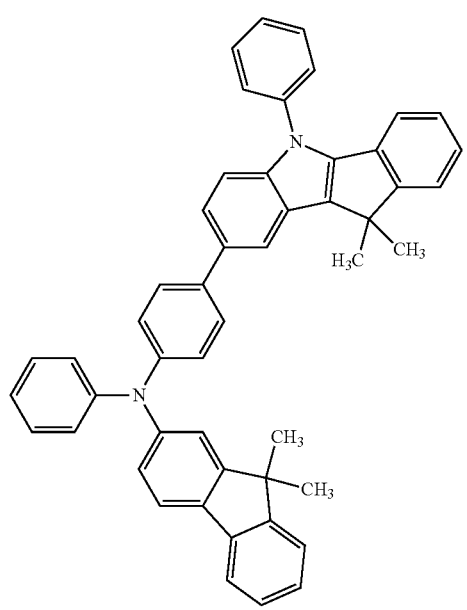
A = benzene
Formulas (1-1), (1-2), (1-3)
(Compound 10)
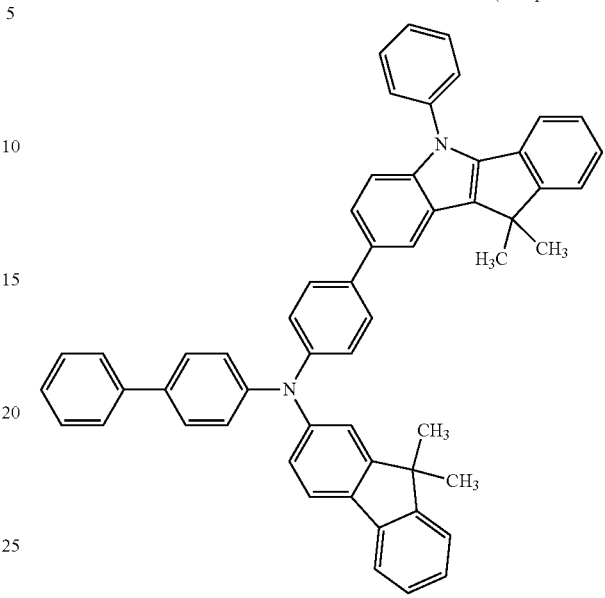
A = benzene
Formulas (1-1), (1-2), (1-3)
(Compound 11)
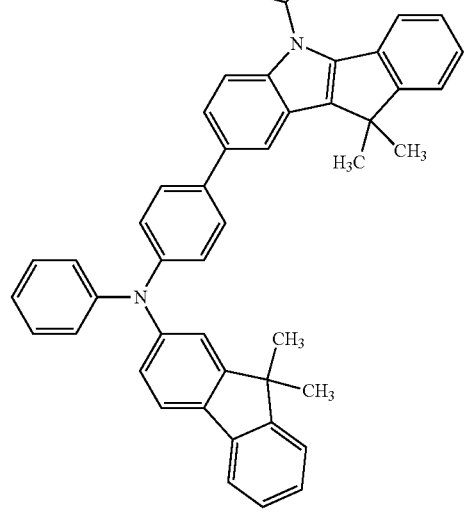
A = benzene Formulas (1-1), (1-2), (1-3)
(Compound 12)
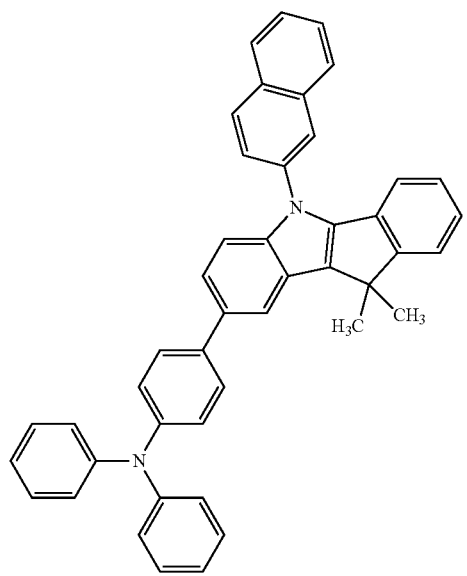
A = benzene
Formulas (1-1), (1-2), (1-3)
(Compound 13)
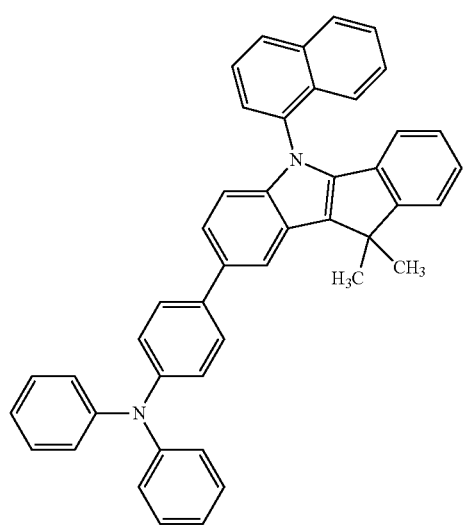
A = benzene
Formulas (1-1), (1-2), (1-3)
(Compound 14)
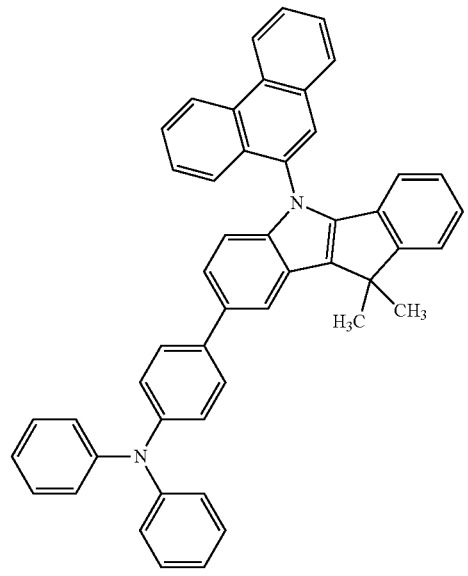
A = benzene
Formulas (1-1), (1-2), (1-3)
(Compound 15)
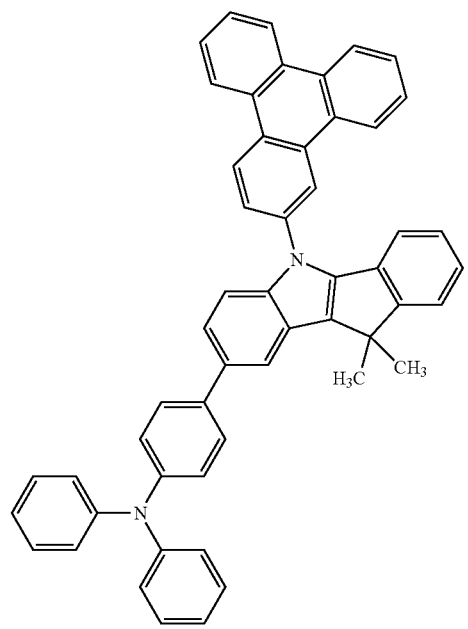
A = benzene Formulas (1-1), (1-2), (1-3)
(Compound 16)
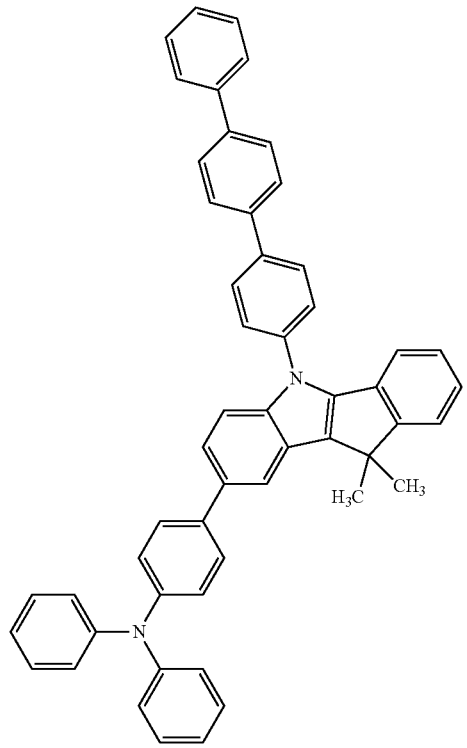
A = benzene
Formulas (1-1), (1-2), (1-3)
(Compound 17)
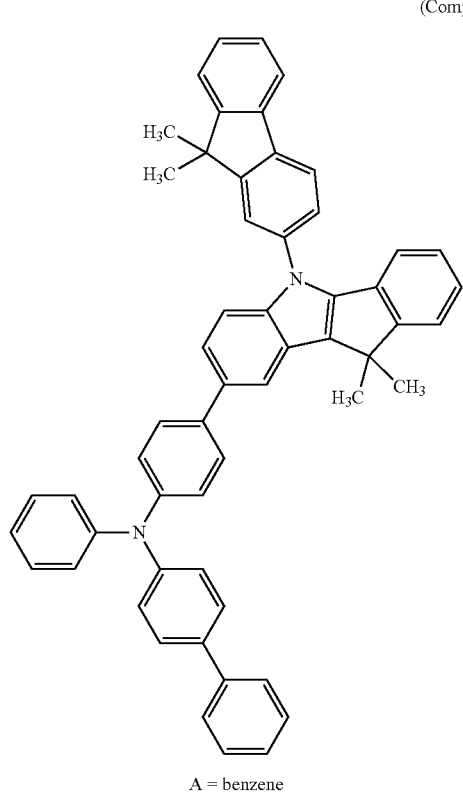
A = benzene
Formulas (1-1), (1-2), (1-3)
(Compound 18)
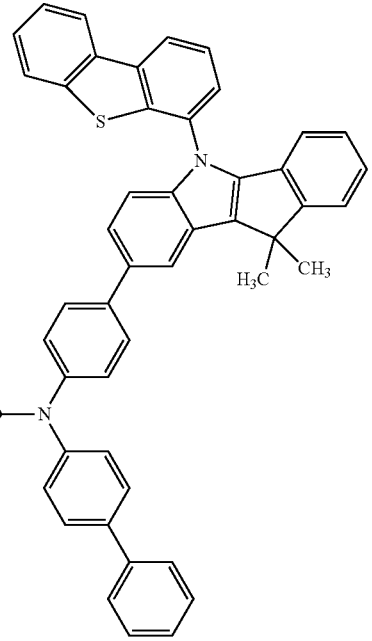
A = benzene
Formulas (1-1), (1-2), (1-3)
(Compound 19)
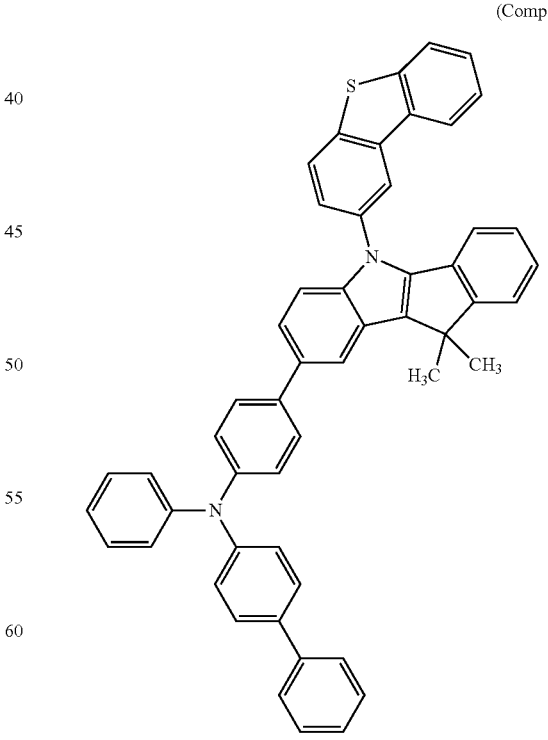
A = benzene Formulas (1-1), (1-2), (1-3)
(Compound 20)
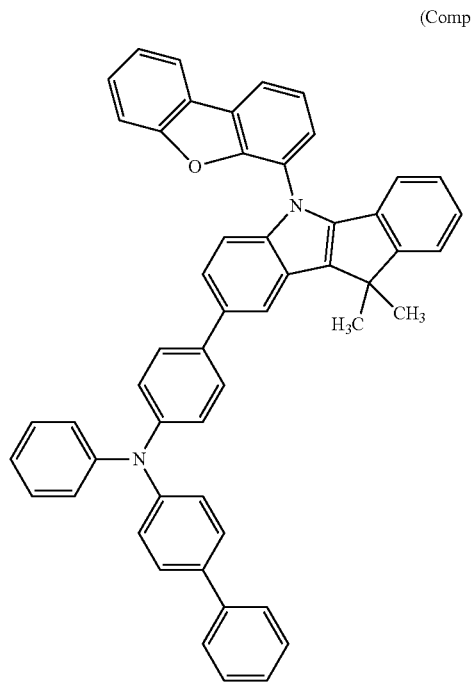
A = benzene
Formulas (1-1), (1-2), (1-3)
(Compound 21)
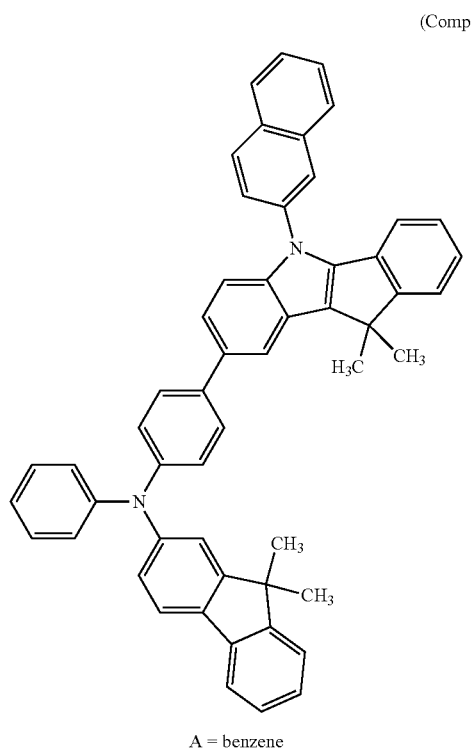
A = benzene
Formulas (1-1), (1-2), (1-3)
(Compound 22)
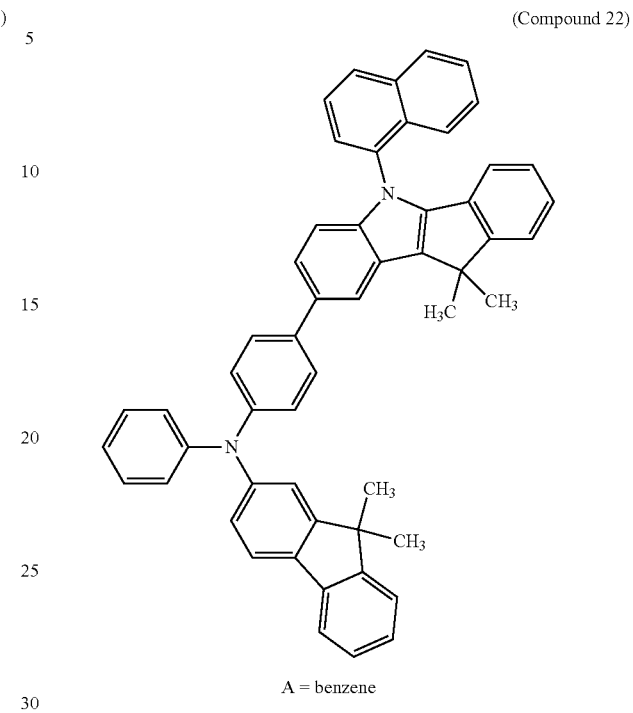
A = benzene
Formulas (1-1), (1-2), (1-3)
(Compound 23)
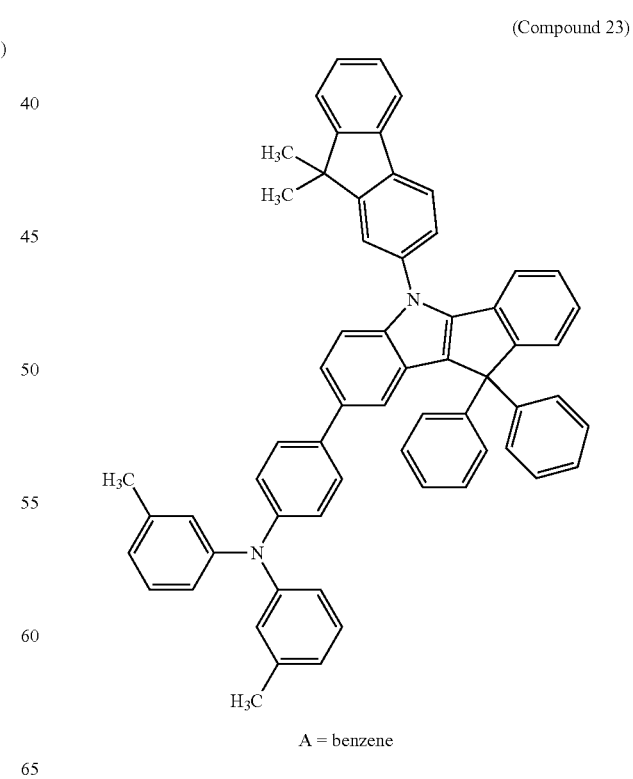
A = benzene Formulas (1-1), (1-2), (1-3)
(Compound 24)
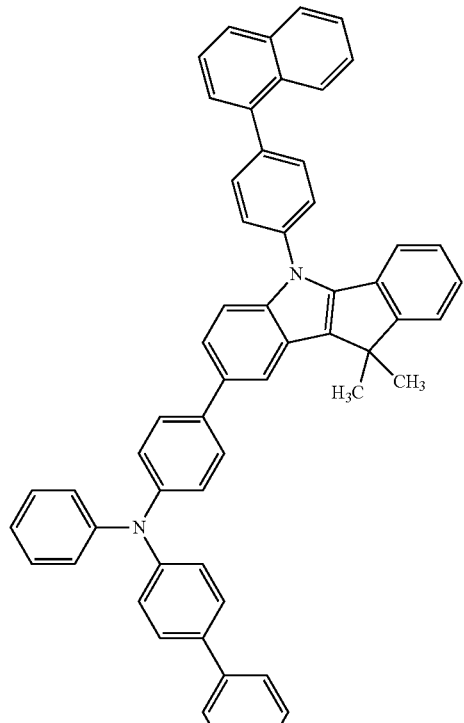
A = benzene
Formulas (1-1), (1-2), (1-3)
(Compound 25)
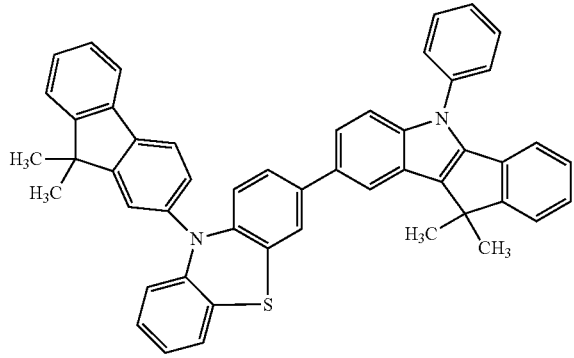
A = benzene
Formulas (1-1), (1-2), (1-3)
(Compound 26)
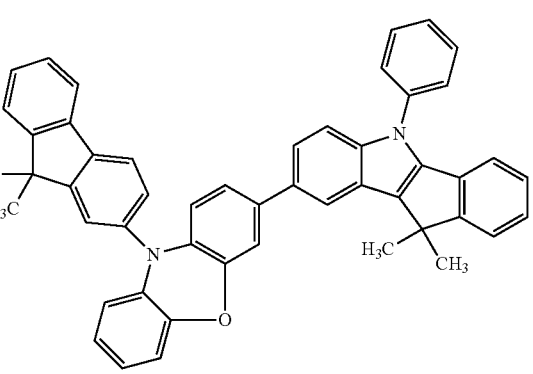
A = benzene
Formulas (1-1), (1-2), (1-3)
(Compound 27)
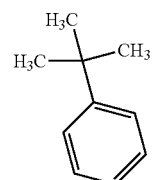
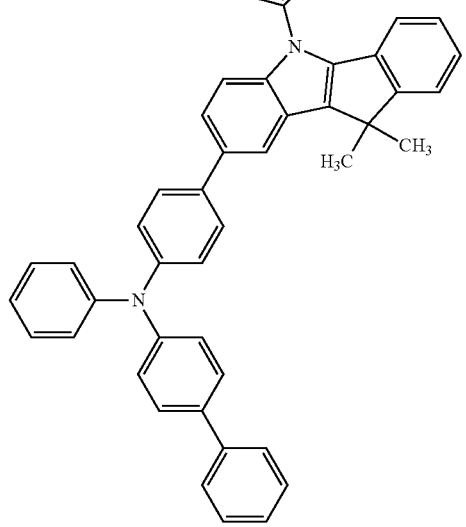
A = benzene Formulas (1-1), (1-2), (1-3)
(Compound 28)
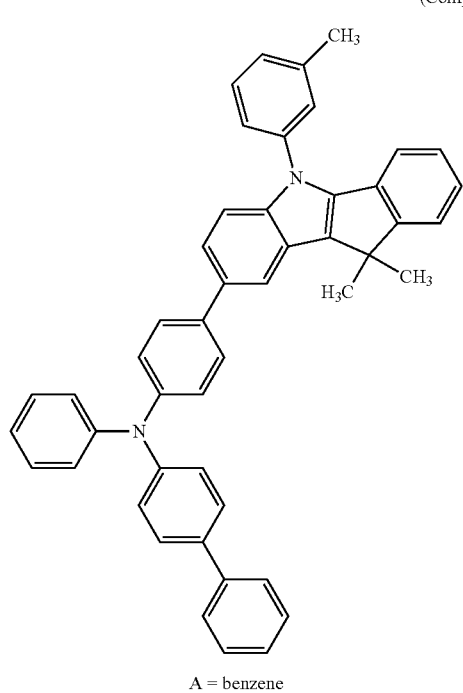
A = benzene
Formulas (1-1), (1-2), (1-3)
(Compound 29)
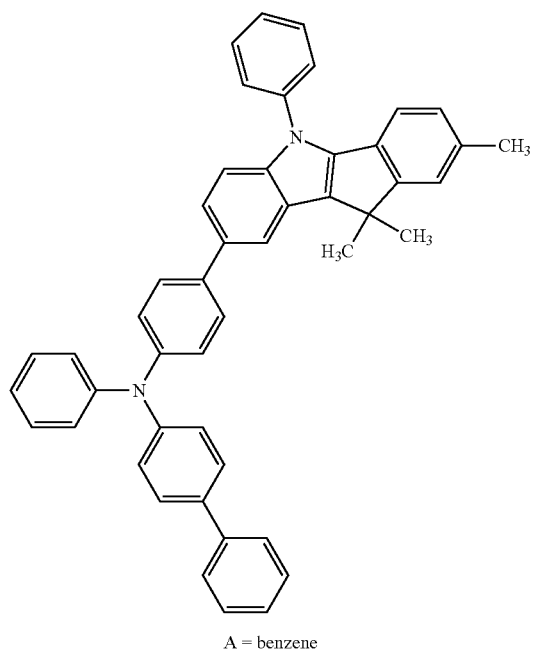
A = benzene
Formula (1)
(Compound 30)
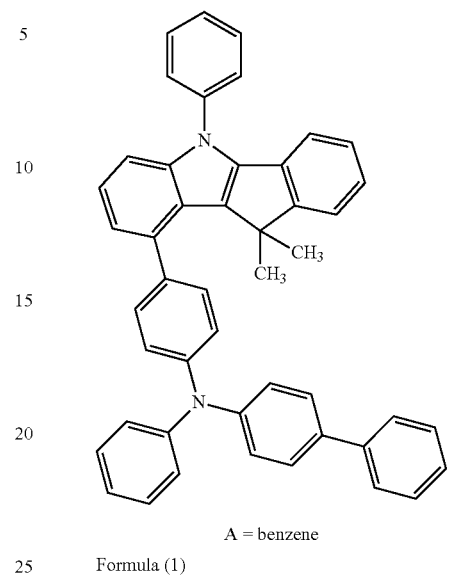
A = benzene
Formula (1)
(Compound 31)
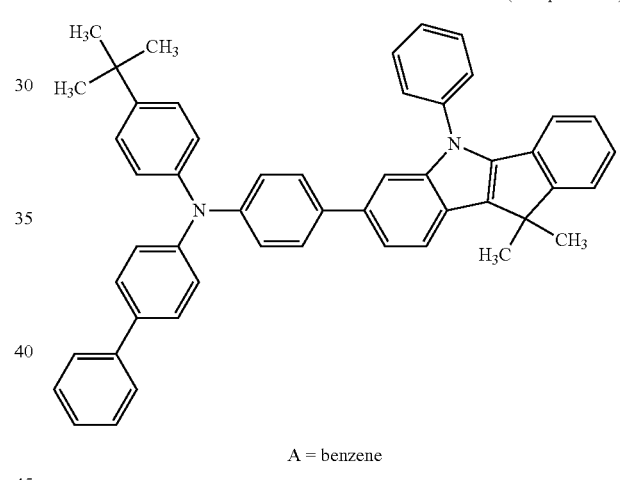
A = benzene
Formula (1-1), (1-2), (1-3)
(Compound 32)
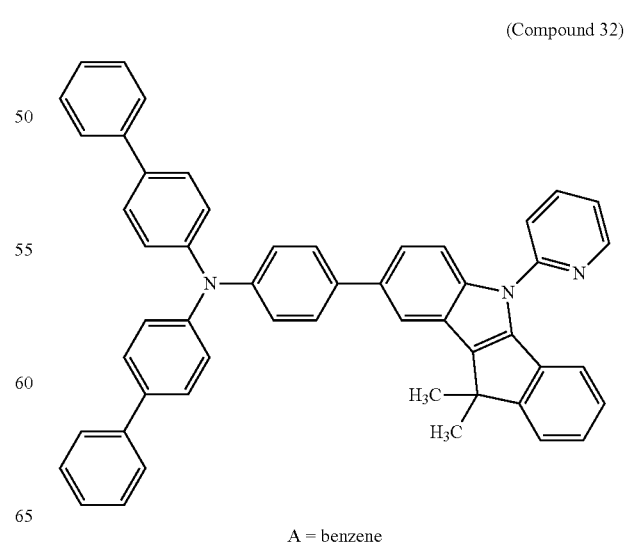
A = benzene Formulas (1-1), (1-2), (1-3) (Compound 33)
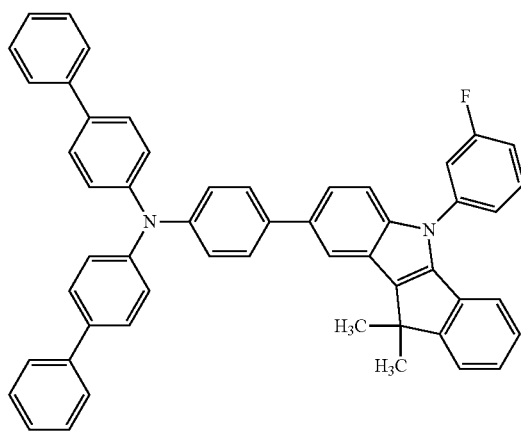
A = benzene
Formulas (1-1), (1-2), (1-3) (Compound 34)
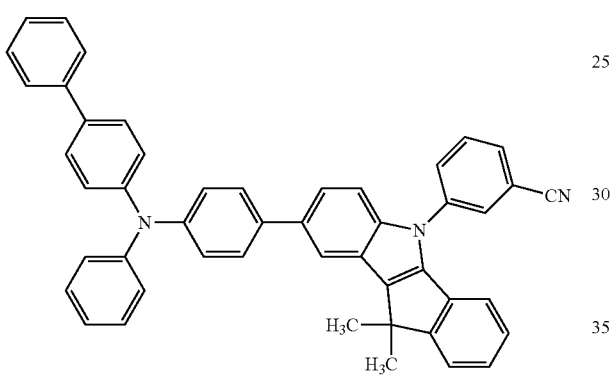
A = benzene
Formulas (1-1), (1-2), (1-3) (Compound 35)
Formulas (1-1), (1-2), (1-3) (Compound 36)
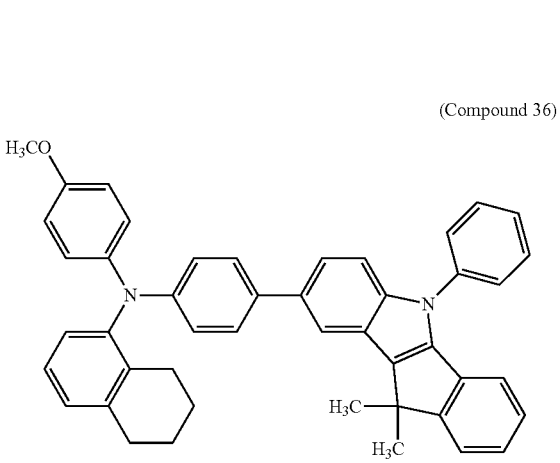
A = benzene
Formula (1) (Compound 37)
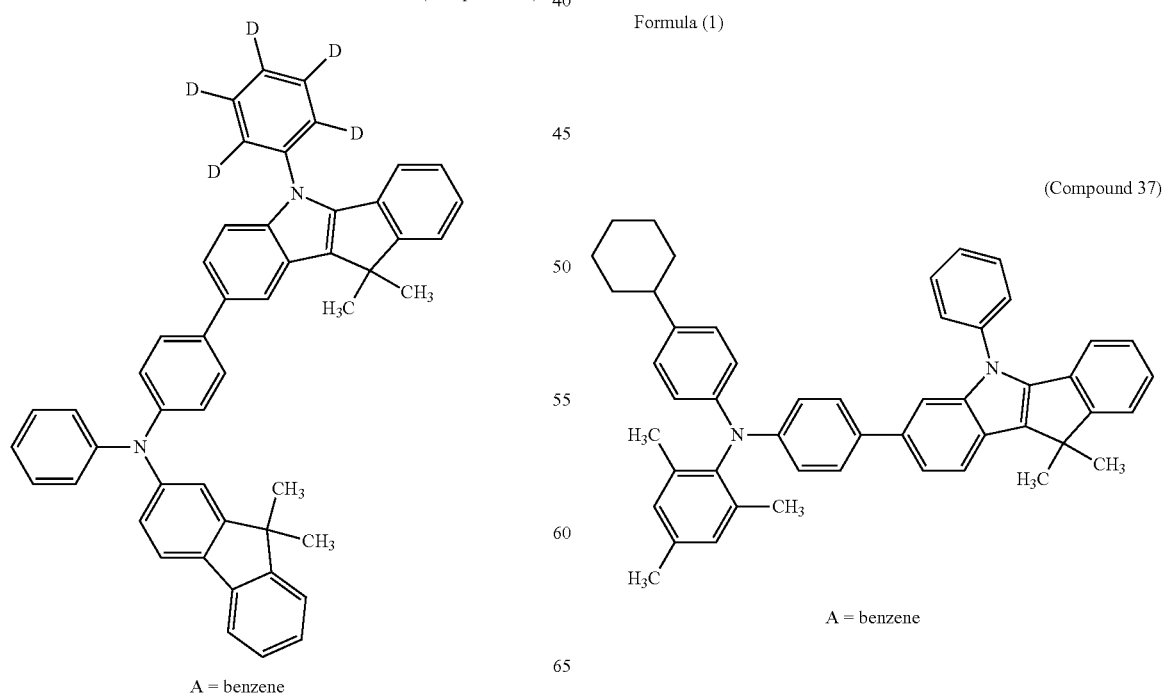
A = benzene Formulas (1-1), (1-2), (1-3)
(Compound 38)
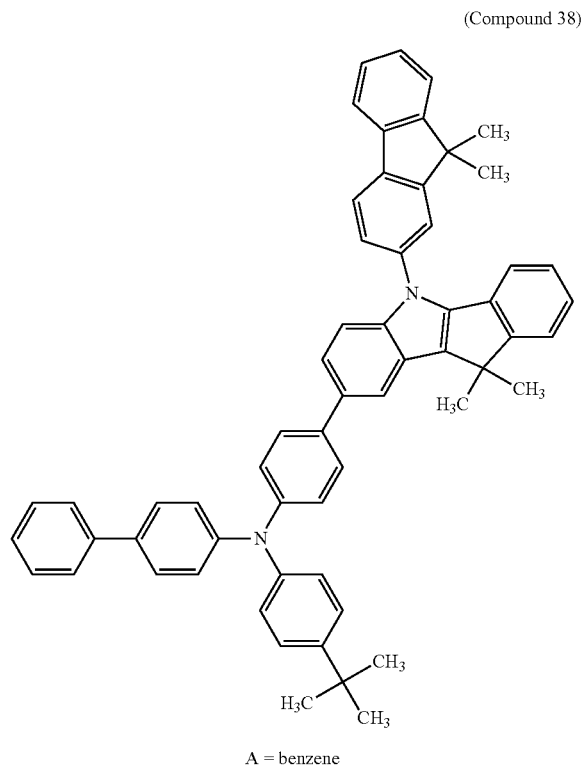
A = benzene
Formulas (1-1), (1-2), (1-3)
(Compound 39)
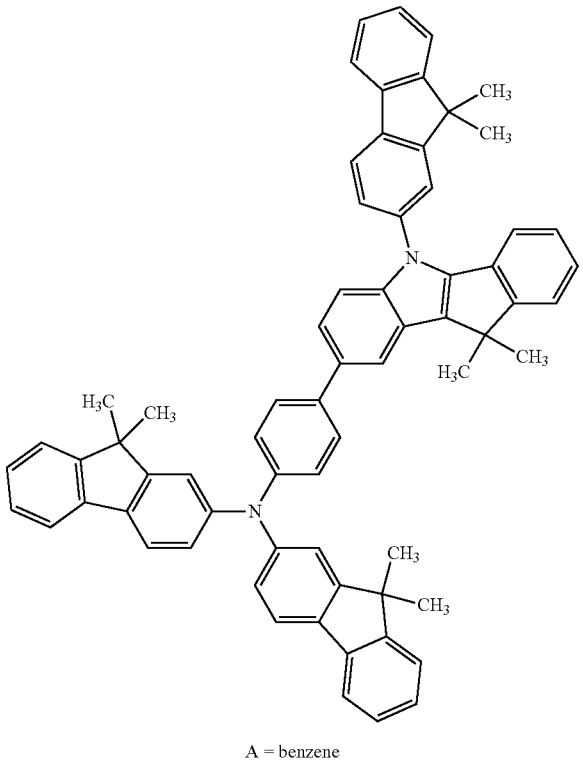
A = benzene
Formulas (1-1), (1-2), (1-3)
(Compound 40)
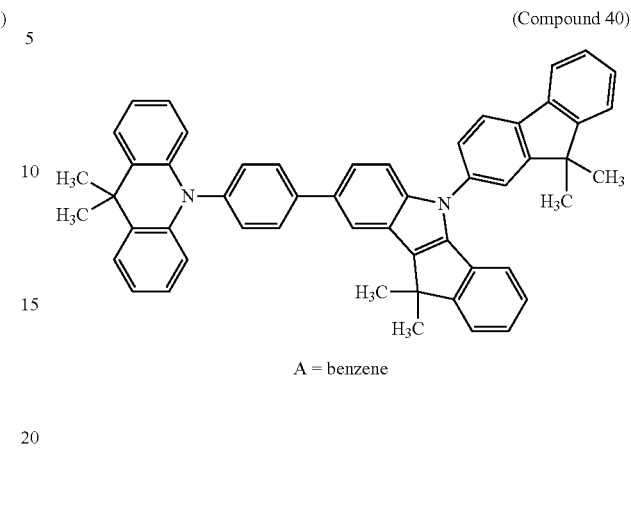
A = benzene
Formulas (1-1), (1-2), (1-3)
(Compound 41)
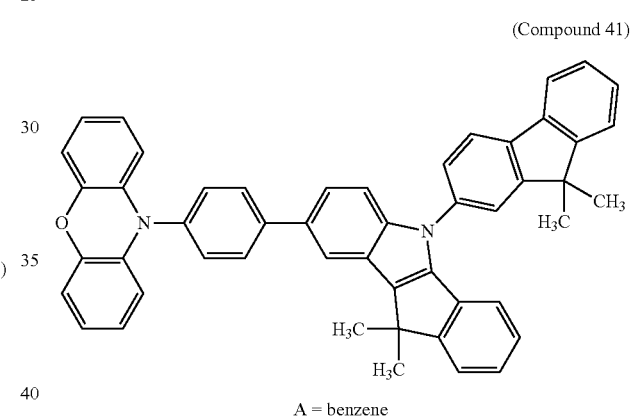
A = benzene
Formulas (1-1), (1-2), (1-3)
(Compound 42)
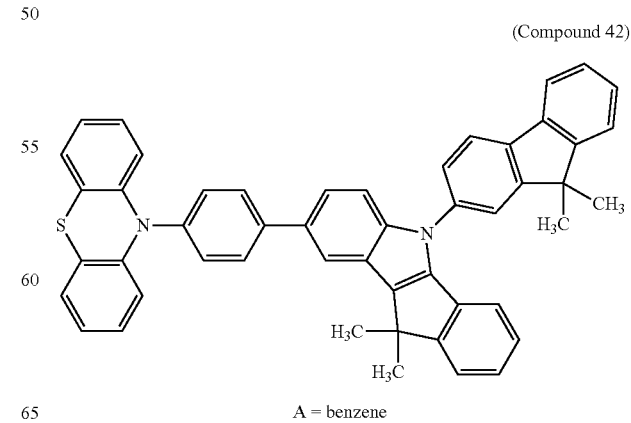
A = benzene Formulas (1-1), (1-2), (1-3)
(Compound 43)
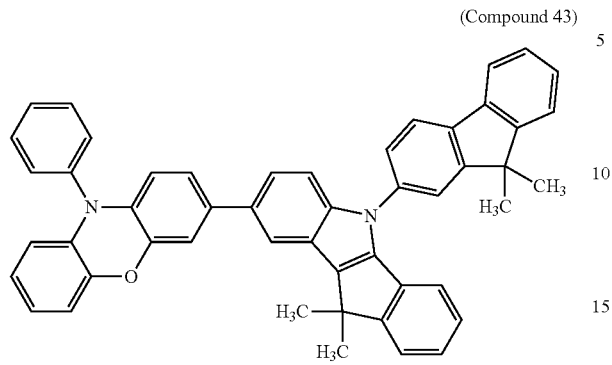
A = benzene
Formulas (1-1), (1-2), (1-3)
(Compound 44)
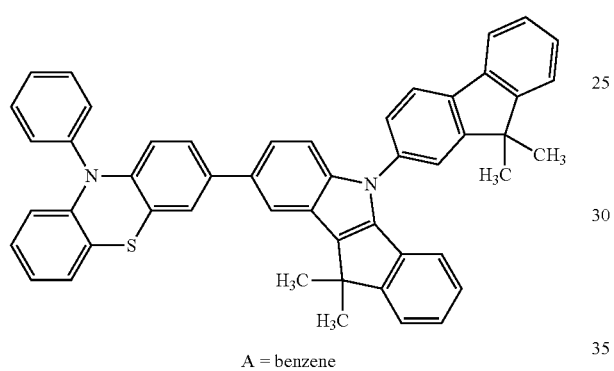
A = benzene
Formulas (1-1), (1-2), (1-3)
(Compound 45)
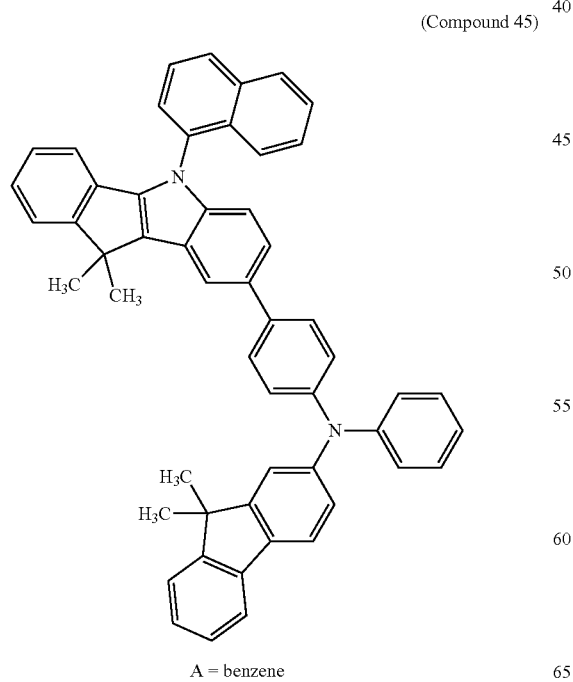
A = benzene
Formulas (1-1), (1-2), (1-3)
(Compound 46)
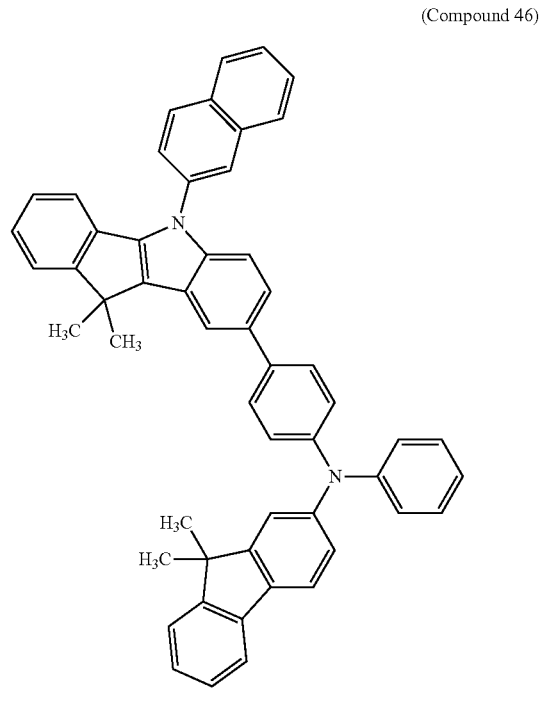
A = benzene
Formulas (1-1), (1-2), (1-3)
(Compound 47)
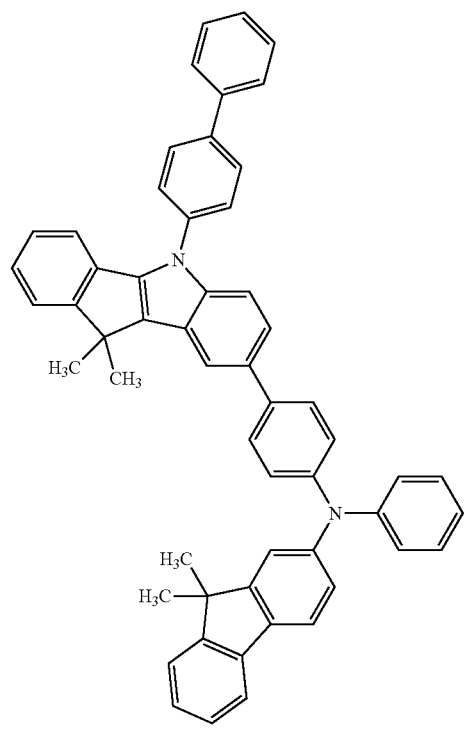
A = benzene Formulas (1-1), (1-4)
(Compound 48)
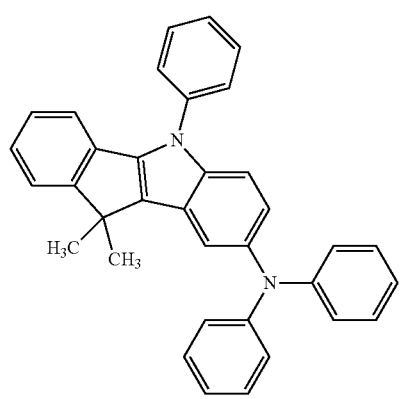
A = Single bond
Formulas (1-1), (1-4)
(Compound 49)
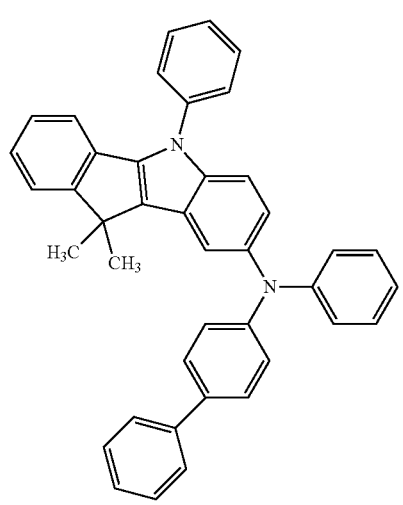
A = Single bond
Formulas (1-1), (1-4)
(Compound 50)
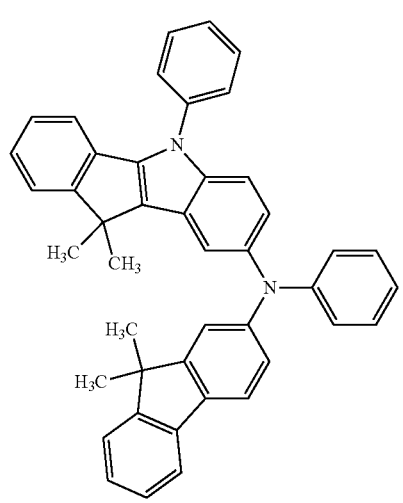
A = Single bond
Formulas (1-1), (1-4)
(Compound 51)
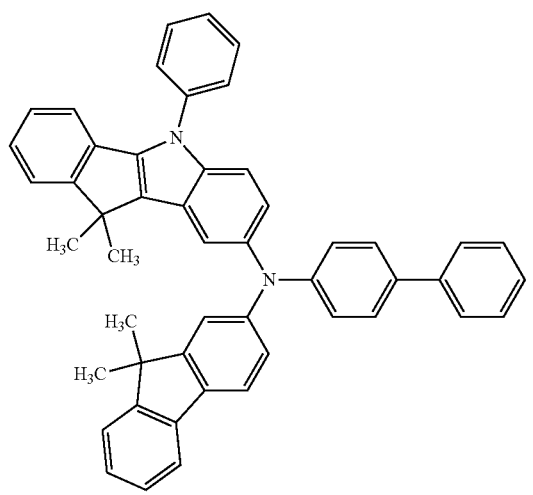
A = Single bond
Formulas (1-1), (1-4)
(Compound 52)
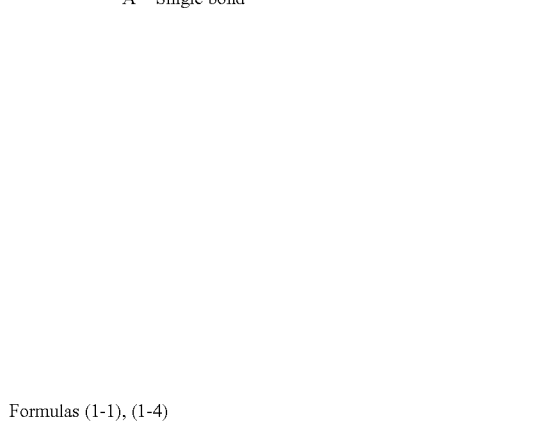
A = Single bond Formulas (1-1), (1-4)
(Compound 53)
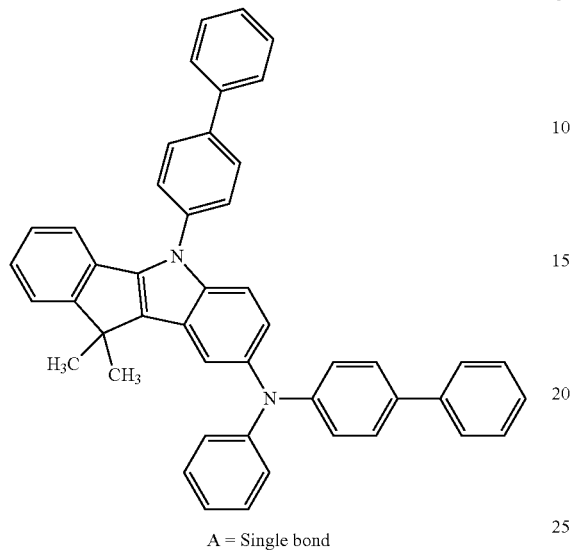
A = Single bond
Formulas (1-1), (1-4)
(Compound 54)
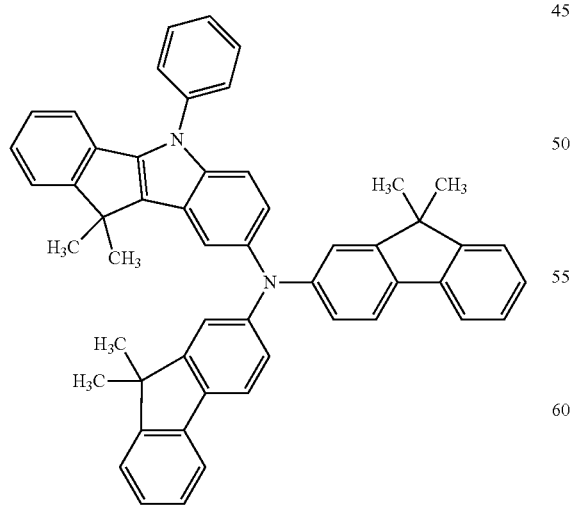
A = Single bond
Formulas (1-1), (1-4)
(Compound 55)
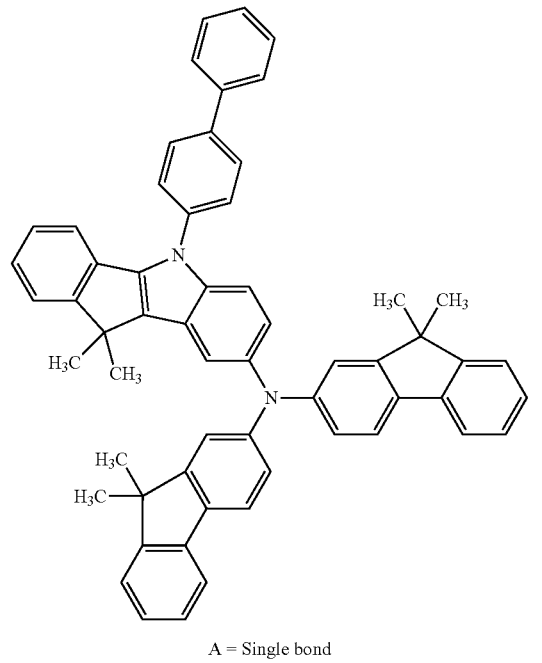
A = Single bond
Formulas (1-1), (1-4)
(Compound 56)
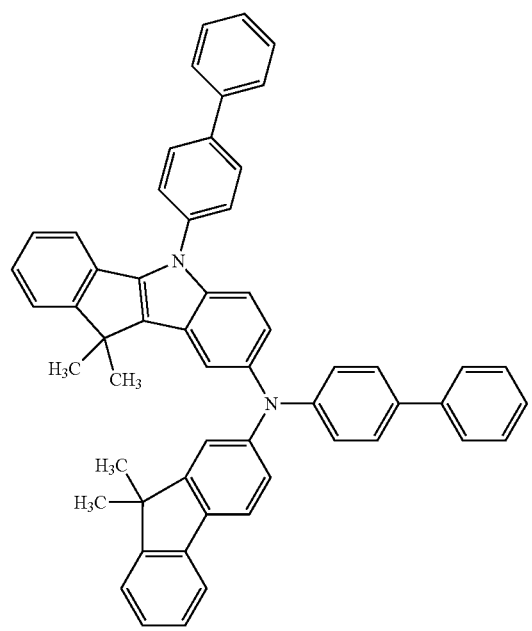
A = Single bond -continued
Formulas (1-1), (1-4)
(Compound 57)
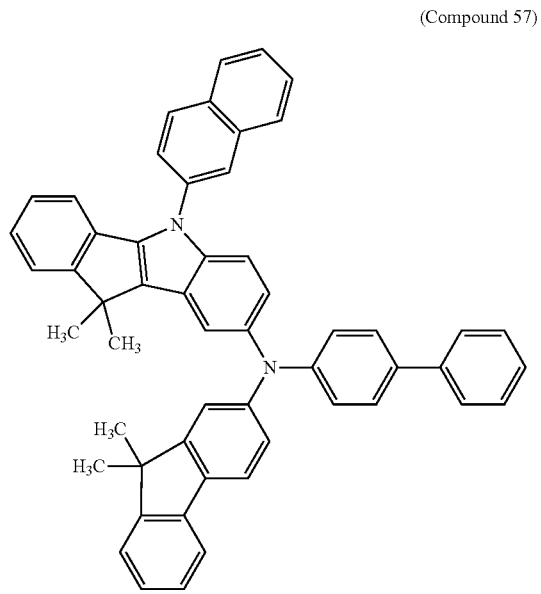
A = Single bond
Formulas (1-1), (1-4)
(Compound 58)
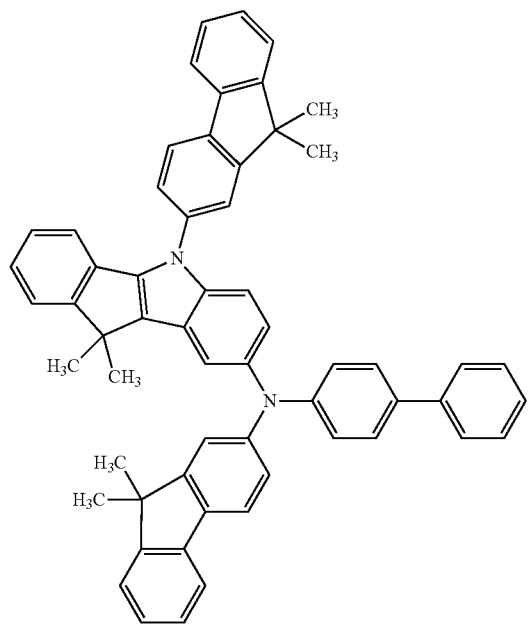
A = Single bond
-continued
Formulas (1-1), (1-4)
(Compound 59)
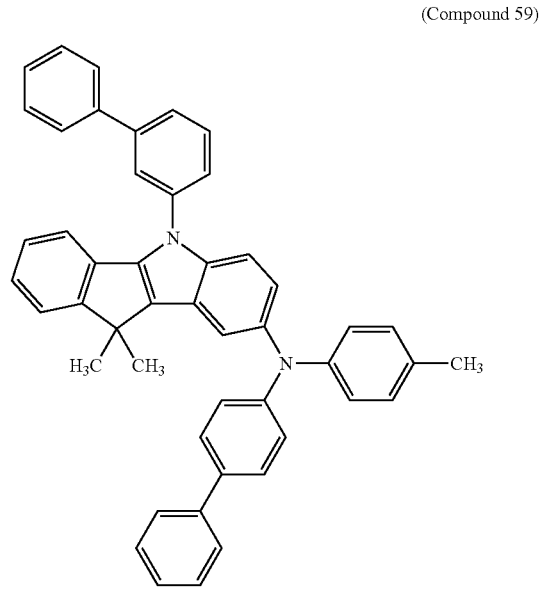
A = Single bond
Formulas (1-1), (1-4)
(Compound 60)
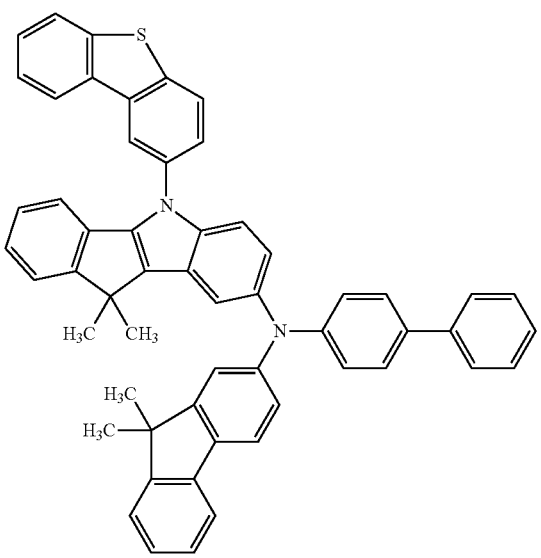
A = Single bond Formulas (1-1), (1-4)
(Compound 61)
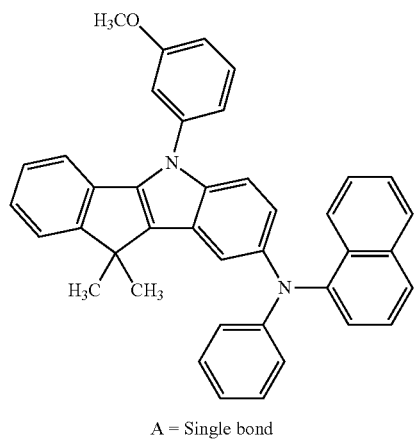
A = Single bond
Formulas (1-1), (1-4)
(Compound 62)
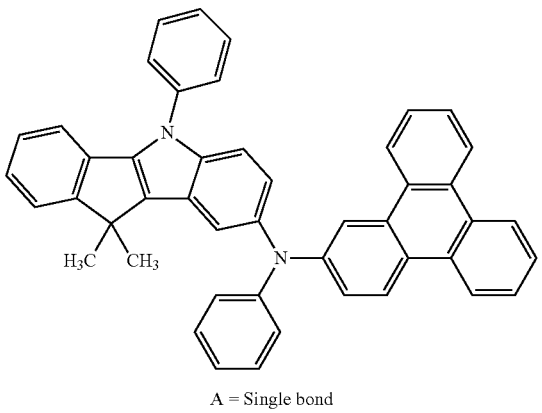
A = Single bond
Formulas (1-1), (1-4)
(Compound 63)
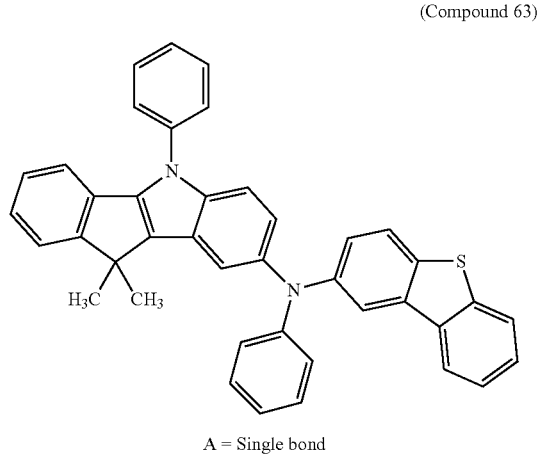
A = Single bond
Formulas (1-1), (1-4)
(Compound 64)
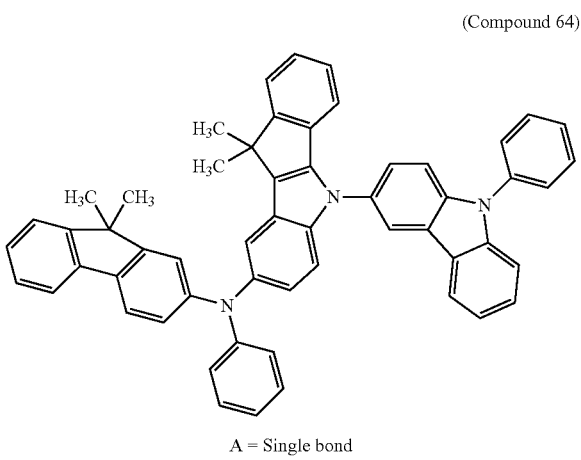
A = Single bond
Formulas (1-1), (1-4)
(Compound 65)
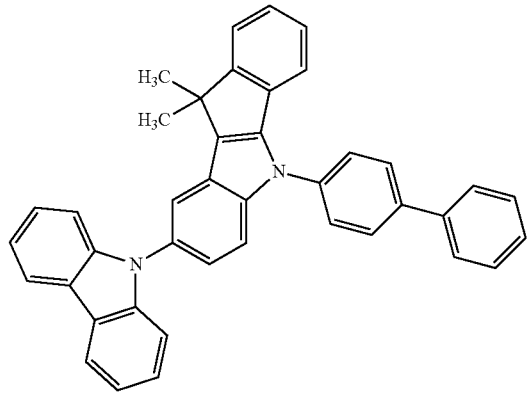
A = Single bond
Formulas (1-1), (1-4)
(Compound 66)
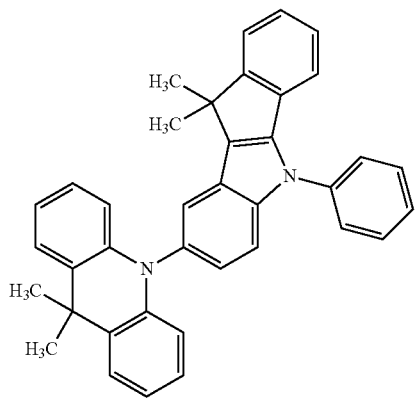
A = Single bond -continued
Formulas (1-1), (1-4)
(Compound 67)
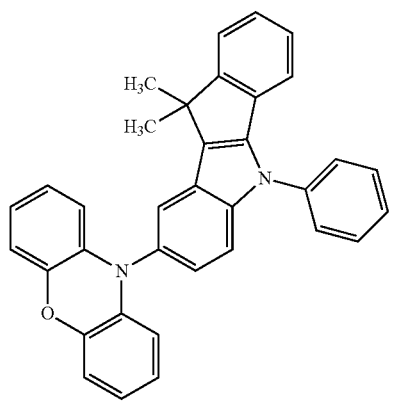
A = Single bond
Formulas (1-1), (1-4)
(Compound 68)
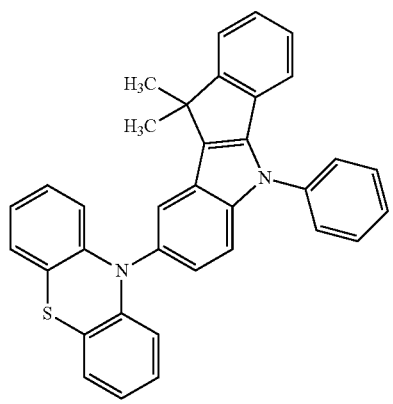
A = Single bond
Formulas (1-1), (1-4)
(Compound 69)
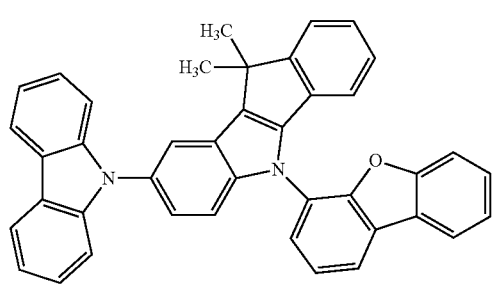
A = Single bond
-continued
Formulas (1-1), (1-4)
(Compound 70)
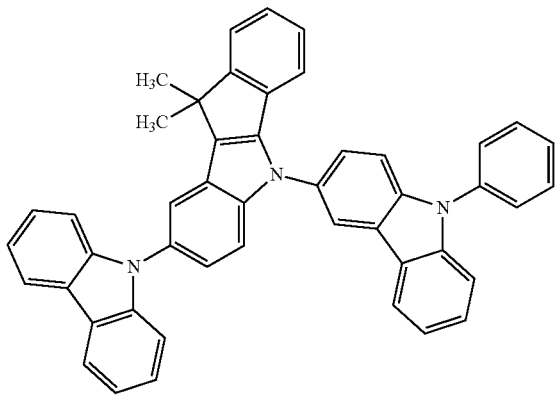
A = Single bond
Formulas (1-1), (1-4)
(Compound 71)
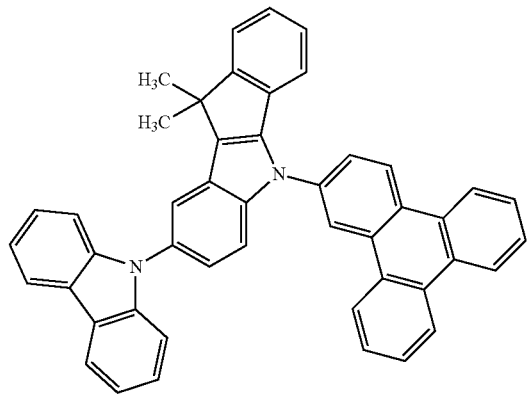
A = Single bond
Formulas (1-1), (1-2), (1-3)
(Compound 72)
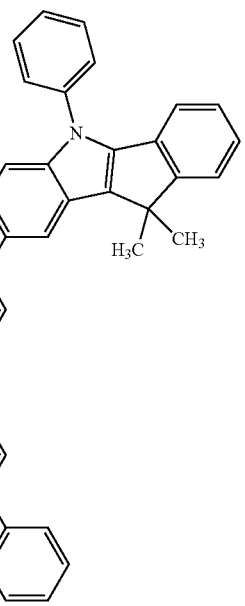
A = benzene Formulas (1-1), (1-2), (1-3)
(Compound 73)
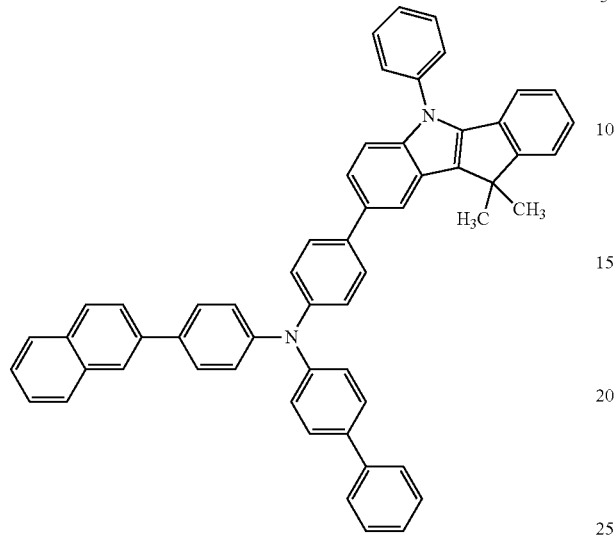
A = benzene
Formulas (1-1), (1-2), (1-3)
(Compound 74)
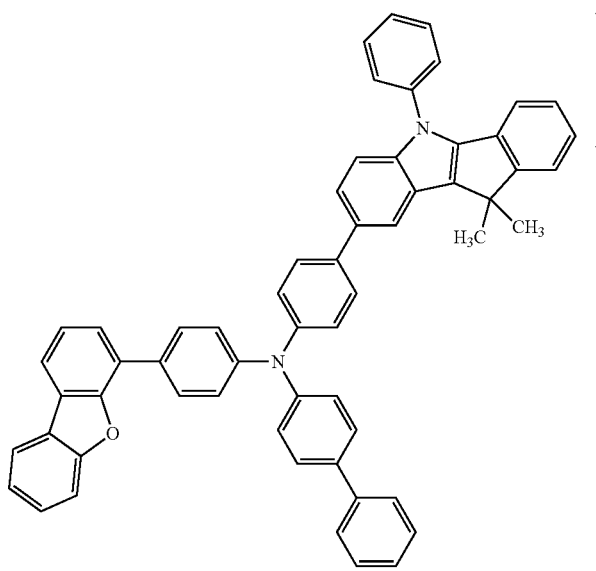
A = benzene
Formulas (1-1), (1-2), (1-3)
(Compound 75)
A = benzene
Formulas (1-1), (1-2), (1-3)
(Compound 76)
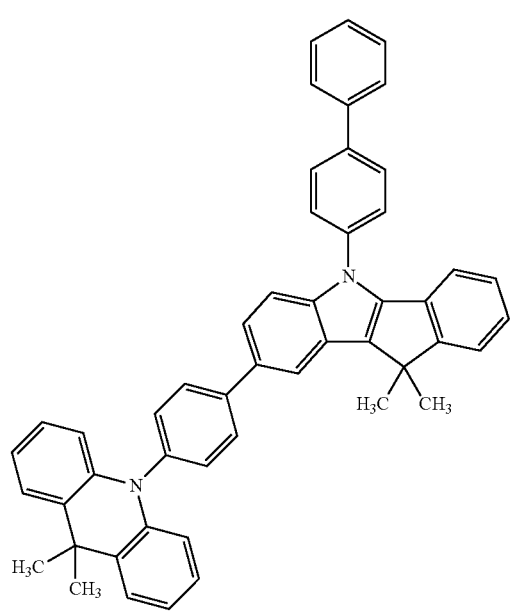
A = benzene Formulas (1-1), (1a), (1a-1)
(Compound 77)
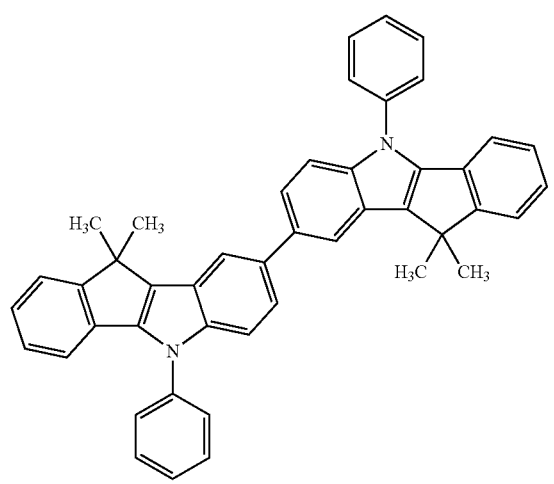
Formulas (1-1), (1-2), (1-3)
(Compound 78)
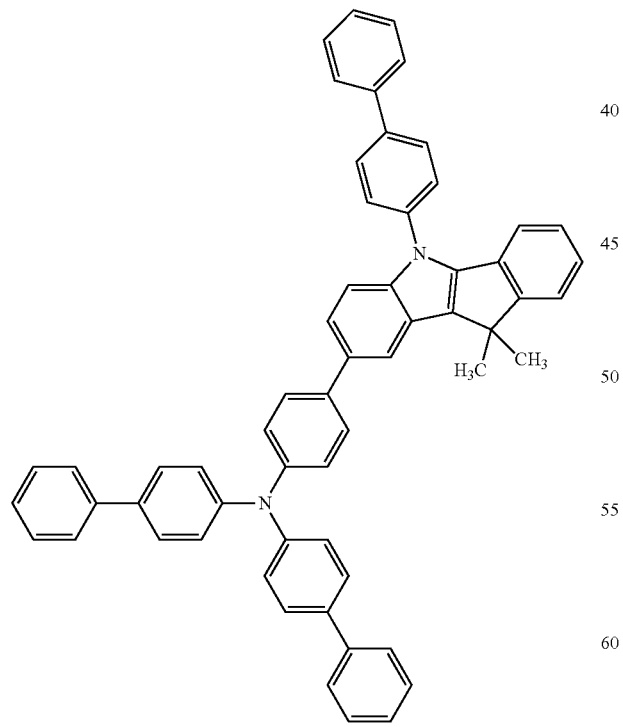
A = benzene
Formulas (1-1), (1-2), (1-3)
(Compound 79)
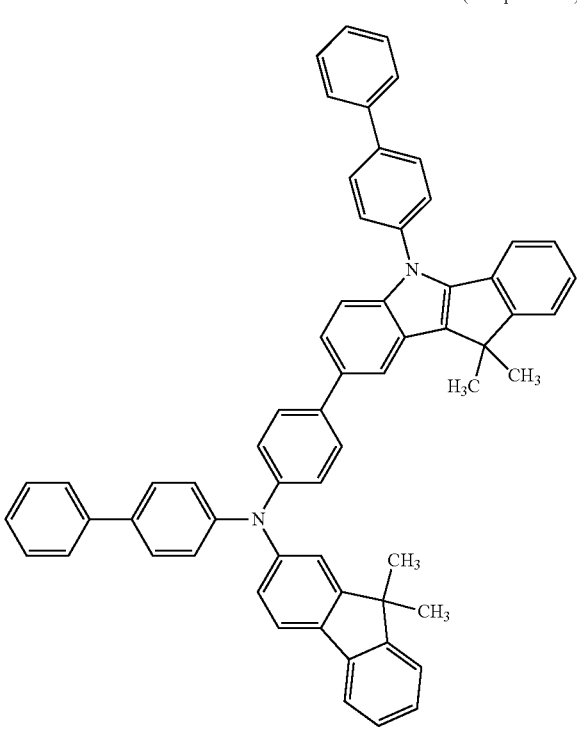
A = benzene
Formula (1-1)
(Compound 80)
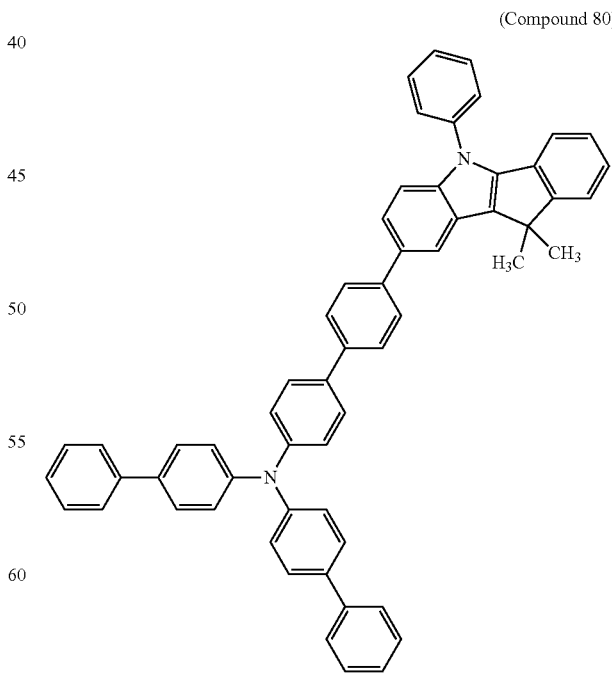
A = Biphenyl Formula (1-1)

(Compound 81)

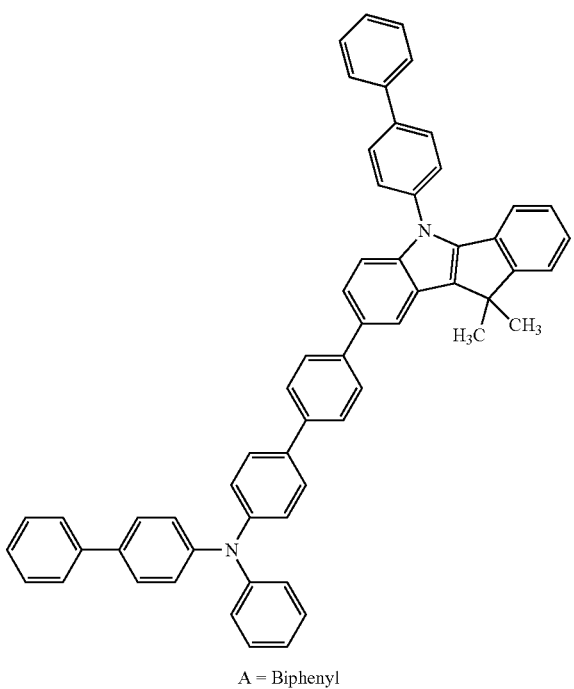

A = Biphenyl

The above-described indenoindole derivative of the present invention has a high glass transition point (Tg) (for example, 100° C. or higher, particularly 120° C. or higher), can form a thin film with excellent heat resistance, and can stably maintain a thin film state because its amorphous state is maintained stably. Further, its hole injection speed is high, its hole moving speed is high, and it shows high electron blocking capability. Thus, if a 100 nm thick vapor-deposited film is formed, for example, using the indenoindole derivative of the present invention, and its work function is measured, the film shows a very high value.

<Organic EL Element>

Figure 22:
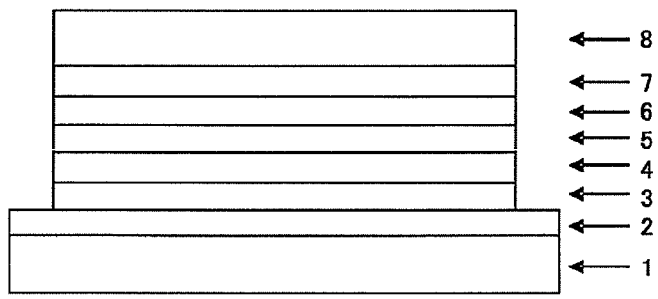
FIG. 22 is a view showing the configuration of the EL elements of Examples 22 to 28 and Comparative Examples 1 to 2.

An organic EL element having organic layers formed using the indenoindole derivative of the present invention described above (may hereinafter be referred to as the organic EL element of the present invention) has a layered structure, for example, as shown in FIG. 22. That is, in the organic EL element of the present invention, for example, a transparent anode 2, a hole injection layer 3, a hole transport layer 4, a light emission layer 5, an electron transport layer 6, an electron injection layer 7, and a cathode 8 are provided in sequence on a substrate 1. The organic EL element of the present invention is not limited to such a layered structure, but for example, may have an electron blocking layer (not shown) between the hole transport layer 4 and the light emission layer 5, or may have a hole blocking layer (not shown) between the light emission layer 5 and the electron transport layer 6. Alternatively, some of the organic layers can be omitted in this multilayer structure. For example, there can be a configuration in which the hole injection layer 3 between the anode 2 and the hole transport layer 4, and the electron injection layer 7 between the electron transport layer 6 and the cathode 8 are omitted, and the anode, the hole transport layer, the light emission layer, the electron transport layer, and the cathode are provided sequentially on the substrate.

The indenoindole derivative of the present invention is preferably used as a material for forming the organic layer provided between the transparent anode 2 and the cathode 8, for example, the hole injection layer 3, the hole transport layer 4, the electron blocking layer (not shown), or the light emission layer 5. Since the indenoindole derivative of the present invention has excellent hole transport properties and electron blocking properties because it has the tertiary amine structure, it is suitable particularly as a material for forming the hole injection layer, the hole transport layer, and the electron blocking layer.

The anode 2 may be composed of an electrode material publicly known per se and, for example, is formed by vacuum-depositing an electrode material having a great work function, such as ITO or gold, on the substrate 1 (a transparent substrate such as a glass substrate).

The hole injection layer 3 can be formed using the indenoindole derivative of the present invention, or a conventionally known material, for example, any of the following materials:

Porphyrin compounds typified by copper phthalocyanine;
Triphenylamine derivatives of starburst type;
Arylamines structured to have a plurality of triphenylamine skeletons coupled together by a single bond or a divalent group containing no hetero-atom (e.g., tetramer of triphenylamine);
Acceptor type heterocyclic compounds such as hexacyanoazatriphenylene; and
Coating type polymeric materials, for example, poly(3,4-ethylenedioxythiophene) (hereinafter abbreviated as PEDOT) and poly(styrenesulfonate) (hereinafter abbreviated as PSS).

The layer (thin film) formed using the above material can be formed by vacuum deposition or any other publicly known method such as a spin coat method or an ink jet method. Various layers to be described below can be similarly formed as films by vapor deposition, spin coating, ink jetting, etc.

The hole transport layer can also be formed using the indenoindole derivative of the present invention, but can be formed using a conventionally known hole transport material. The conventionally known hole transport material can be exemplified by the following:

Benzidine derivatives, for example,
N,N'-diphenyl-N,N'-di(m-tolyl)benzidine (TPD, for short),
N,N'-diphenyl-N,N'-di(α-naphthyl)benzidine (NPD, for short), and
N,N,N',N'-tetrabiphenylylbenzidine;
1,1-bis[4-(di-4-tolylamino)phenyl]cyclohexane (hereinafter abbreviated as TAPC); and
Various triphenylamine trimers and tetramers.

The above materials for use in the formation of the hole transport layer may be used singly for film formation, but can also be used as a mixture of two or more materials for film formation. Alternatively, it is permissible to form a plurality of layers with the use of one or more of the above compounds, and use a multilayer film composed of a stack of such layers as the hole transport layer.

In the present invention, moreover, it is also possible to form a layer serving as the hole injection layer 3 and the hole transport layer 4 concurrently. Such a hole injection/transport layer can be formed using a coating type polymeric material such as poly(3,4-ethylenedioxythiophene) (hereinafter abbreviated as PEDOT)/poly(styrenesulfonate) (hereinafter abbreviated as PSS).

The material usually used for the hole injection layer 3 (like the hole transport layer 4) is further P-doped with trisbromophenylaminium hexachloroantimonate and can be used for the layer, or a polymeric compound having the structure of a benzidine derivative such as TPD in its partial structure can also be used for the layer.

The electron blocking layer (not shown) can be formed using the indenoindole derivative of the present invention, but can also be formed using a conventionally known electron blocking compound. The conventionally known electron blocking compound can be exemplified by the following:

Carbazole derivatives, for example,
4,4',4''-tri(N-carbazolyl)triphenylamine (hereinafter abbreviated as TCTA),
9,9-bis[4-(carbazol-9-yl)phenyl]fluorene,
1,3-bis(carbazol-9-yl)benzene (hereinafter abbreviated as mCP), and
2,2-bis(4-carbazol-9-ylphenyl)adamantane (hereinafter abbreviated as Ad-Cz); and Compounds having a triphenylsilyl group and a triarylamine structure, for example,
9-[4-(carbazol-9-yl)phenyl]-9-[4-(triphenylsilyl)phenyl]-9H-fluorene.

The electron blocking layer can be formed using one of the indenoindole derivative of the present invention and the publicly known materials individually, or using two or more of them. Alternatively, it is permissible to form a plurality of layers with the use of one or more of the above materials, and use a multilayer film composed of a stack of such layers as the electron blocking layer.

The light emission layer 5 can be formed, for example, using the following luminescent materials:

Metal complexes of quinolinol derivatives including $Alq_3$;
Various metal complexes;
Anthracene derivatives;
Bisstyrylbenzene derivatives;
Pyrene derivatives;
Oxazole derivatives; and
Polyparaphenylenevinylene derivatives.

The light emission layer may be composed of a host material and a dopant material.

As the host material, thiazole derivatives, benzimidazole derivatives, and polydialkylfluorene derivatives can be used in addition to the indenoindole derivative of the present invention and the above luminescent materials.

Usable as the dopant material are, for example, quinacridone, coumarin, rubrene, perylene and derivatives thereof; benzopyran derivatives; rhodamine derivatives; and aminostyryl derivatives.

The light emission layer 5 can also be formed using one or more of the luminescent materials. The light emission layer 5 can be in a single-layer configuration, or have a multilayer structure composed of a plurality of layers stacked.

Furthermore, a phosphorescence emitting substance can be used as the luminescent material. As the phosphorescence emitting substance, a phosphorescence emitting substance in the form of a metal complex containing iridium, platinum or the like can be used. Concretely, a green phosphorescence emitting substance such as $Ir(ppy)_3$; a blue phosphorescence emitting substance such as Flrpic or Flr6; or a red phosphorescence emitting substance such as $Btp_2Ir(acac)$ is used. Any of these phosphorescence emitting substances can be used as a dopant for a hole injecting/transporting host material or an electron transporting host material. As the hole injecting/transporting host material, the indenoindole derivative of the present invention can be used in addition to the following:

carbazole derivatives, for example,
4,4'-di(N-carbazolyl)biphenyl (hereinafter abbreviated as CBP);
TCTA; and
mCP.

As the electron transporting host material, the following materials, for example, can be used:
p-bis(triphenylsilyl)benzene (hereinafter abbreviated as UGH2); and
2,2',2''-(1,3,5-phenylene)-tris(1-phenyl-1H-benzimidazole) (hereinafter abbreviated as TPBI).

By using any such material, a high performance organic EL element can be prepared.

Doping of the host material with the phosphorescent light emitting material is preferably performed by codeposition in a range of 1 to 30% by weight based on the entire light emission layer in order to avoid concentration quenching.

Also, a material which emits delayed fluorescence, such as a CDCB derivative, for example, PIC-TRZ, CC2TA, PXZ-TRZ, or 4CzIPN, can be used as the luminescent material.

The hole blocking layer (not shown), which can be provided between the light emission layer 5 and the electron transport layer 6, can be formed using a compound having a hole blocking action, the compound publicly known per se. Such a publicly known compound having the hole blocking action can be exemplified by the following:

Phenanthroline derivatives, for example, bathocuproine (hereinafter abbreviated as BCP);
Metal complexes of quinolinol derivatives, for example, aluminum(III)bis(2-methyl-8-quinolinato)-4-phenylphenolate (hereinafter abbreviated as BAlq);
Various rare earth complexes;
Triazole derivatives;
Triazine derivatives; and
Oxadiazole derivatives.

These materials can also be used in the formation of the electron transport layer 6 to be described below.

The hole blocking layer can also have a single-layer structure or a multilayer laminated structure, and each layer is formed using one or more of the above-mentioned compounds having hole blocking action.

The electron transport layer 6 is formed using compounds publicly known per se, for example, metal complexes of quinolinol derivatives including $Alq_3$ and BAlq;
various metal complexes;
triazole derivatives;
triazine derivatives;
oxadiazole derivatives;
thidiazole derivatives;
carbodiimide derivatives;
quinoxaline derivatives;
phenanthroline derivatives; and
silole derivatives.

This electron transport layer 6 can also have a single-layer structure or a multilayer laminated structure, and each layer is formed using one or more of the aforementioned electron transporting compounds.

The electron injection layer 7 can also be formed using compounds publicly known per se, for example,
alkali metal salts such as lithium fluoride and cesium fluoride;
alkaline earth metal salts such as magnesium fluoride; and
metal oxides such as aluminum oxide.

In selecting the electron transport layer and the cathode suitably, the electron injection layer can be omitted.

In connection with the cathode 8, an electrode material with a low work function such as aluminum is used, or an alloy having a lower work function, such as a magnesium-silver alloy, a magnesium-indium alloy, or an aluminum-magnesium alloy is used as an electrode material.

Embodiments of the present invention will be described more concretely by way of Examples, but the present invention is not limited to the following Examples.

Example 1 (Synthesis of Compound 10)

Synthesis of (biphenyl-4-yl)-(9,9-dimethyl-9H-fluoren-2-yl)-{4-(5-phenyl-10,10-dimethyl-5,10-dihydroindeno[1,2-b]indol-3-yl)phenyl}amine (Compound 10)

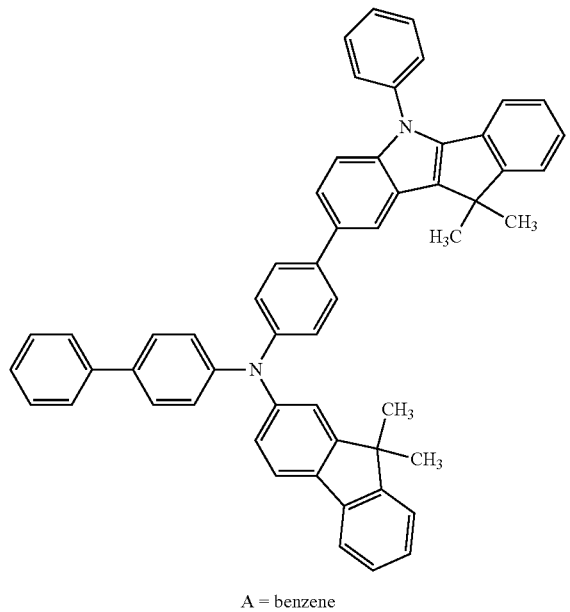

A = benzene
Formulas (1-1), (1-2), (1-3)

| A nitrogen-purged reaction vessel was charged with 10,10-dimethyl-5,10-dihydroindeno[1,2-b]indole | 10.8 g, |
|---|---|
| Iodobenzene | 14.2 g, |
| copper(I) iodide | 0.44 g, |
| tripotassium phosphate | 29.48 g, |
| 1,2-cyclohexanediamine | 15.86 g and |
| 1,4-dioxane | 86 ml. |

The mixture was heated, and refluxed for 24 hours with stirring. The mixture was cooled to room temperature, and insolubles were removed by filtration using Celite as an aid. Then, the filtrate was concentrated to obtain a crude product. The crude product was purified by column chromatography (carrier: silica gel, eluent: dichloromethane/n-heptane), and further recrystallized twice using a dichloromethane/n-heptane solvent mixture to obtain 13.0 g (yield 91%) of 5-phenyl-10,10-dimethyl-5,10-dihydroindeno[1,2-b]indole as a white powder.

| A nitrogen-purged reaction vessel was charged with the resulting 5-phenyl-10,10-dimethyl-5,10-dihydroindeno[1,2-b]indole | 13.1 g, and |
|---|---|
| dimethylformamide | 65 ml. |

The mixture was cooled to 0° C. with stirring. A solution of 7.5 g of N-bromosuccinimide dissolved in 65 ml of dimethylformamide was added dropwise. The mixture was stirred at 0° C. and, after disappearance of the starting materials was confirmed, was added to 1,000 ml of water. A crude product precipitated was collected by filtration, and recrystallization using a dichloromethane/methanol solvent mixture was repeated twice, thereby obtaining 10.3 g (yield 63%) of 3-bromo-5-phenyl-10,10-dimethyl-5,10-dihydroindeno[1,2-b]indole

| A nitrogen-purged reaction vessel was charged with the resulting 3-bromo-5-phenyl-10,10-dimethyl-5,10-dihydroindeno [1,2-b] indole | 10.6 g |
|---|---|
| (biphenyl-4-yl)-(9,9-dimethyl-9H-fluoren-2-yl)-{4-(4,4,5,5-tetramethyl-[1,3,2]dioxaborolan-2-yl)phenyl}amine | 18.5 g |
| tetrakis(triphenylphosphine)palladium | 0.9 g |
| 2M aqueous solution of potassium carbonate | 41 ml, |
| toluene | 74 ml, and |
| ethanol | 19 ml. |

The mixture was heated, and refluxed for 6 hours with stirring. The mixture was cooled to room temperature and, after toluene was added, an organic layer was collected by liquid separation. The organic layer was dehydrated with anhydrous magnesium sulfate, and then concentrated. Methanol was added, and a precipitated crude product was collected by filtration. Recrystallization using a THF/acetone solvent mixture was repeated 3 times on the crude product to obtain 9.6 g (yield 47%) of (biphenyl-4-yl)-(9,9-dimethyl-9H-fluoren-2-yl)-{4-(5-phenyl-10,10-dimethyl-5,10-dihydroindeno[1,2-b]indol-3-yl)phenyl}amine (Compound 10) as a white powder.

In connection with the resulting white powder, its structure was identified using NMR. The results of its $^1$H-NMR measurement are shown in FIG. 1. In $^1$H-NMR (CDCL3), the following signals of 44 hydrogens were detected:

δ (ppm)=7.73 (1H)

7.65-7.12 (30H)

7.02 (1H)

1.68 (6H)

1.45 (6H)

Example 2 (Synthesis of Compound 7)

Synthesis of bis(biphenyl-4-yl)-{4-(5-phenyl-10,10-dimethyl-5,10-dihydroindeno[1,2-b]indol-3-yl)phenyl}amine

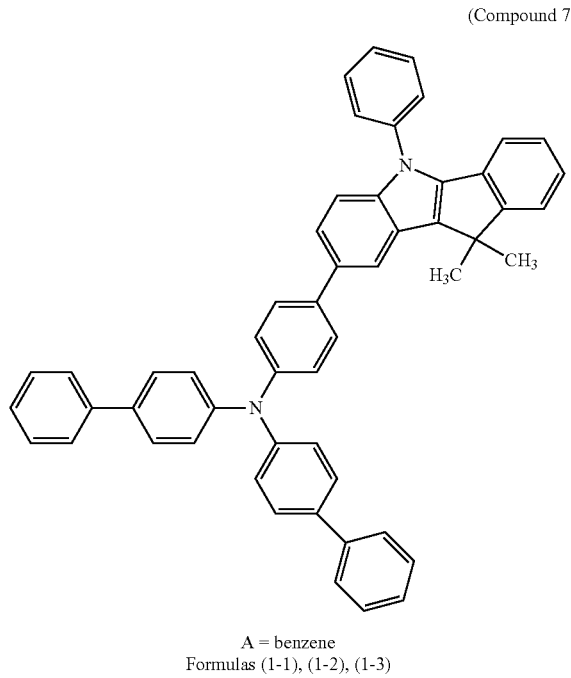 [SMILES: CC1(C)c2ccccc2-c2c1c1cc(-c3ccc(N(c4ccc(-c5ccccc5)cc4)c4ccc(-c5ccccc5)cc4)cc3)ccc1n2-c1ccccc1]

(Compound 7)

A = benzene
Formulas (1-1), (1-2), (1-3)

| | |
|---|---|
| A nitrogen-purged reaction vessel was charged with 3-bromo-5-phenyl-10,10-dimethyl-5,10-dihydroindeno[1,2-b]indole synthesized in Example 1 | 93.4 g, |
| bis(pinacolato)diboron | 91.6 g, |
| PdCl2[dppf] | 9.8 g, |
| potassium acetate | 54.6 g, and |
| toluene | 934 ml. |

The mixture was heated, and refluxed for 7 hours with stirring. After insolubles were removed by hot filtration, the filtrate was concentrated, and purified by column chromatography (carrier: silica gel, eluent: dichloromethane/n-heptane). Then, recrystallization using n-heptane was performed to obtain 53.5 g (yield 51%) of 5-phenyl-10,10-dimethyl-3-(4,4,5,5-tetramethyl-[1,3,2]dioxaborolan-2-yl)-5,10-dihydroindeno [1,2-b]indole as a white powder.

| | |
|---|---|
| A nitrogen-purged reaction vessel was charged with | |
| the resulting 5-phenyl-10,10-dimethyl-3-(4,4,5,5-tetramethyl-[1,3,2]dioxaborolan-2-yl)-5,10-dihydroindeno[1,2-b]indole | 53.5 g, |
| 4-iodobromobenzne | 48.7 g, |
| tetrakis(triphenylphosphine)palladium | 4.3 g |
| 2M aqueous solution of potassium carbonate | 185 ml, |
| toluene | 375 ml, and |
| ethanol | 94 ml. |

The mixture was heated, and refluxed for 10 hours with stirring. The mixture was cooled to room temperature and, after ethyl acetate and water were added, an organic layer was collected by liquid separation. The organic layer was concentrated, and methanol was added. The resulting precipitate was collected by filtration, and then heated and dissolved in toluene, followed by hot filtration to remove insolubles. After the filtrate was concentrated, methanol was added, and a crude product precipitated was collected by filtration. The crude product was subjected to recrystallization using a THF/acetone solvent mixture to obtain 50 g (yield 87%) of 3-(4-bromophenyl)-5-phenyl-10,10-dimethyl-5,10-dihydroindeno[1,2-b]indole as a white powder.

| | |
|---|---|
| A nitrogen-purged reaction vessel was charged with | |
| the resulting 3-(4-bromophenyl)-5-phenyl-10,10-dimethyl-5,10-dihydroindeno[1,2-b]indole | 9.7 g, |
| bis(biphenyl-4-yl)amine | 6.1 g, |
| palladium acetate | 0.1 g |
| tert-butoxysodium | 5.5 g, |
| toluene | 61 ml, and |
| tri(tert-butyl)phosphine | 0.28 g. |

The mixture was heated, and refluxed for 3 hours with stirring. The mixture was cooled to room temperature, and added to 600 ml of methanol. The resulting precipitate was collected by filtration, and then heated and dissolved in toluene, followed by hot filtration to remove insolubles. After the filtrate was concentrated, methanol was added, and a crude product precipitated was collected by filtration. The crude product was recrystallized twice using a THF/acetone solvent mixture to obtain 10.4 g (yield 77%) of bis(biphenyl-4-yl)-(4-(5-phenyl-10,10-dimethyl-5,10-dihydroindeno[1,2-b]indol-3-yl)phenylamine (Compound 7) as a white powder.

Figure 2:
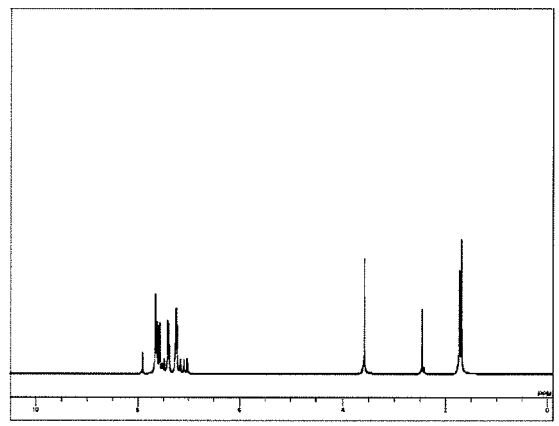
FIG. 2j is a $^1$H-NMR chart diagram of compound of Example 2 (Compound 7).

In connection with the resulting white powder, its structure was identified using NMR. The results of its $^1$H-NMR measurement are shown in FIG. 2. In $^1$H-NMR (THF-$d_8$), the following signals of 40 hydrogens were detected:

δ (ppm)=7.91 (1H)

7.66-7.61 (10H)

7.57 (4H)

7.52 (1H)

7.48 (1H)

7.40 (6H)

7.28-7.23 (8H)

7.17 (1H)

7.09 (1H)

1.69 (6H)

Example 3 (Synthesis of Compound 6)

Synthesis of (biphenyl-4-yl)-phenyl-{4-(5-phenyl-10,10-dimethyl-5,10-dihydroindeno[1,2-b]indol-3-yl)phenyl}amine

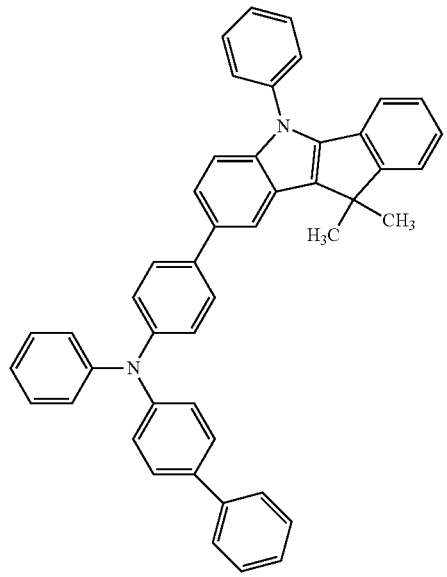

(Compound 6)

A = benzene
Formulas (1-1), (1-2), (1-3)

| | |
|---|---|
| A nitrogen-purged reaction vessel was charged with 3-(4-bromophenyl)-5-phenyl-10,10-dimethyl-5,10-dihydroindeno[1,2-b]indole synthesized in Example 2 | 12.0 g |
| (biphenyl-4-yl)phenylamine | 7.3 g, |
| palladium acetate | 0.2 g |
| tert-butoxysodium | 7.5 g, |
| toluene | 120 ml, and |
| tri(tert-butyl)phosphine | 0.37 g. |

The mixture was heated, and refluxed for 3 hours with stirring. The mixture was cooled to room temperature, and added to 1,000 ml of methanol. The resulting precipitate was collected by filtration, and then heated and dissolved in toluene, followed by hot filtration to remove insolubles. After the filtrate was concentrated, methanol was added, and a crude product precipitated was collected by filtration. The crude product was recrystallized 4 times using a THF/acetone solvent mixture to obtain 7.7 g (yield 47%) of (biphenyl-4-yl)-phenyl-{4-(5-phenyl-10,10-dimethyl-5,10-dihydroindeno[1,2-b]indol-3-yl)pheny}amine (Compound 6) as a white powder.

Figure 3:
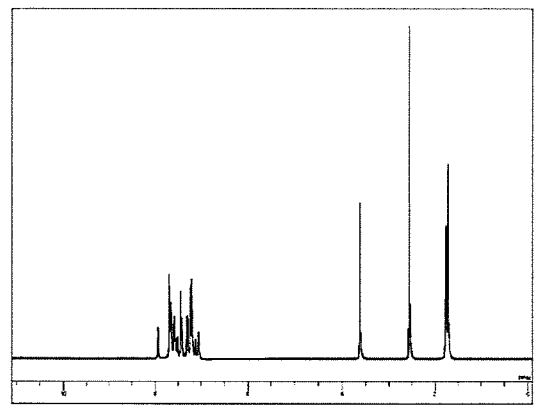
FIG. 3 is a $^1$H-NMR chart diagram of compound of Example 3 (Compound 6).

In connection with the resulting white powder, its structure was identified using NMR. The results of its $^1$H-NMR measurement are shown in FIG. 3. In $^1$H-NMR (THF-$d_8$), the following signals of 36 hydrogens were detected:

δ (ppm)=7.94 (1H)
7.70-7.64 (8H)
7.59 (3H)
7.52 (1H)
7.45 (4H)
7.31 (3H)
7.22 (7H)
7.13 (1H)
7.07 (2H)
1.72 (6H)

Example 4 (Synthesis of Compound 72)

Synthesis of (biphenyl-4-yl)-{4-(naphthalen-1-yl)phenyl}-{4-(5-phenyl-10,10-dimethyl-5,10-dihydroindeno[1,2-b]indol-3-yl)phenyl}amine

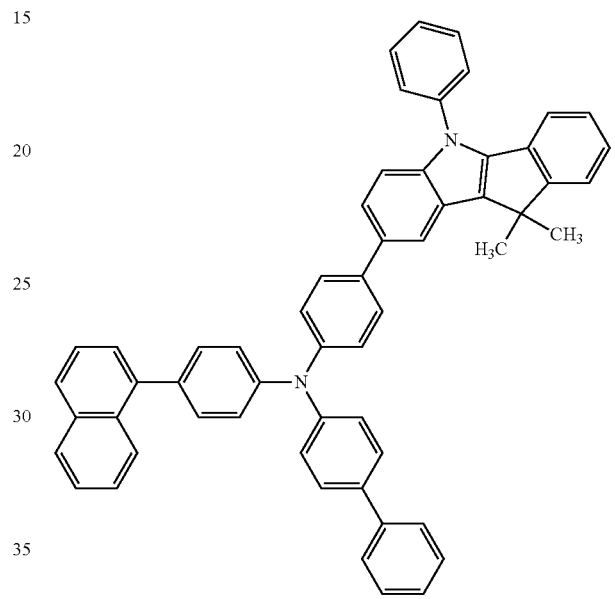

(Compound 72)

A = benzene
Formulas (1-1), (1-2), (1-3)

| | |
|---|---|
| A nitrogen-purged reaction vessel was charged with 3-(4-bromophenyl)-5-phenyl-10,10-dimethyl-5,10-dihydroindeno[1,2-b]indole synthesized in Example 2 | 11.0 g, |
| (biphenyl-4-yl)-{4-(naphthalen-1-yl)phenyl}amine | 10.1 g, |
| palladium acetate | 0.2 g |
| tert-butoxysodium | 6.8 g, |
| toluene | 110 ml, and |
| tri(tert-butyl)phosphine | 0.34 g. |

The mixture was heated, and refluxed for 3 hours with stirring. The mixture was cooled to room temperature, and added to 1,000 ml of methanol. The resulting precipitate was collected by filtration, and then heated and dissolved in toluene, followed by hot filtration to remove insolubles. After the filtrate was concentrated, methanol was added, and a crude product precipitated was collected by filtration. The crude product was recrystallized 3 times using a THF/acetone solvent mixture, and then recrystallized using THF to obtain 10.7 g (yield 60%) of (biphenyl-4-yl)-{4-(naphthalen-1-yl)phenyl}-{4-(5-phenyl-10,10-dimethyl-5,10-dihydroindeno[1,2-b]indol-3-yl)pheny}amine (Compound 72) as a white powder.

Figure 4:
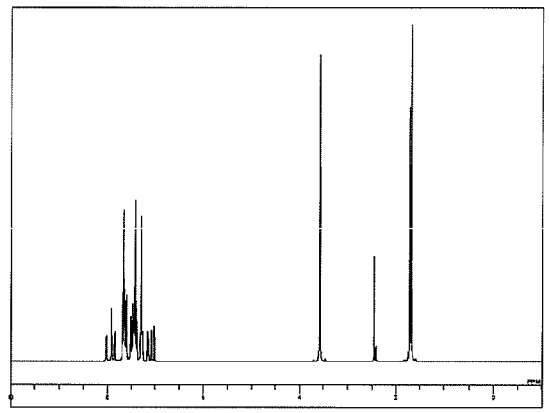
FIG. 4 is a $^1$H-NMR chart diagram of compound of Example 4 (Compound 72).

In connection with the resulting white powder, its structure was identified using NMR. The results of its $^1$H-NMR measurement are shown in FIG. 4. In $^1$H-NMR (THF-$d_8$), the following signals of 42 hydrogens were detected:

δ (ppm)=8.01 (1H)
7.91 (2H)
7.84 (1H)
7.68-7.59 (10H)
7.51-7.40 (12H)
7.30 (7H)
7.16 (1H)
7.09 (1H)
7.02 (1H)
1.69 (6H)

Example 5 (Synthesis of Compound 73)

Synthesis of (biphenyl-4-yl)-{4-(naphthalen-2-yl)phenyl}-{4-(5-phenyl-10,10-dimethyl-5,10-dihydroindeno[1,2-b]indol-3-yl)phenyl}amine (Compound 73)

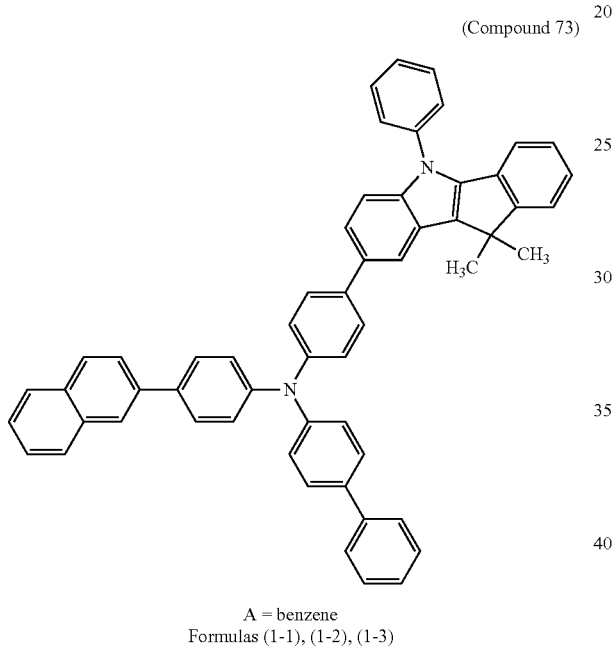

A = benzene
Formulas (1-1), (1-2), (1-3)

| | |
|---|---|
| A nitrogen-purged reaction vessel was charged with 3-(4-bromophenyl)-5-phenyl-10,10-dimethyl-5,10-dihydroindeno[1,2-b]indole synthesized in Example 2 | 10.0 g, |
| (biphenyl-4-yl)-{4-(naphthalen-2-yl)phenyl}amine | 9.2 g, |
| palladium acetate | 0.1 g |
| tert-butoxysodium | 6.2 g, |
| toluene | 100 ml, and |
| tri(tert-butyl)phosphine | 0.31 g. |

The mixture was heated, and refluxed for 3 hours with stirring. The mixture was cooled to room temperature, and added to 1,000 ml of methanol. The resulting precipitate was collected by filtration, and then heated and dissolved in toluene, followed by hot filtration to remove insolubles. After the filtrate was concentrated, the concentrate was purified by column chromatography (carrier: silica gel, eluent: dichloromethane/n-heptane). Then, recrystallization using methanol was repeated 3 times to obtain 12.6 g (yield 77%) (biphenyl-4-yl)-{4-(naphthalen-2-yl)phenyl}-{4-(5-phenyl-10,10-dimethyl-5,10-dihydroindeno[1,2-b]indol-3-yl)pheny}amine (Compound 73) as a white powder.

Figure 5:
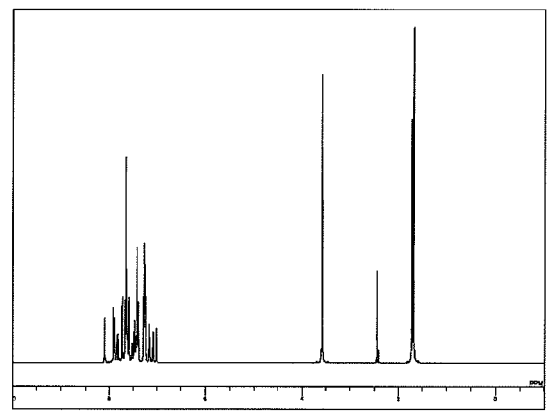
FIG. 5 is a $^1$H-NMR chart diagram of compound of Example 5 (Compound 73).

In connection with the resulting white powder, its structure was identified using NMR. The results of its $^1$H-NMR measurement are shown in FIG. 5. In $^1$H-NMR (THF-$d_8$), the following signals of 42 hydrogens were detected:
δ (ppm)=8.11 (1H)
7.90 (3H)
7.84 (1H)
7.81 (1H)
7.73 (2H)
7.65 (8H)
7.59 (2H)
7.50 (1H)
7.48-7.38 (7H)
7.27 (7H)
7.25 (1H)
7.09 (1H)
7.03 (1H)
1.69 (6H)

Example 6 (Synthesis of Compound 74)

Synthesis of (biphenyl-4-yl)-{4-(dibenzofuran-4-yl)phenyl}-{4-(5-phenyl-10,10-dimethyl-5,10-dihydroindeno[1,2-b]indol-3-yl)phenyl}amine (Compound 74)

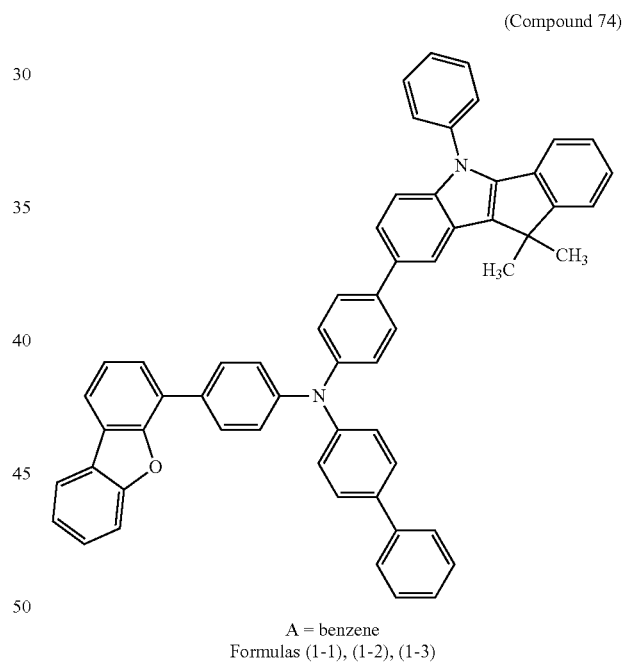

A = benzene
Formulas (1-1), (1-2), (1-3)

| | |
|---|---|
| A nitrogen-purged reaction vessel was charged with 3-(4-bromophenyl)-5-phenyl-10,10-dimethyl-5,10-dihydroindeno[1,2-b]indole synthesized in Example 2 | 10.0 g, |
| (biphenyl-4-yl)-{4-(dibenzofuran-4-yl)phenyl}amine | 10.2 g, |
| palladium acetate | 0.1 g |
| tert-butoxysodium | 6.2 g, |
| toluene | 100 ml, and |
| tri(tert-butyl)phosphine | 0.31 g. |

The mixture was heated, and refluxed for 3 hours with stirring. The mixture was cooled to room temperature, and added to 1,000 ml of methanol. The resulting precipitate was collected by filtration, and then heated and dissolved in toluene, followed by hot filtration to remove insolubles. After the filtrate was concentrated, methanol was added, and a crude product precipitated was recrystallized twice using a chlorobenzene/acetone solvent mixture, and then recrystallized twice using chlorobenzene to obtain 9.1 g (yield 54%) of (biphenyl-4-yl)-{4-(dibenzofuran-4-yl)phenyl}-{4-(5-phenyl-10,10-dimethyl-5,10-dihydroindeno[1,2-b]indol-3-yl)pheny}amine (Compound 74) as a white powder.

Figure 6:
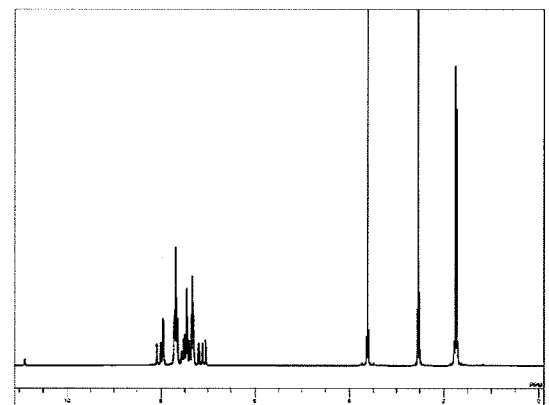
FIG. 6 is a $^1$H-NMR chart diagram of compound of Example 6 (Compound 74).

In connection with the resulting white powder, its structure was identified using NMR. The results of its $^1$H-NMR measurement are shown in FIG. 6. In $^1$H-NMR (THF-d$_8$), the following signals of 42 hydrogens were detected:

δ (ppm)=8.06 (1H)

7.98 (1H)

7.93 (3H)

7.65 (12H)

7.53 (1H)

7.49 (2H)

7.43 (5H)

7.36 (1H)

7.31 (7H)

7.17 (1H)

7.09 (1H)

7.03 (1H)

1.69 (6H)

Example 7 (Synthesis of Compound 75)

Synthesis of 3-{4-(carbazol-9-yl)phenyl}-5-phenyl-10,10-dimethyl-5,10-dihydroindeno[1,2-b]indole

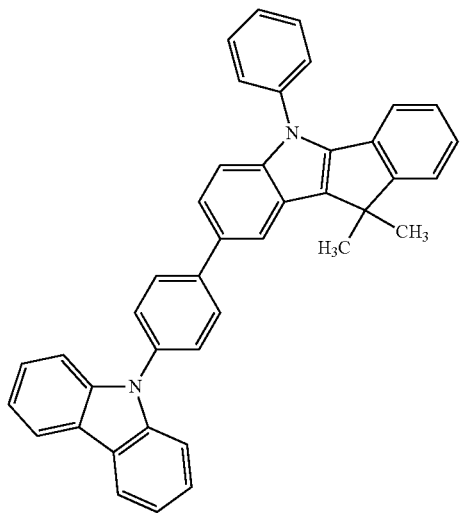

(Compound 75)

A = benzene
Formulas (1-1), (1-2), (1-3)

| | |
|---|---|
| A nitrogen-purged reaction vessel was charged with | 12.0 g, |
| 3-bromo-5-phenyl-10,10-dimethyl-5,10-dihydroindeno[1,2-b]indole synthesized in Example 1 | |
| 9-(4,4,5,5-tetramethyl-[1,3,2]dioxaborolan-2-yl)phenyl-9H-carbazole | 13.7 g, |
| tetrakis(triphenylphosphine)palladium | 1.1 g |
| 2M aqueous solution of potassium carbonate | 46 ml, |
| toluene | 84 ml, and |
| ethanol | 21 ml. |

The mixture was heated, and refluxed for 6 hours with stirring. The mixture was cooled to room temperature and, after ethyl acetate and water were added, an organic layer was collected by liquid separation. The organic layer was concentrated, and methanol was added. The resulting precipitate was collected by filtration, and then heated and dissolved in toluene, followed by hot filtration to remove insolubles. After the filtrate was concentrated, methanol was added, and a crude product precipitated was collected by filtration. The crude product was subjected to recrystallization twice using a dichloromethane/acetone solvent mixture to obtain 6.1 g (yield 36%) of 3-{4-carbazol-9-yl)phenyl}-5-phenyl-10,10-dimethyl-5,10-dihydroindeno[1,2-b]indole (Compound 75) as a white powder.

Figure 7:
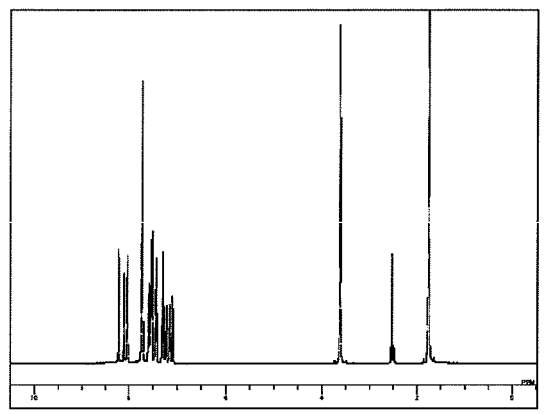
FIG. 7 is a $^1$H-NMR chart diagram of compound of Example 7 (Compound 75).

In connection with the resulting white powder; its structure was identified using NMR. The results of its $^1$H-NMR measurement are shown in FIG. 7. In $^1$H-NMR (THF-d$_8$), the following signals of 30 hydrogens were detected:

δ (ppm)=8.20 (2H)

8.09 (1H)

8.02 (2H)

7.72-7.69 (6H)

7.58 (2H)

7.54-7.50 (4H)

7.42 (2H)

7.28 (2H)

7.22 (1H)

7.14 (1H)

7.08 (1H)

1.76 (6H)

Example 8 (Synthesis of Compound 76)

Synthesis of 3-{4-(9,9-dimethyl-9H-acridin-10-yl)phenyl}-5-(biphenyl-4-yl)-10,10-dimethyl-5,10-dihydroindeno[1,2-b]indole Formulas (1-1), (1-2), (1-3)

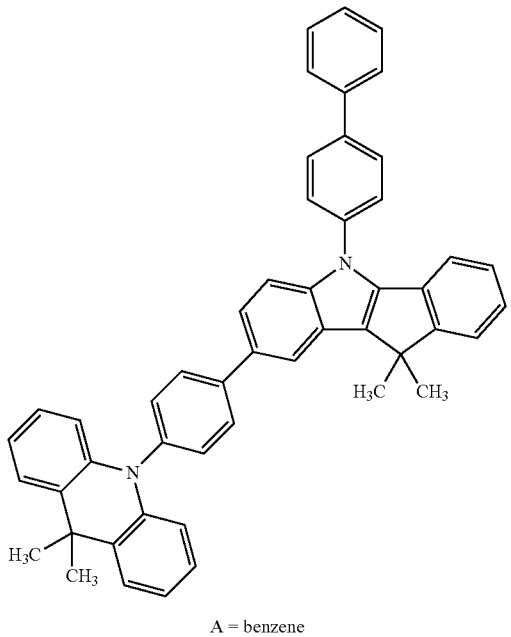

(Compound 76)

A = benzene

| A nitrogen-purged reaction vessel was charged with | 73.9 g, and |
| --- | --- |
| 10,10-dimethyl-5,10-dihydroindeno[1,2-b]indole | |
| dimethylformamide | 740 ml. |

The mixture was cooled to 5° C. with stirring. N-bromosuccinimide (56.3 g) was added in small portions. The mixture was stirred at 5° C. for 2 hours, and ethyl acetate and water were added. An organic layer was collected by liquid separation, and concentrated. The concentrate was purified by column chromatography (carrier: silica gel, eluent: dichloromethane/n-heptane). Then, recrystallization using n-heptane was performed to obtain 71.9 g (yield 73%) of 3-bromo-10,10-dimethyl-5,10-dihydroindeno[1,2-b]indole as a white powder.

| The resulting 3-bromo-10,10-dimethyl-5,10-dihydroindeno[1,2-b]indole | 30 g, |
| --- | --- |
| 4-iodobiphenyl | 40.4 g, |
| copper(I) iodide | 0.92 g, |
| tripotassium phosphate | 61.3 g, |
| 1,2-cyclohexanediamine | 32.9 g, and |
| 1,4-dioxane | 300 ml. |

The mixture was heated, and refluxed for 24 hours with stirring. After the mixture was cooled, toluene was added, and the mixture was heated and dissolved, followed by hot filtration to remove insolubles. After the filtrate was concentrated, the concentrate was purified by column chromatography (carrier: silica gel, eluent: dichloromethane/n-heptane). Then, recrystallization using n-heptane was performed to obtain 35.0 g (yield 78%) of 3-bromo-5-(biphenyl-4-yl)-10,10-dimethyl-5,10-dihydroindeno[1,2-b]indole as a white powder.

| A nitrogen-purged reaction vessel was charged with | 18.0 g, |
| --- | --- |
| the resulting 3-bromo-5-(biphenyl-4-yl)-10,10-dimethyl-5,10-dihydroindeno[1,2-b]indole | |
| bis(pinacolato)diboron | 12.8 g, |
| PdCl$_2$[dppf] | 0.9 g, |
| potassium acetate | 11.4 g, and |
| toluene | 180 ml. |

The mixture was heated, and refluxed for 24 hours with stirring. After the mixture was cooled, toluene was added, and the mixture was heated and dissolved, followed by hot filtration to remove insolubles. After the filtrate was concentrated, the concentrate was purified by column chromatography (carrier: silica gel, eluent: dichloromethane/n-heptane). Then, recrystallization using n-heptane was performed to obtain 9.8 g (yield 49%) of 5-(biphenyl-4-yl)-10,10-dimethyl-3-(4,4,5,5-tetramethyl-[1,3,2]dioxaborolan-2-yl)-5,10-dihydroindeno[1,2-b]indole as a white powder.

| A nitrogen-purged reaction vessel was charged with | 9.3 g, |
| --- | --- |
| the resulting 5-(biphenyl-4-yl)-10,10-dimethyl-3-(4,4,5,5-tetramethyl-[1,3,2]dioxaborolan-2-yl)-5,10-dihydroindeno[1,2-b]indole | |
| 10-(4-bromophenyl)-9,9-dimethyl-9H-acridan | 6.0 g, |
| tetrakis(triphenylphosphine)palladium | 0.6 g |
| 2M aqueous solution of potassium carbonate | 25 ml, |
| toluene | 42 ml, and |
| ethanol | 12 ml. |

The mixture was heated, and refluxed for 8 hours with stirring. The mixture was cooled to room temperature and, after ethyl acetate and water were added, an organic layer was collected by liquid separation. After the organic layer was concentrated, the concentrate was purified by column chromatography (carrier: silica gel, eluent: dichloromethane/n-heptane). Then, recrystallization using a dichloromethane/methanol solvent mixture was performed, whereafter recrystallization using a dichloromethane/acetone solvent mixture was repeated twice to obtain 5.6 g (yield 51%) of 3-{4-(9,9-dimethyl-9H-acridin-10-yl)phenyl}-5-(biphenyl-4-yl)-10,10-dimethyl-5,10-dihydroindeno[1,2-b]indole (Compound 76) as a white powder.

Figure 8:
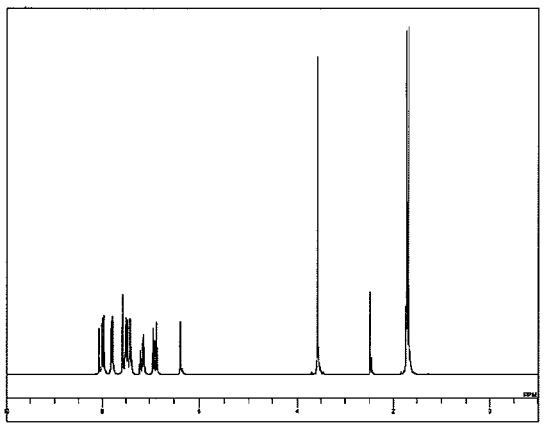
FIG. 8 is a $^1$H-NMR chart diagram of compound of Example 8 (Compound 76).

In connection with the resulting white powder, its structure was identified using NMR. The results of its $^1$H-NMR measurement are shown in FIG. 8. In $^1$H-NMR (THF-d$_8$), the following signals of 40 hydrogens were detected:

δ (ppm)=8.07 (1H)
8.01 (2H)
7.97 (2H)
7.79 (4H)
7.56 (2H)
7.52-7.46 (5H)
7.41 (2H)
7.39 (1H)
7.20 (1H)
7.16 (2H)
6.93 (2H)
6.87 (2H)
6.37 (2H)
1.73 (6H)
1.41 (6H)

Example 9 (Synthesis of Compound 77)

Synthesis of 10,10,10',10'-tetramethyl-5,5'-diphenyl-5,5',10,10'-tetrahydro-[3,3']bi(indeno[1,2-b]indolyl)

(Compound 77)

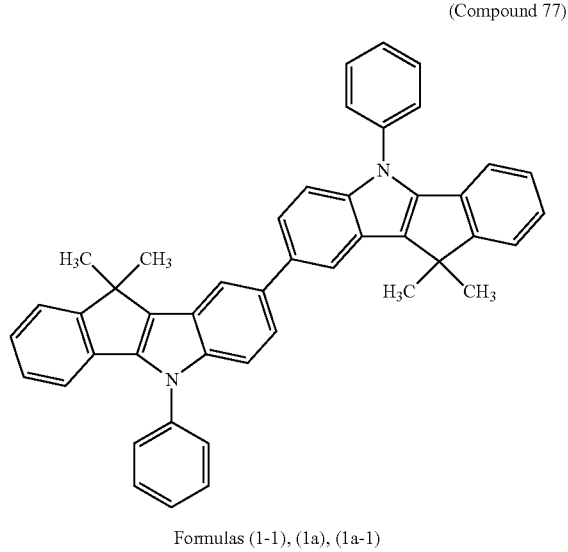 [SMILES: CC1(C)c2ccccc2-c2c1c1cc(-c3ccc4c(c3)c3c(n4-c4ccccc4)-c4ccccc4C3(C)C)ccc1n2-c1ccccc1]

Formulas (1-1), (1a), (1a-1)

| A nitrogen-purged reaction vessel was charged with | 10.0 g, |
|---|---|
| 3-bromo-5-phenyl-10,10-dimethyl-5,10-dihydroindeno[1,2-b]indole synthesized in Example 1 | |
| 5-phenyl-10,10-dimethyl-3-(4,4,5,5-tetramethyl-[1,3,2]dioxaborolan-2-yl)-5,10-dihydroindeno[1,2-b]indole synthesized in Example 2 | 12.3 g |
| tetrakis(triphenylphosphine)palladium | 0.9 g |
| 2M aqueous solution of potassium carbonate | 33 ml, |
| toluene | 70 ml, and |
| ethanol | 20 ml. |

The mixture was heated, and refluxed for 8 hours with stirring. The mixture was cooled to room temperature and, after ethyl acetate and water were added, an organic layer was collected by liquid separation. After the organic layer was concentrated, the concentrate was purified by column chromatography (carrier: silica gel, eluent: dichloromethane/n-heptane). Then, recrystallization from dichloromethane was performed to obtain 4.1 g (yield 26%) of 10,10,10',10'-tetramethyl-5,5'-diphenyl-5,5',10,10'-tetrahydro-[3,3']bi(indeno[1,2-b]indolyl) (Compound 77) as a white powder.

Figure 9:
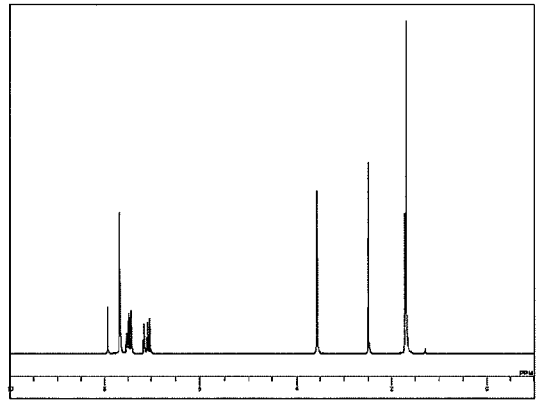
FIG. 9 is a $^1$H-NMR chart diagram of compound of Example 9 (Compound 77).

In connection with the resulting white powder, its structure was identified using NMR. The results of its ¹H-NMR measurement are shown in FIG. 9. In ¹H-NMR (THF-d₈), the following signals of 36 hydrogens were detected:

δ (ppm)=7.94 (2H)
7.66 (8H)
7.53 (2H)
7.48 (4H)
7.43 (2H)
7.16 (2H)
7.09 (2H)
7.03 (2H)
1.73 (12H)

Example 10 (Synthesis of Compound 78)

Synthesis of bis(biphenyl-4-yl)-[4-{5-(biphenyl-4-yl)-10,10-dimethyl-5,10-dihydroindeno[1,2-b]indol-3-yl}phenyl]amine (Compound 78)

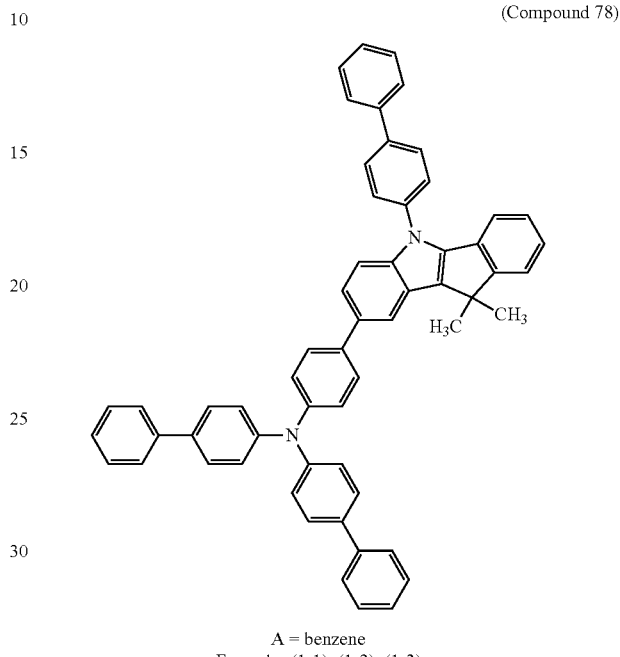

A = benzene
Formulas (1-1), (1-2), (1-3)

| A nitrogen-purged reaction vessel was charged with | 15.0 g, |
|---|---|
| 3-bromo-5-(biphenyl-4-yl)-10,10-dimethyl-5,10-dihydroindeno[1,2-b]indole synthesized in Example 8 | |
| bis(biphenyl-4-yl)-{4-(4,4,5,5-tetramethyl-[1,3,2]dioxaborolan-2-yl)phenyl}amine | 19.4 g |
| tetrakis(triphenylphosphine)palladium | 1.1 g |
| 2M aqueous solution of potassium carbonate | 48 ml, |
| toluene | 105 ml, and |
| ethanol | 26 ml. |

The mixture was heated, and refluxed for 8 hours with stirring. The mixture was cooled to room temperature, and a crude product was collected by filtration. Then, the crude product was washed with water, and then washed using methanol. Then, the washed product was dissolved in chlorobenzene, and subjected to purification by adsorption using silica gel. Then, the purified product was concentrated, and washed with toluene. Then, recrystallization from chlorobenzene was repeated twice, and then the recrystallized product was washed with methanol to obtain 11.8 g (yield 47%) of bis(biphenyl-4-yl)-[4-{5-(biphenyl-4-yl)-10,10-dimethyl-5,10-dihydroindeno[1,2-b]indol-3-yl}phenyl]amine (Compound 78) as a white powder.

Figure 10:
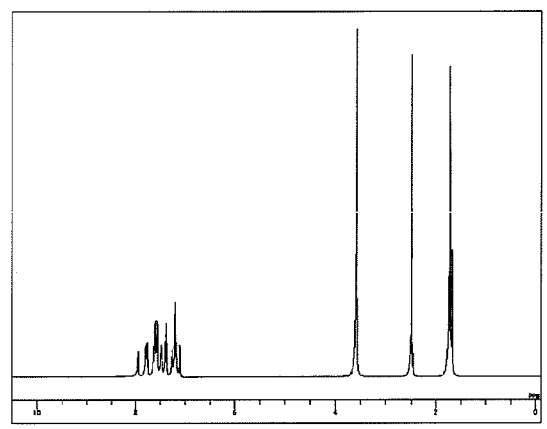
FIG. 10 is a $^1$H-NMR chart diagram of compound of Example 10 (Compound 78).

In connection with the resulting white powder, its structure was identified using NMR. The results of its ¹H-NMR measurement are shown in FIG. 10. In ¹H-NMR (THF-d₈), the following signals of 38 hydrogens were detected:

δ (ppm)=7.95 (2H)
7.80-7.75 (5H)

7.64-7.55 (10H)
7.48 (3H)
7.38 (4H)
7.27 (2H)
7.19 (5H)
7.11 (1H)
1.68 (6H)

Example 11 (Synthesis of Compound 79)

Synthesis of (biphenyl-4-yl)-(9,9-dimethyl-9H-fluoren-2-yl)-[4-{5-(biphenyl-4-yl)-10,10-dimethyl-5,10-dihydroindeno[1,2-b]indol-3-yl}phenyl]amine (Compound 79)

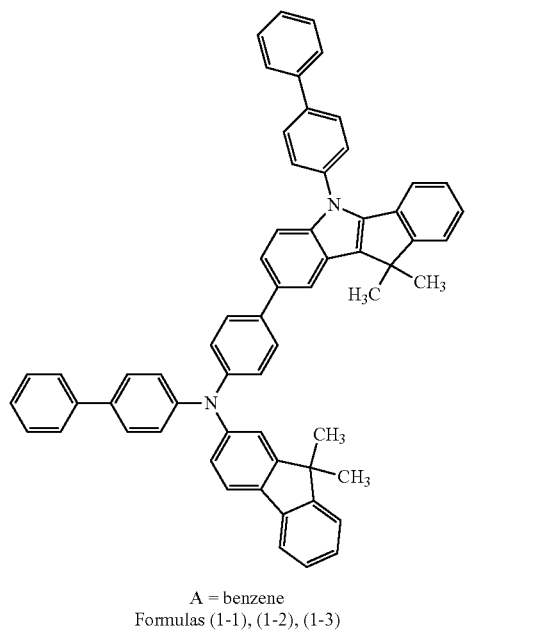

A = benzene
Formulas (1-1), (1-2), (1-3)

| | |
|---|---|
| A nitrogen-purged reaction vessel was charged with 3-bromo-5-(biphenyl-4-yl)-10,10-dimethyl-5,10-dihydroindeno[1,2-b]indole synthesized in Example 8 | 15.0 g, |
| (biphenyl-4-yl)-(9,9-dimethyl-9H-fluoren-2-yl)-{4-(4,4,5,5-tetramethyl-[1,3,2]dioxaborolan-2-yl)phenyl}amine | 20.9 g |
| tetrakis(triphenylphosphine)palladium | 1.1 g |
| 2M aqueous solution of potassium carbonate | 48 ml, |
| toluene | 105 ml, and |
| ethanol | 26 ml. |

The mixture was heated, and refluxed for 6 hours with stirring. The mixture was cooled to room temperature, and 200 ml of methanol was added. After the resulting precipitate was collected by filtration, washing with methanol and subsequent washing with water were performed to obtain a crude product. The crude product was subjected to recrystallization from a toluene/methanol solvent mixture, and then the recrystallized product was dissolved in toluene. The solution was purified by adsorption using silica gel to obtain 12.8 g (yield 48%) of (biphenyl-4-yl)-(9,9-dimethyl-9H-fluoren-2-yl)-[4-{5-(biphenyl-4-yl)-10,10-dimethyl-5,10-dihydroindeno[1,2-b]indol-3-yl}phenyl]amine (Compound 79) as a light yellowish white powder.

Figure 11:
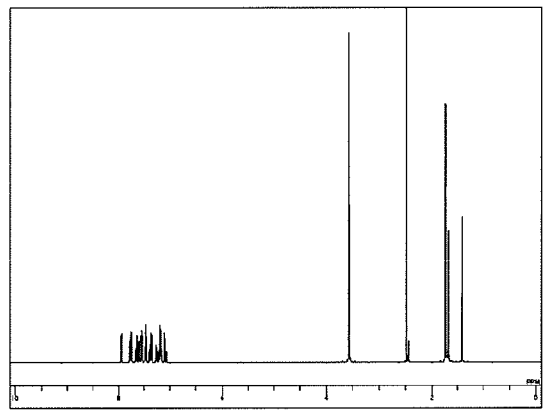
FIG. 11 is a $^1$H-NMR chart diagram of compound of Example 11 (Compound 79).

In connection with the resulting light yellowish white powder, its structure was identified using NMR. The results of its $^1$H-NMR measurement are shown in FIG. 11. In $^1$H-NMR (THF-$d_8$), the following signals of 48 hydrogens were detected:

δ (ppm)=7.95 (2H)
7.78 (2H)
7.76 (3H)
7.64-7.54 (9H)
7.47 (4H)
7.36 (4H)
7.20-7.18 (9H)
7.11-7.10 (3H)
1.67 (6H)
1.42 (6H)

Example 12 (Synthesis of Compound 80)

Synthesis of bis(biphenyl-4-yl)-{4'-(5-phenyl-10,10-dimethyl-5,10-dihydroindeno[1,2-b]indol-3-yl)biphenyl-4-yl}amine (Compound 80)

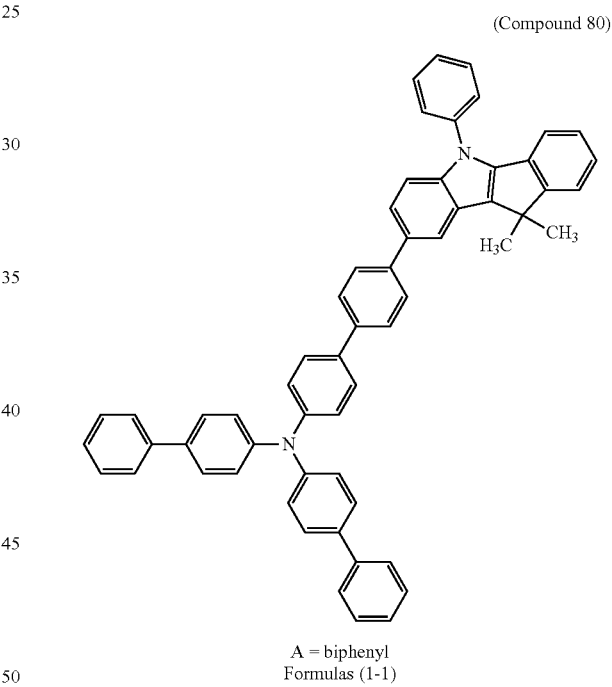

A = biphenyl
Formulas (1-1)

| | |
|---|---|
| A nitrogen-purged reaction vessel was charged with 3-bromo-5-phenyl-10,10-dimethyl-5,10-dihydroindeno[1,2-b]indole synthesized in Example 1 | 8.0 g, |
| bis(biphenyl-4-yl)-{4-(4,4,5,5-tetramethyl-[1,3,2]dioxaborolan-2-yl)biphenyl-4-yl}amine | 13.6 g |
| tetrakis(triphenylphosphine)palladium | 0.7 g |
| 2M aqueous solution of potassium carbonate | 31 ml, |
| toluene | 56 ml, and |
| ethanol | 16 ml. |

The mixture was heated, and refluxed for 24 hours with stirring. The mixture was cooled to room temperature and, after ethyl acetate and water were added, an organic layer was collected by liquid separation. After the organic layer was concentrated, the concentrate was purified by column chromatography (carrier: silica gel, eluent: dichloromethane/n-heptane). Then, recrystallization using a dichloromethane/acetone solvent mixture was repeated 4 times, whereafter recrystallization using a dichloromethane/ethyl acetate solvent mixture was performed to obtain 4.2 g (yield 26%) of bis(biphenyl-4-yl)-{4'-(5-(phenyl-10,10-dimethyl-5,10-dihydroindeno[1,2-b]indol-3-yl)biphenyl-4-yl}amine (Compound 80) as a white powder.

Figure 12:
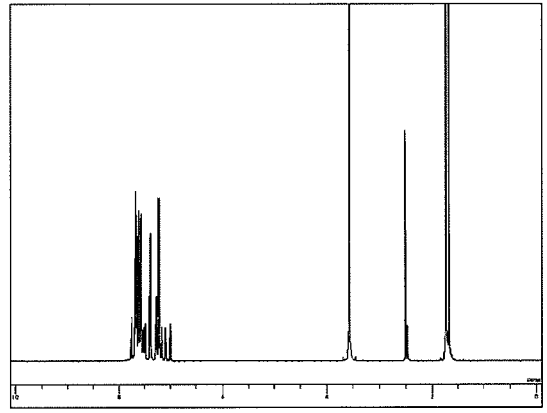
FIG. 12 is a $^1$H-NMR chart diagram of compound of Example 12 (Compound 80).

In connection with the resulting white powder, its structure was identified using NMR. The results of its $^1$H-NMR measurement are shown in FIG. 12. In $^1$H-NMR (THF-$d_8$), the following signals of 44 hydrogens were detected:

δ (ppm)=7.76 (1H)
7.70-7.65 (8H)
7.63-7.61 (7H)
7.58 (4H)
7.54 (1H)
7.51 (1H)
7.49 (1H)
7.40 (4H)
7.27 (2H)
7.22 (6H)
7.17 (1H)
7.09 (1H)
7.01 (1H)
1.67 (6H)

Example 13 (Synthesis of Compound 81)

Synthesis of (biphenyl-4-yl)-[4'-{5-(biphenyl-4-yl)-10,10-dimethyl-5,10-dihydroindeno[1,2-b]indol-3-yl}biphenyl-4-yl]-phenylamine (Compound 81)

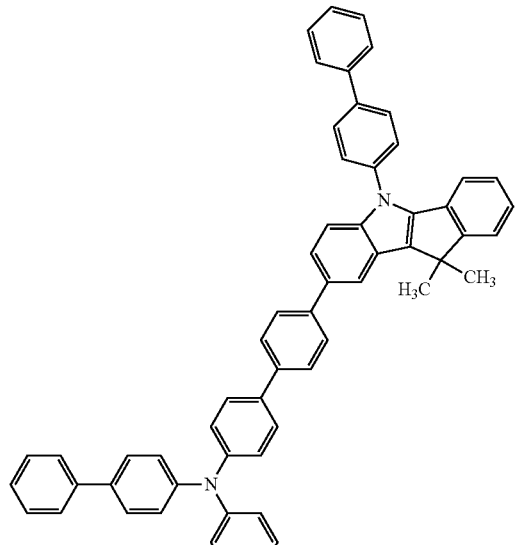

A = biphenyl
Formula (1-1)

A nitrogen-purged reaction vessel was charged with 10.0 g, 3-bromo-5-(biphenyl-4-yl)-10,10-dimethyl-5,10-dihydroindeno[1,2-b]indole synthesized in Example 8

-continued

| | |
|---|---|
| (biphenyl-4-yl)-{4'-(4,4,5,5-tetramethyl-[1,3,2]dioxaborolan-2-yl)biphenyl-4-yl}-phenylamine | 12.4 g |
| tetrakis(triphenylphosphine)palladium | 0.7 g |
| 2M aqueous solution of potassium carbonate | 33 ml, |
| toluene | 70 ml, and |
| ethanol | 20 ml. |

The mixture was heated, and refluxed for 24 hours with stirring. The mixture was cooled to room temperature, and 200 ml of methanol was added. After the resulting precipitate was collected by filtration, the collected precipitate was heated and dissolved in toluene, followed by hot filtration to remove insolubles. The filtrate was concentrated, whereafter recrystallization using toluene was repeated 4 times to obtain 4.9 g (yield 29%) of (biphenyl-4-yl)-[4'-{5-(biphenyl-4-yl)-10,10-dimethyl-5,10-dihydroindeno[1,2-b]indol-3-yl}biphenyl-4-yl]-phenylamine (Compound 81) as a white powder.

Figure 13:
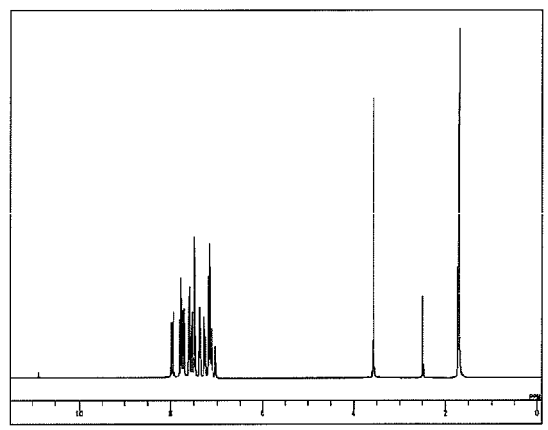
FIG. 13 is a $^1$H-NMR chart diagram of compound of Example 13 (Compound 81).

In connection with the resulting white powder, its structure was identified using NMR. The results of its $^1$H-NMR measurement are shown in FIG. 13. In $^1$H-NMR (THF-$d_8$), the following signals of 44 hydrogens were detected:

δ (ppm)=7.99 (1H)
7.95 (2H)
7.79 (4H)
7.74 (2H)
7.70 (2H)
7.61 (4H)
7.56 (2H)
7.49 (5H)
7.39 (3H)
7.28 (3H)
7.19-7.15 (9H)
7.04 (1H)
1.69 (6H)

Example 14 (Synthesis of Compound 9)

Synthesis of (9,9-dimethyl-9H-fluoren-2-yl)-{4-(5-phenyl-10,10-dimethyl-5,10-dihydroindeno[1,2-b]indol-3-yl)phenyl}-phenylamine (Compound 9)

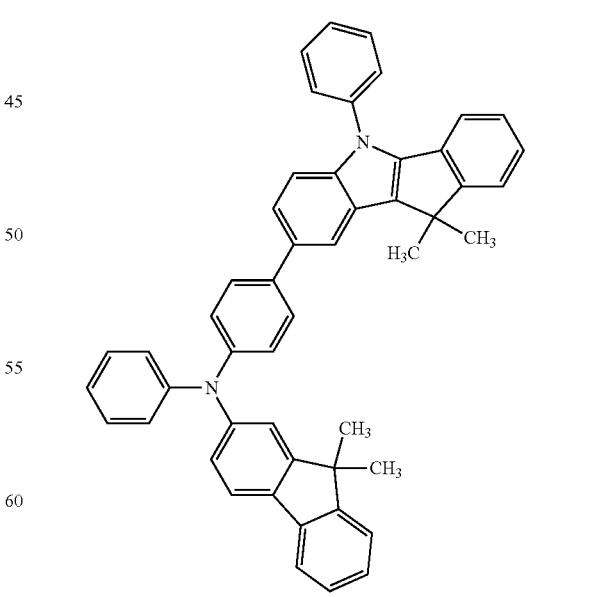

A = benzene
Formulas (1-1), (1-2), (1-3)

| | |
|---|---|
| A nitrogen-purged reaction vessel was charged with | 14.0 g, |
| 3-bromo-10,10-dimethyl-5,10-dihydroindeno[1,2-b] | |
| indole synthesized in Example 8 | |
| (9,9-dimethyl-9H-fluoren-2-yl)-{4-(4,4,5,5- | 24.4 g, |
| tetramethyl-[1,3,2]dioxaborolan-2-yl)phenyl}- | |
| phenylamine | |
| tris(dibenzylideneacetone)dipalladium(0) | 0.6 g |
| diadamantylbutylphosphine | 0.9 g |
| 1,4-dioxane | 10 ml, and |
| water | 28 ml. |

The mixture was heated, and stirred at 87° C. for 3 hours. The mixture was cooled to room temperature, and concentrated. Then, toluene and water were added, and an organic layer was collected by liquid separation. The organic layer was concentrated, and the concentrate was washed with n-hexane. Then, the system was dissolved in a 1,2-dichlorobenzene/toluene solvent mixture, and the solution was subjected to purification by adsorption using silica gel, thereby obtaining a crude product. Then, the crude product was washed using n-hexane to obtain 22.2 g (yield 83%) of (9,9-dimethyl-9H-fluoren-2-yl)-{4-(10,10-dimethyl-5,10-dihydroindeno[1,2-b]indol-3-yl)phenyl}-phenylamine as a white powder.

| | |
|---|---|
| A nitrogen-purged reaction vessel was charged with | 5.5 g, |
| the resulting (9,9-dimethyl-9H-fluoren-2-yl)-{4- | |
| (10,10-dimethyl-5,10-dihydroindeno[1,2-b]indol-3-yl) | |
| phenyl}-phenylamine | |
| iodobenzene | 2.3 g, |
| tert-butoxysodium | 1.3 g, |
| tri-tert-butylphosphine | 0.1 g |
| tris(dibenzylideneacetone)dipalladium(0) | 0.1 g, and |
| toluene | 110 ml. |

The mixture was heated, and refluxed for 4.5 hours with stirring. The mixture was cooled to room temperature, and insolubles were removed by filtration. Then, the filtrate was concentrated to obtain a crude product. The crude product was purified by column chromatography (carrier: silica gel, eluent: toluene/n-hexane) to obtain 5.7 g (yield 92%) of (9,9-dimethyl-9H-fluoren-2-yl)-{4-(5-phenyl-10,10-dimethyl-5,10-dihydroindeno[1,2-b]indol-3-yl)phenyl}-phenylamine (Compound 9) as a white powder.

Figure 14:
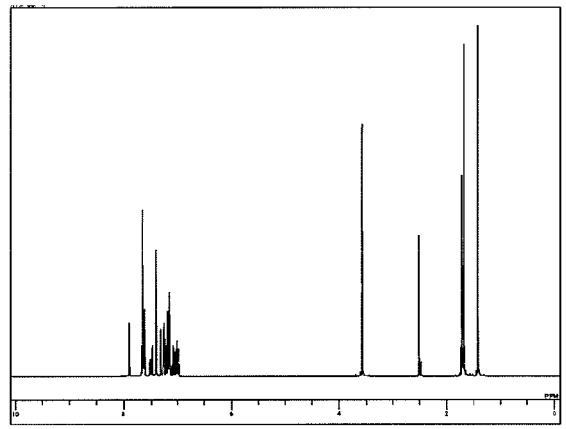
FIG. 14 is a $^1$H-NMR chart diagram of compound of Example 14 (Compound 9).

In connection with the resulting white powder, its structure was identified using NMR. The results of its $^1$H-NMR measurement are shown in FIG. 14. In $^1$H-NMR (THF-$d_8$), the following signals of 40 hydrogens were detected:

δ (ppm)=7.91 (1H)
7.68-7.60 (8H)
7.53-7.50 (1H)
7.48 (1)
7.41 (3H)
7.33 (1H)
7.28-7.25 (3H)
7.21 (1H)
7.19-7.15 (5H)
7.09 (1H)
7.05 (1H)
7.02 (1H)
7.00 (1H)
1.68 (6H)
1.42 (6H)

Example 15 (Synthesis of Compound 11)

Synthesis of (9,9-dimethyl-9H-fluoren-2-yl)-[4-{5-(biphenyl-4-yl)-10,10-dimethyl-5,10-dihydroindeno[1,2-b]indol-3-yl}phenyl]-phenylamine

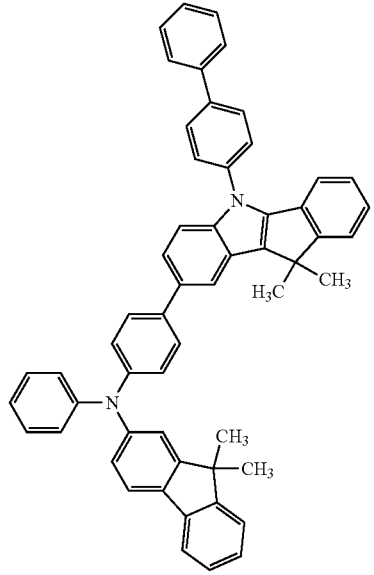

(Compound 11)

A = benzene
Formulas (1-1), (1-2), (1-3)

| | |
|---|---|
| A nitrogen-purged reaction vessel was charged with | 19.7 g, |
| (9,9-dimethyl-9H-fluoren-2-yl)-{4-(10,10-dimethyl-5, | |
| 10-dihydroindeno[1,2-b]indol-3-yl)phenyl}-phenylamine | |
| synthesized in Example 14 | |
| 4-bromobiphenyl | 9.3 g, |
| tert-butoxysodium | 4.8 g, |
| tri-tert-butylphosphine | 0.3 g, |
| tris(dibenzylideneacetone)dipalladium(0) | 0.3 g, and |
| toluene | 400 ml. |

The mixture was heated, and refluxed for 4 hours with stirring. The mixture was cooled to room temperature, and insolubles were removed by filtration. Then, the filtrate was concentrated to obtain a crude product. The crude product was purified by column chromatography (carrier: silica gel, eluent: toluene/n-hexane) to obtain 21.1 g (yield 85%) of (9,9-dimethyl-9H-fluoren-2-yl)-[4-{5-(biphenyl-4-yl)-10,10-dimethyl-5,10-dihydroindeno[1,2-b]indol-3-yl}phenyl]-phenylamine (Compound 11) as a white powder.

Figure 15:
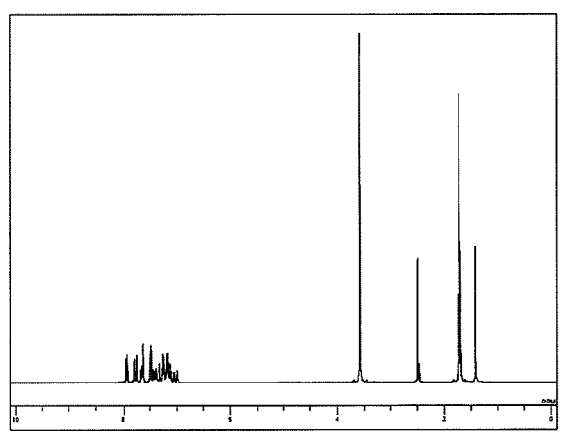
FIG. 15 is a $^1$H-NMR chart diagram of compound of Example 15 (Compound 11).

In connection with the resulting white powder, its structure was identified using NMR. The results of its $^1$H-NMR measurement are shown in FIG. 15. In $^1$H-NMR (THF-$d_8$), the following signals of 44 hydrogens were detected:

δ (ppm)=7.95 (2H)
7.92 (1H)
7.79 (2H)
7.75 (2H)
7.67 (1H)
7.63 (3H)
7.49 (4H)
7.44 (1H)
7.41 (1H)

7.38 (1H)
7.33 (1H)
7.26 (3H)
7.23-7.11 (8H)
7.06 (1H)
7.00 (1H)
1.70 (6H)
1.42 (6H)

Example 16 (Synthesis of Compound 21)

Synthesis of (9,9-dimethyl-9H-fluoren-2-yl)-[4-{5-(naphthalen-2-yl)-10,10-dimethyl-5,10-dihydroindeno[1,2-b]indol-3-yl}phenyl]-phenylamine Formulas (1-1), (1-2), (1-3)

(Compound 21)

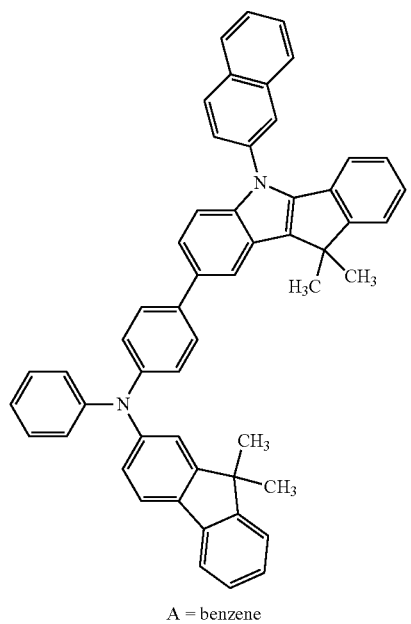

A = benzene

| | |
|---|---|
| A nitrogen-purged reaction vessel was charged with (9,9-dimethyl-9H-fluoren-2-yl)-{4-(10,10-dimethyl-5,10-dihydroindeno{1,2-b]indol-3-yl)phenyl}-phenylamine synthesized in Example 14 | 16.5 g, |
| 2-bromonaphthalene | 8.65 g, |
| copper powder | 0.18 g, |
| potassium carbonate | 11.54 g, |
| 3,5-di-tert-butylsalicylic acid | 0.70 g, |
| sodium hydrogen sulfite | 0.87 g, and |
| dodecylbenzene | 165 ml. |

The mixture was heated, and stirred at 200° C. for 42 hours. After the mixture was cooled, 330 ml of toluene was added, and the system was heated and dissolved. Insolubles were removed by filtration, and the filtrate was concentrated. Then, 330 ml of n-hexane was added, whereafter the resulting precipitate was collected by filtration. Recrystallization using a toluene/n-hexane solvent mixture was repeated twice to obtain 16.6 g (yield 81%) of (9,9-dimethyl-9H-fluoren-2-yl)-[4-{5-(naphthalen-2-yl)-10,10-dimethyl-5,10-dihydroindeno[1,2-b]indol-3-yl}phenyl]-phenylamine (Compound 21) as a white powder.

Figure 16:
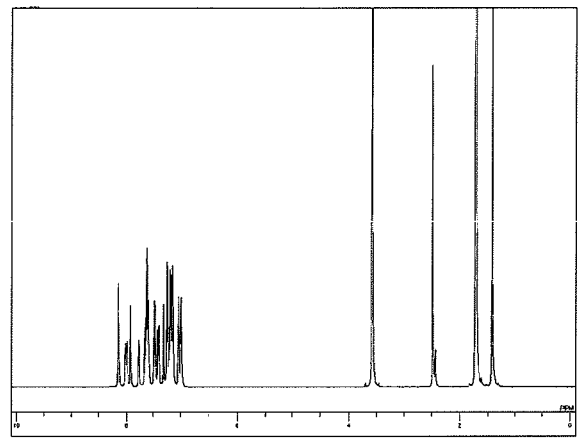
FIG. 16 is a $^1$H-NMR chart diagram of compound of Example 16 (Compound 21).

In connection with the resulting white powder, its structure was identified using NMR. The results of its $^1$H-NMR measurement are shown in FIG. 16. In $^1$H-NMR (THF-$d_8$), the following signals of 42 hydrogens were detected:

δ (ppm)=8.15 (2H)
8.03 (2H)
7.93 (1H)
7.76 (1H)
7.67-7.58 (6H)
7.48 (2H)
7.41 (2H)
7.32 (1H)
7.27-7.15 (9H)
7.05 (2H)
7.00 (2H)
1.71 (6H)
1.42 (6H)

Example 17 (Synthesis of Compound 17)

Synthesis of (biphenyl-4-yl)-[4-{5-(9,9-dimethyl-9H-fluoren-2-yl)-10,10-dimethyl-5,10-dihydroindeno[1,2-b]indol-3-yl}phenyl]-phenylamine Formulas (1-1), (1-2), (1-3)

(Compound 17)

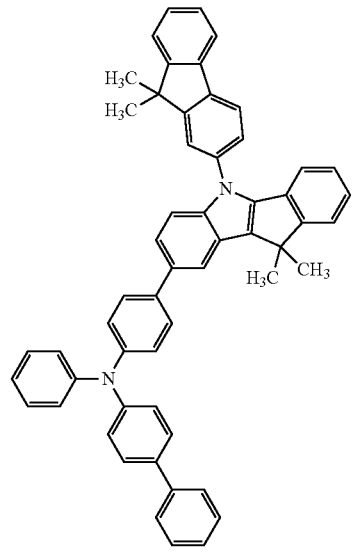

A = benzene

| | |
|---|---|
| A nitrogen-purged reaction vessel was charged with 3-bromo-10,10-dimethyl-5,10-dihydroindeno[1,2-b]indole synthesized in Example 8 | 24.3 g, |
| (biphenyl-4-yl)-{4-(4,4,5,5-tetramethyl-[1,3,2] dioxaborolan-2-yl)phenyl}-phenylamine | 41.8 g |

-continued

| | |
|---|---|
| tetrakis(triphenylphosphine)palladium | 2.7 g |
| 2M aqueous solution of potassium carbonate | 100 ml, |
| toluene | 150 ml, and |
| ethanol | 50 ml. |

The mixture was heated, and refluxed for 1 hour with stirring. The mixture was cooled to room temperature and, after ethyl acetate and water were added, an organic layer was collected by liquid separation. The organic layer was concentrated, and then the concentrate was heated and dissolved with the addition of toluene, followed by hot filtration to remove insolubles. After the filtrate was concentrated, recrystallization using dichloromethane was performed, whereafter recrystallization using toluene was repeated twice to obtain 22.6 g (yield 53%) of (biphenyl-4-yl)-{4-(10,10-dimethyl-5,10-dihydroindeno[1,2-b]indol-3-yl)phenyl}-phenylamine as a white powder.

| | |
|---|---|
| A nitrogen-purged reaction vessel was charged with the resulting (biphenyl-4-yl)-{4-(10,10-dimethyl-5,10-dihydroindeno[1,2-b]indol-3-yl)phenyl}-phenylamine | 22.2 g, |
| 2-bromo-9,9-dimethyl-9H-fluorene | 10.0 g, |
| palladium acetate | 0.3 g |
| tert-butoxysodium | 14.1 g, |
| toluene | 200 ml, and |
| tri(tert-butyl)phosphine | 0.3 g. |

The mixture was heated, and refluxed for 24 hours with stirring. The mixture was cooled to room temperature, and added to methanol. The resulting precipitate was collected by filtration, and then heated and dissolved in toluene, followed by hot filtration to remove insolubles. After the filtrate was concentrated, recrystallization using a dichloromethane/acetone solvent mixture was performed, whereafter recrystallization using dichloromethane was carried out. Then, recrystallization using a dichloromethane/acetone solvent mixture was performed to obtain 10.8 g (yield 40%) of (biphenyl-4-yl)-[4-{5-(9,9-dimethyl-9H-fluoren-2-yl)-10,10-dimethyl-5,10-dihydroindeno[1,2-b]indol-3-yl}phenyl]-phenyamine (Compound 17) as a white powder.

Figure 17:
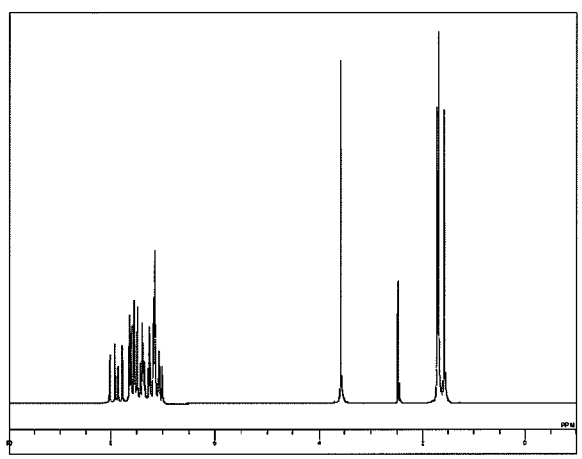
FIG. 17 is a $^1$H-NMR chart diagram of compound of Example 17 (Compound 17).

In connection with the resulting white powder, its structure was identified using NMR. The results of its $^1$H-NMR measurement are shown in FIG. 17. In $^1$H-NMR (THF-$d_8$), the following signals of 44 hydrogens were detected:

δ (ppm)=8.03 (1H)
7.92 (1H)
7.86 (1H)
7.77 (1H)
7.64-7.60 (6H)
7.55 (3H)
7.49 (2H)
7.48 (1H)
7.44-7.35 (4H)
7.27 (3H)
7.20-7.16 (6H)
7.08 (2H)
7.02 (1H)
1.70 (6H)
1.59 (6H)

Example 18 (Synthesis of Compound 51)

Synthesis of (biphenyl-4-yl)-(9,9-dimethyl-9H-fluoren-2-yl)-(5-phenyl-10,10-dimethyl-5,10-dihydroindeno[1,2-b]indol-3-yl)amine Formulas (1-1), (1-4)

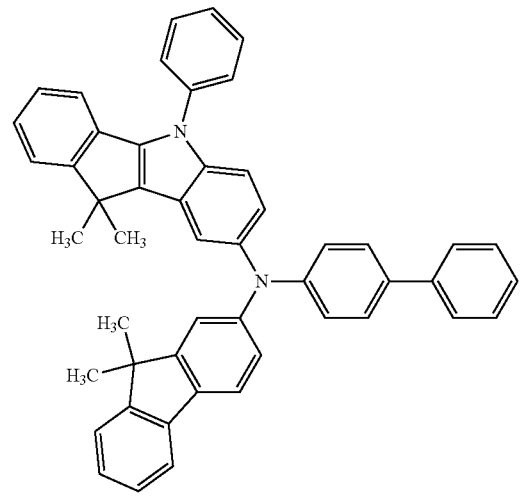

(Compound 51)

A = single bond

| | |
|---|---|
| A nitrogen-purged reaction vessel was charged with 3-bromo-5-phenyl-10,10-dimethyl-5,10-dihydroindeno[1,2-b]indole synthesized in Example 1 | 20.0 g, |
| (biphenyl-4-yl)-(9,9-dimethyl-9H-fluoren-2-yl)amine | 20.5 g, |
| tert-butoxysodium | 14.8 g, |
| tri-tert-butylphosphine | 0.5 g, |
| tris(dibenzylideneacetone)dipalladium(0) | 2.4 g, and |
| toluene | 200 ml. |

The mixture was heated, and stirred at 100° C. for 24 hours. The mixture was cooled to room temperature, and added to methanol. The resulting precipitate was collected by filtration, and then heated and dissolved in toluene, followed by hot filtration to remove insolubles. After the filtrate was concentrated, recrystallization using a dichloromethane/methanol solvent mixture was performed, whereafter recrystallization using a toluene/methanol solvent mixture was carried out to obtain 30.0 g (yield 87%) of (biphenyl-4-yl)-(9,9-dimethyl-9H-fluoren-2-yl)-(5-phenyl-10,10-dimethyl-5,10-dihydroindeno[1,2-b]indol-3-yl)amine (Compound 51) as a white powder.

Figure 18:
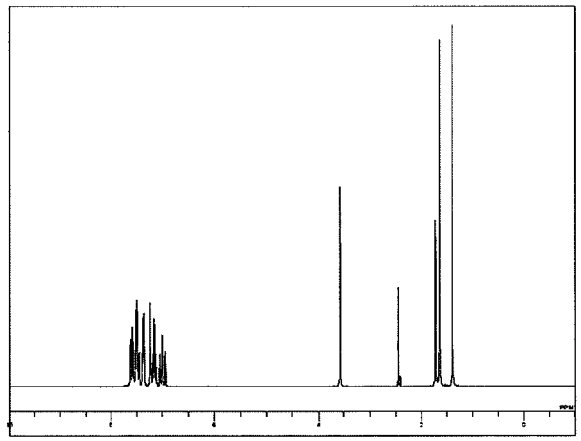
FIG. 18 is a $^1$H-NMR chart diagram of compound of Example 18 (Compound 51).

In connection with the resulting white powder, its structure was identified using NMR. The results of its $^1$H-NMR measurement are shown in FIG. 18. In $^1$H-NMR (THF-$d_8$), the following signals of 40 hydrogens were detected:

δ (ppm)=7.63 (2H)
7.58 (3H)
7.50 (7H)
7.36 (5H)
7.24 (3H)
7.16 (4H)
7.06 (1H)
7.01 (2H)

6.95 (1H)
1.65 (6H)
1.40 (6H)

Example 19 (Synthesis of Compound 52)

Synthesis of bis(biphenyl-4-yl)-(5-phenyl-10,10-dimethyl-5,10-dihydroindeno[1,2-b]indol-3-yl)amine Formulas (1-1), (1-4)

(Compound 52)

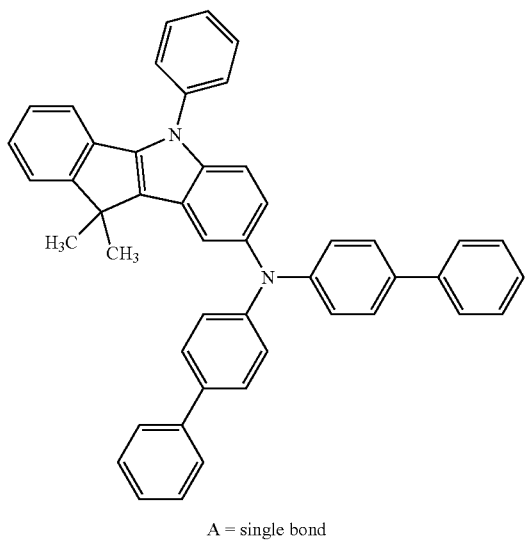

A = single bond

| | |
|---|---|
| A nitrogen-purged reaction vessel was charged with | 10.0 g, |
| 3-bromo-5-phenyl-10,10-dimethyl-5,10-dihydroindeno[1,2-b]indole synthesized in Example 1 | |
| bis(biphenyl-4-yl)amine | 9.1 g, |
| tert-butoxysodium | 7.4 g, |
| tri-tert-butylphosphine | 0.3 g, |
| tris(dibenzylideneacetone)dipalladium(0) | 1.2 g, and |
| toluene | 80 ml. |

The mixture was heated, and stirred at 100° C. for 24 hours. The mixture was cooled to room temperature, and added to methanol. The resulting precipitate was collected by filtration, and then heated and dissolved in toluene, followed by hot filtration to remove insolubles. After the filtrate was concentrated, recrystallization using a dichloromethane/methanol solvent mixture was performed, whereafter recrystallization using a toluene/methanol solvent mixture was carried out. Then, recrystallization using a toluene/acetone solvent mixture was performed to obtain 10.5 g (yield 65%) of bis(biphenyl-4-yl)-(5-phenyl-10,10-dimethyl-5,10-dihydroindeno[1,2-b]indol-3-yl)amine (Compound 52) as a white powder.

Figure 19:
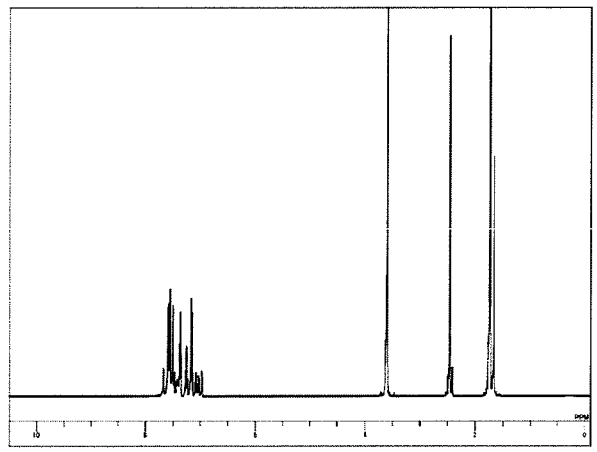
FIG. 19 is a $^1$H-NMR chart diagram of compound of Example 19 (Compound 52).

In connection with the resulting white powder, its structure was identified using NMR. The results of its $^1$H-NMR measurement are shown in FIG. 19. In $^1$H-NMR (THF-d$_8$), the following signals of 36 hydrogens were detected:

δ (ppm)=7.68 (1H)
7.59 (5H)
7.55 (3H)
7.50 (4H)
7.47 (1H)
7.42 (1H)
7.37 (4H)
7.24 (3H)
7.16 (5H)
7.07 (1H)
7.03 (1H)
6.97 (1H)
1.67 (6H)

Example 20 (Synthesis of Compound 56)

Synthesis of (biphenyl-4-yl)-(9,9-dimethyl-9H-fluoren-2-yl)-(5-(biphenyl-4-yl)-10,10-dimethyl-5,10-dihydroindeno[1,2-b]indol-3-yl)amine Formulas (1-1), (1-4)

(Compound 56)

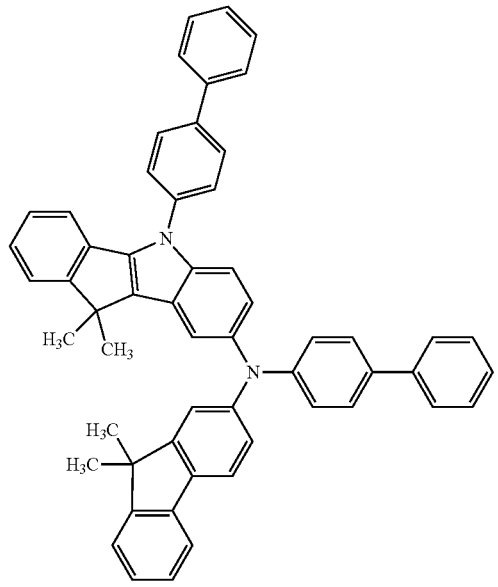

A = single bond

| | |
|---|---|
| A nitrogen-purged reaction vessel was charged with | 13.6 g, |
| 3-bromo-5-(biphenyl-4-yl)-10,10-dimethyl-5,10-dihydroindeno[1,2-b]indole synthesized in Example 8 | |
| (biphenyl-4-yl)-(9,9-dimethyl-9H-fluoren-2-yl)amine | 12.7 g, |
| tert-butoxysodium | 8.4 g, |
| tri-tert-butylphosphine | 0.3 g, |
| tris(dibenzylideneacetone)dipalladium(0) | 1.3 g, and |
| toluene | 80 ml. |

The mixture was heated, and stirred at 100° C. for 24 hours. The mixture was cooled to room temperature, and added to methanol. The resulting precipitate was collected by filtration, and then purified by column chromatography (carrier: silica gel, eluent: dichloromethane/n-heptane). Then, recrystallization using a dichloromethane/methanol solvent mixture was performed, whereafter recrystallization using a dichloromethane/acetone solvent mixture was repeated 3 times to obtain 10.1 g (yield 46%) of (biphenyl-4-yl)-(9,9-dimethyl-9H-fluoren-2-yl)-{5-(biphenyl-4-yl)-10,10-dimethyl-5,10-dihydroindeno[1,2-b]indol-3-yl}amine (Compound 56) as a white powder.

Figure 20:
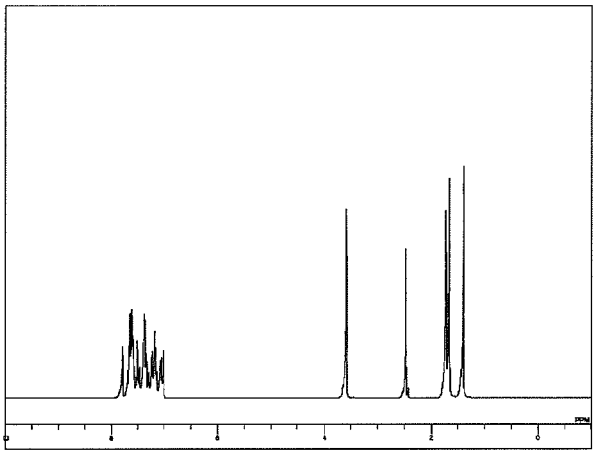
FIG. 20 is a $^1$H-NMR chart diagram of compound of Example 20 (Compound 56).

In connection with the resulting white powder, its structure was identified using NMR. The results of its ¹H-NMR measurement are shown in FIG. 20. In ¹H-NMR (THF-d₈), the following signals of 44 hydrogens were detected:

δ (ppm)=7.79 (2H)
7.66-7.56 (9H)
7.50 (3H)
7.40-7.34 (7H)
7.31-7.28 (1H)
7.24-7.16 (6H)
7.08-7.01 (4H)
1.66 (6H)
1.41 (6H)

Example 21 (Synthesis of Compound 58)

Synthesis of (biphenyl-4-yl)-(9,9-dimethyl-9H-fluoren-2-yl)-{5-(9,9-dimethyl-9H-fluoren-2-yl)-10,10-dimethyl-5,10-dihydroindeno[1,2-b]indol-3-yl}amine Formulas (1-1), (1-4)

(Compound 58)

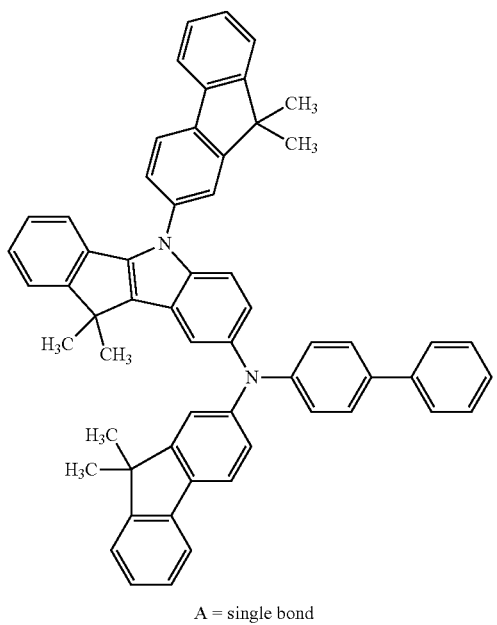

A = single bond

| | |
|---|---|
| A nitrogen-purged reaction vessel was charged with | 12.0 g, |
| 10,10-dimethyl-5,10-dihydroindeno[1,2-b]indole | |
| 2-iodo-9,9-dimethylfluorene | 24.7 g, |
| copper(I) iodide | 0.49 g, |
| tripotassium phosphate | 32.8 g, |
| 1,2-cyclohexanediamine | 17.6 g and |
| 1,4-dioxane | 96 ml. |

The mixture was heated, and refluxed for 6 hours with stirring. The mixture was cooled to room temperature, and insolubles were removed by filtration using Celite as an aid. Then, the filtrate was concentrated to obtain a crude product. The crude product was purified by column chromatography (carrier: silica gel, eluent: dichloromethane/n-heptane), and then recrystallized from methanol to obtain 19.7 g (yield 90%) of 5-(9,9-dimethyl-9H-fluoren-2-yl)-10,10-dimethyl-5,10-dihydroindeno[1,2-b]indole as a white powder.

| | |
|---|---|
| A nitrogen-purged reaction vessel was charged with the resulting 5-(9,9-dimethyl-9H-fluoren-2-yl)-10,10-dimethyl-5,10-dihydroindeno[1,2-b]indole | 19.7 g, and |
| dimethylformamide | 98 ml. |

The mixture was cooled to 0° C. with stirring. A solution of 8.2 g of N-bromosuccinimide dissolved in 98 ml of dimethylformamide was added dropwise, and then the mixture was further stirred at room temperature for 10 hours. The mixture was added to 1,000 ml of water, and the resulting precipitate was collected by filtration. Then, recrystallization using a dichloromethane/methanol solvent mixture was repeated twice, thereby obtaining 17.2 g (yield 73%) of 3-bromo-5-(9,9-dimethyl-9H-fluoren-2-yl)-10,10-dimethyl-5,10-dihydroindeno[1,2-b]indole as a white powder.

| | |
|---|---|
| A nitrogen-purged reaction vessel was charged with the resulting 3-bromo-5-(9,9-dimethyl-9H-fluoren-2-yl)-10,10-dimethyl-5,10-dihydroindeno[1,2-b]indole | 12.0 g, |
| (biphenyl-4-yl)-(9,9-dimethyl-9H-fluoren-2-yl)amine | 9.9 g, |
| tert-butoxysodium | 6.9 g, |
| tri-tert-butylphosphine | 0.4 g, |
| tris(dibenzylideneacetone)dipalladium(0) | 0.7 g, and |
| toluene | 120 ml. |

The mixture was heated, and refluxed for 3 hours with stirring. The mixture was cooled to room temperature, and added to methanol. The resulting precipitate was collected by filtration, and then heated and dissolved in toluene, followed by hot filtration to remove insolubles. After the filtrate was concentrated, recrystallization using methanol was performed, whereafter recrystallization using a THF/acetone solvent mixture was carried out to obtain 7.0 g (yield 37%) of (biphenyl-4-yl)-(9,9-dimethyl-9H-fluoren-2-yl)-{5-(9,9-dimethyl-9H-fluoren-2-yl)-10,10-dimethyl-5,10-dihydroindeno[1,2-b]indol-3-yl}amine (Compound 58) as a white powder.

Figure 21:
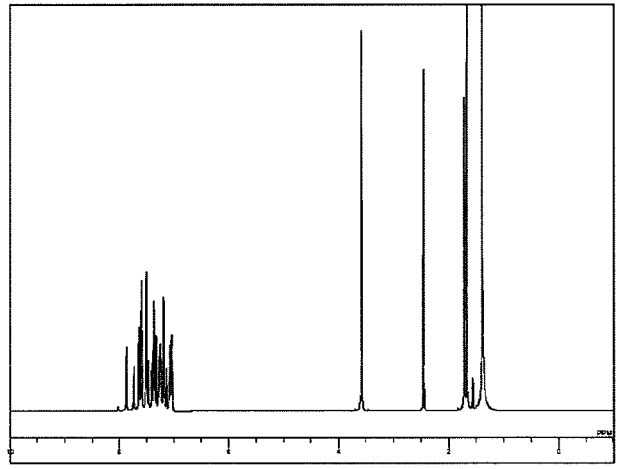
FIG. 21 is a $^1$H-NMR chart diagram of compound of Example 21 (Compound 58).

In connection with the resulting white powder, its structure was identified using NMR. The results of its ¹H-NMR measurement are shown in FIG. 21. In ¹H-NMR (THF-d₈), the following signals of 48 hydrogens were detected:

δ (ppm)=7.87 (1H)
7.73 (1H)
7.64 (2H)
7.59 (4H)
7.50 (3H)
7.43 (1H)
7.38 (1H)
7.34 (4H)
7.32 (1H)
7.28-7.23 (4H)
7.19 (3H)
7.15 (1H)
7.08-7.05 (4H)
1.67 (6H)
1.41 (12H)

<Measurement of Glass Transition Point>

The indenoindole derivatives of the present invention obtained in the foregoing Examples were measured for the glass transition point by a high sensitivity differential scanning calorimeter (DSC3100S, produced by Bruker AXS).

| | Glass transition point |
|---|---|
| Compound of Example 1 | 151° C. |
| Compound of Example 2 | 141° C. |
| Compound of Example 3 | 123° C. |
| Compound of Example 4 | 144° C. |
| Compound of Example 6 | 149° C. |
| Compound of Example 7 | 132° C. |
| Compound of Example 8 | 149° C. |
| Compound of Example 10 | 154° C. |
| Compound of Example 11 | 160° C. |
| Compound of Example 12 | 145° C. |
| Compound of Example 13 | 147° C. |
| Compound of Example 14 | 133° C. |
| Compound of Example 15 | 146° C. |
| Compound of Example 16 | 145° C. |
| Compound of Example 17 | 149° C. |
| Compound of Example 18 | 141° C. |
| Compound of Example 19 | 128° C. |
| Compound of Example 20 | 147° C. |

The indenoindole derivatives of the present invention have a glass transition point of 100° C. or higher, particularly, 120° C. or higher, demonstrating that the indenoindole derivatives of the present invention are stable in a thin film state.

<Evaluation of Work Function>

Using each of the indenoindole derivatives of the present invention obtained in the above Examples, a vapor deposited film with a film thickness of 100 nm was prepared on an ITO substrate, and its work function was measured using an ionization potential measuring device (PYS-202, produced by Sumitomo Heavy Industries, Ltd.).

| | Work function |
|---|---|
| Compound of Example 1 | 5.48 eV |
| Compound of Example 2 | 5.64 eV |
| Compound of Example 3 | 5.71 eV |
| Compound of Example 4 | 5.66 eV |
| Compound of Example 6 | 5.62 eV |
| Compound of Example 7 | 5.95 eV |
| Compound of Example 10 | 5.56 eV |
| Compound of Example 11 | 5.49 eV |
| Compound of Example 14 | 5.64 eV |
| Compound of Example 15 | 5.62 eV |
| Compound of Example 16 | 5.57 eV |
| Compound of Example 18 | 5.49 eV |
| Compound of Example 19 | 5.42 eV |

-continued

| | Work function |
|---|---|
| Compound of Example 20 | 5.36 eV |
| NPD | 5.54 eV |

As noted above, the indenoindole derivatives of the present invention show suitable energy levels, similarly to a work function of 5.5 eV shown by general hole transport materials such as NPD and TPD, and are found to have satisfactory hole transport capability.

Evaluation of Organic EL Element Properties

Example 22

An organic EL element was prepared by vapor depositing a hole injection layer 3, a hole transport layer 4, a light emission layer 5, an electron transport layer 6, an electron injection layer 7, and a cathode (aluminum electrode) 8 sequentially on an ITO electrode formed beforehand as a transparent anode 2 on a glass substrate 1, as shown in FIG. 22.

Concretely, the glass substrate 1 having a 150 nm thick ITO film formed thereon was cleaned with an organic solvent, and then cleaned on the surface by oxygen plasma treatment. Then, the ITO electrode-equipped glass substrate was mounted within a vacuum deposition machine, and the pressure was reduced to 0.001 Pa or lower. Then, a film of HIM-1 represented by a structural formula indicated below was formed in a thickness of 20 nm as the hole injection layer 3 so as to cover the transparent electrode 2. On the hole injection layer 3, a film of the compound of Example 1 (Compound 10) was formed in a thickness of 40 nm as the hole transport layer 4. On the hole transport layer 4, EMD-1 of the following structural formula and EMH-1 of the following structural formula were binary vapor-deposited at such deposition rates that the deposition rate ratio was EMD-1:EMH-1=5:95, whereby the resulting light emission layer 5 had a film thickness of 30 nm. On the light emission layer 5, a film of $Alq_3$ was formed in a thickness of 30 nm as the electron transport layer 6. On the electron transport layer 6, a film of lithium fluoride was formed in a thickness of 0.5 nm as the electron injection layer 7. Finally, aluminum was vapor deposited to a film thickness of 150 nm to form the cathode 8. The resulting organic EL element was measured for the light emission characteristics when a direct current voltage was applied at normal temperature in the atmosphere. The results of the measurements are shown in Table 1.

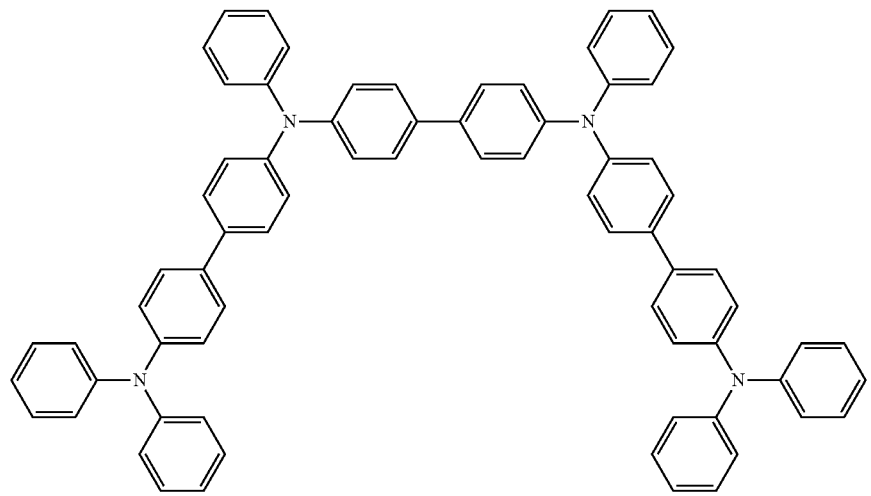

(HIM-1)

-continued

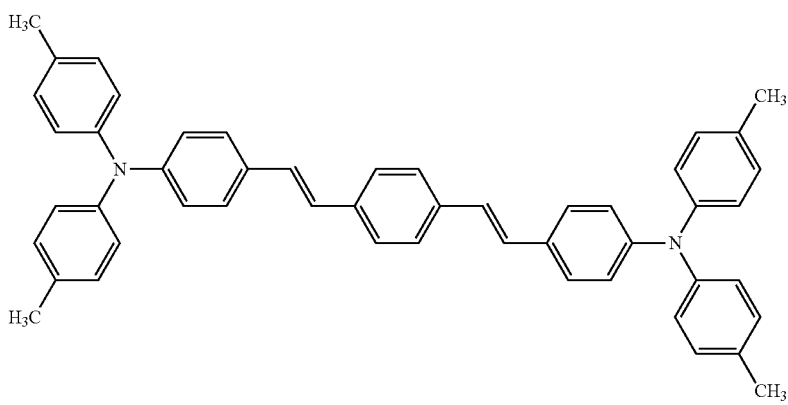
(EMD-1)

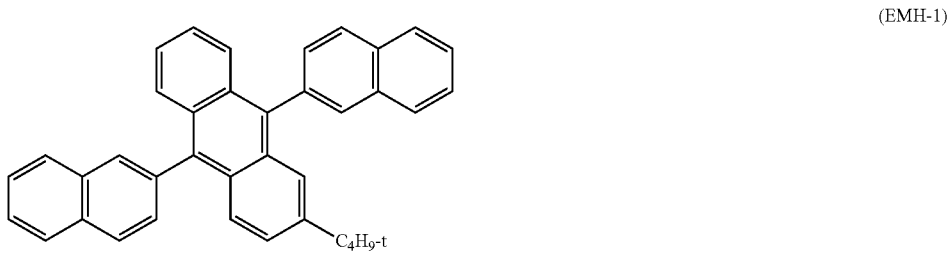
(EMH-1)

Example 23

An organic EL element was prepared in the same manner as in Example 22, except that the compound of Example 3 (Compound 6) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Example 24

An organic EL element was prepared in the same manner as in Example 22, except that the compound of Example 10 (Compound 78) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Example 25

An organic EL element was prepared in the same manner as in Example 22, except that the compound of Example 11 (Compound 79) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Example 26

An organic EL element was prepared in the same manner as in Example 22, except that the compound of Example 14 (Compound 9) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Example 27

An organic EL element was prepared in the same manner as in Example 22, except that the compound of Example 15 (Compound 11) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Example 28

An organic EL element was prepared in the same manner as in Example 22, except that the compound of Example 18

(Compound 51) was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Comparative Example 1

An organic EL element was prepared in the same manner as in Example 22, except that α-NPD was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

Comparative Example 2

An organic EL element was prepared in the same manner as in Example 22, except that HTM-1 of the following structural formula was used instead of the compound of Example 1 (Compound 10) as the material for the hole transport layer 4. The resulting organic EL element was measured for the light emission characteristics exhibited when a direct current voltage was applied at normal temperature in the atmosphere. The results of the measurements are shown in Table 1.

(HTM-1)

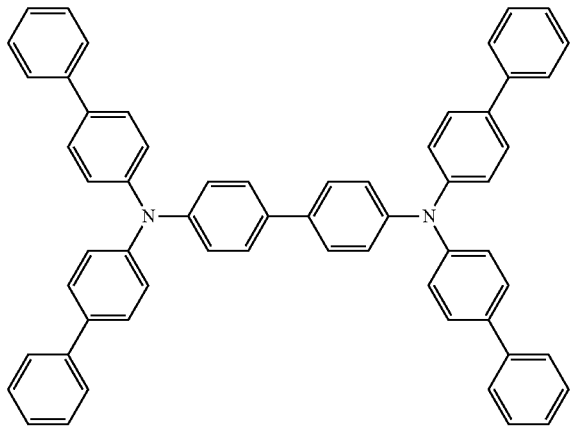

As shown in Table 1, the driving voltage when an electric current at a current density of 10 mA/cm$^2$ was flowed showed low values of 4.74 to 4.89V in the organic EL elements using the indenoindole derivatives of the present invention, as compared with 5.62V in the organic EL element using α-NPD used as a general hole transport material. Moreover, the driving voltage was equal to or lower than 4.87V of the organic EL element using HTM-1 known as a hole transport material having higher performance. The power efficiency was markedly increased at 5.33 to 6.52 lm/W in the organic EL elements using the indenoindole derivatives of the present invention, as contrasted with 5.06 lm/W of the organic EL element using α-NPD and 5.06 lm/W of the organic EL element using HTM-1.

As clear from the above results, the organic EL elements using the indenoindole derivatives of the present invention were found to be capable of achieving increases in the power efficiency and decreases in the practical driving voltage, in comparison with the organic EL element using α-NPD used as a general hole transport material. Even when compared with the organic EL element using HTM-1 known as a hole transport material having higher performance, the organic EL elements using the indenoindole derivatives of the present invention were found to be capable of achieving increases in the power efficiency.

<Evaluation of Light Emission Starting Voltage>

The results of measurements of the light emission starting voltage are shown below.

| Organic EL Element | Compound | Light emission starting voltage [V] |
|---|---|---|
| Example 22 | Comp. 10 | 2.7 |
| Example 23 | Comp. 6 | 2.8 |
| Example 24 | Comp. 78 | 2.7 |
| Example 25 | Comp. 79 | 2.8 |
| Example 26 | Comp. 9 | 2.7 |
| Example 27 | Comp. 11 | 2.8 |
| Example 28 | Comp. 51 | 2.7 |
| Comp. Ex. 1 | α-NPD | 2.9 |
| Comp. Ex. 2 | HTM-1 | 2.8 |

TABLE 1

| | Compound | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) |
|---|---|---|---|---|---|
| Ex. 22 | Comp. 10 | 4.75 | 920 | 9.20 | 6.09 |
| Ex. 23 | Comp. 6 | 4.88 | 849 | 8.49 | 5.46 |
| Ex. 24 | Comp. 78 | 4.75 | 877 | 8.77 | 5.80 |
| Ex. 25 | Comp. 79 | 4.86 | 926 | 9.26 | 6.00 |
| Ex. 26 | Comp. 9 | 4.80 | 815 | 8.15 | 5.33 |
| Ex. 27 | Comp. 11 | 4.89 | 1015 | 10.15 | 6.52 |
| Ex. 28 | Comp. 51 | 4.74 | 810 | 8.10 | 5.37 |
| Comp. Ex. 1 | α-NPD | 5.62 | 908 | 9.07 | 5.06 |
| Comp. Ex. 2 | HTM-1 | 4.87 | 783 | 7.84 | 5.06 |

In comparison with the organic EL element of Comparative Example 1 using α-NPD and the organic EL element of Comparative Example 2 using HTM-1, the organic EL elements using the indenoindole derivatives of the present invention were found to lower the light emission starting voltage equally or more greatly.

As shown above, the organic EL elements of the present invention were found to be capable of achieving increases in the power efficiency and decreases in the practical driving voltage, in comparison with the organic EL element using α-NPD used as a general hole transport material. Even when compared with the organic EL element using HTM-1 known as a hole transport material having higher performance, the organic EL elements of the present invention were found to be capable of achieving increases in the power efficiency.

INDUSTRIAL APPLICABILITY

The indenoindole derivative of the present invention is high in hole transport capability, excellent in electron blocking ability, and stable in a thin film state, so that it excels as a compound for an organic EL element. By preparing an organic EL element with the use of this compound, a high luminous efficiency and a high power efficiency can be obtained, the practical driving voltage can be lowered, and the durability can be improved. The resulting organic EL element can be put to uses such as domestic electrical appliances and illumination.

EXPLANATIONS OF LETTERS OR NUMERALS

1 Glass substrate
2 Transparent anode
3 Hole injection layer
4 Hole transport layer
5 Light emission layer
6 Electron Transport layer
7 Electron injection layer
8 Cathode

The invention claimed is:
1. An indenoindole derivative represented by the following formula:

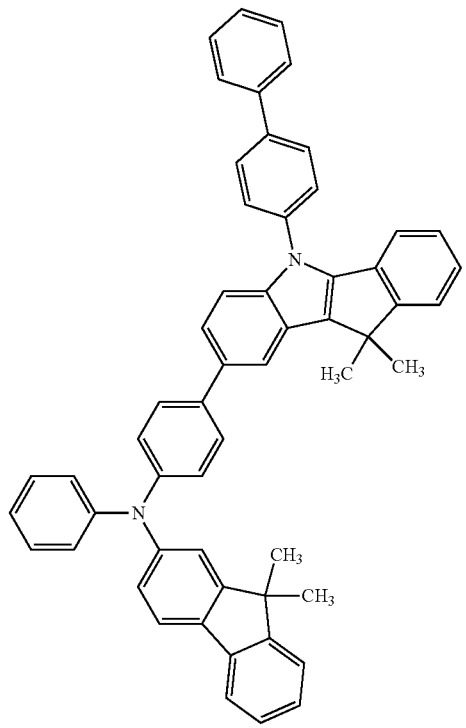 [SMILES: CC1(C)c2ccccc2-c2ccc(N(c3ccccc3)c3ccc(-c4ccc5c(c4)c4c(n5-c5ccc(-c6ccccc6)cc5)-c5ccccc5C4(C)C)cc3)cc21]

2. An organic electroluminescent element including a pair of electrodes and at least one organic layer sandwiched therebetween, wherein
the indenoindole derivative according to claim 1 is used as a constituent material for the at least one organic layer.
3. The organic electroluminescent element according to claim 2, wherein the organic layer is a hole transport layer.
4. The organic electroluminescent element according to claim 2, wherein the organic layer is an electron blocking layer.
5. The organic electroluminescent element according to claim 2, wherein the organic layer is a hole injection layer.
6. The organic electroluminescent element according to claim 2, wherein the organic layer is a light emission layer.

* * * * *